US007943594B2

(12) United States Patent
Seeberger et al.

(10) Patent No.: US 7,943,594 B2
(45) Date of Patent: May 17, 2011

(54) SOLID-PHASE AND SOLUTION-PHASE SYNTHESIS OF GLYCOSYLPHOSPHATIDYLINOSITOL GLYCANS

(75) Inventors: Peter H. Seeberger, Zurich (CH); Michael C. Hewitt, Cambridge, MA (US); Daniel A. Snyder, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 295 days.

(21) Appl. No.: 10/520,963

(22) PCT Filed: Jul. 10, 2003

(86) PCT No.: PCT/US03/21564
§ 371 (c)(1),
(2), (4) Date: Aug. 26, 2005

(87) PCT Pub. No.: WO2004/005532
PCT Pub. Date: Jan. 15, 2004

(65) Prior Publication Data
US 2006/0089330 A1 Apr. 27, 2006

Related U.S. Application Data

(60) Provisional application No. 60/394,794, filed on Jul. 10, 2002.

(51) Int. Cl.
A61K 31/715 (2006.01)
A61K 31/70 (2006.01)
A61K 31/7028 (2006.01)
A61K 31/7034 (2006.01)
C07H 5/04 (2006.01)
C08B 37/00 (2006.01)

(52) U.S. Cl. ............ 514/54; 514/25; 514/35; 536/18.7; 536/17.2; 536/124

(58) Field of Classification Search .................... 514/54, 514/25, 35, 53, 62; 536/17.2, 18.7, 124
See application file for complete search history.

(56) References Cited

U.S. PATENT DOCUMENTS

| | | | |
|---|---|---|---|
| 3,936,351 A | 2/1976 | Bianchini | 195/4 |
| 4,122,196 A | 10/1978 | Robbins et al. | 426/60 |
| 4,863,874 A | 9/1989 | Wassef et al. | 436/501 |
| 4,904,594 A | 2/1990 | Karlstam | 435/201 |
| 4,977,091 A | 12/1990 | Gilmanov et al. | 435/271 |
| 5,001,064 A | 3/1991 | Deuel | 435/194 |
| 5,100,787 A | 3/1992 | Shimizu et al. | 435/131 |
| 5,214,180 A | 5/1993 | Ferrari et al. | 558/146 |
| 5,223,394 A | 6/1993 | Wallner | 435/6 |
| 5,227,508 A | 7/1993 | Kozikowski et al. | 558/155 |
| 5,229,376 A | 7/1993 | Alving et al. | 514/76 |
| 5,268,272 A | 12/1993 | Müllner et al. | 435/52 |
| 5,340,731 A | 8/1994 | Kilburn et al. | 435/179 |
| 5,352,810 A | 10/1994 | Brufani et al. | 554/79 |
| 5,378,725 A | 1/1995 | Bonjouklian et al. | 514/453 |
| 5,418,147 A | 5/1995 | Huang et al. | 435/69.1 |
| 5,504,103 A | 4/1996 | Bonjouklian et al. | 514/453 |
| 5,601,999 A | 2/1997 | Matsuzaki et al. | 435/72 |
| 5,624,903 A | 4/1997 | Müller et al. | 514/18 |
| 5,726,167 A | 3/1998 | Dodge et al. | 514/172 |
| 5,741,689 A | 4/1998 | Dhand et al. | 435/194 |
| 5,760,259 A | 6/1998 | Gordon et al. | 554/224 |
| 5,831,077 A | 11/1998 | Redmond et al. | 536/55.3 |
| 5,856,132 A | 1/1999 | Stephens et al. | 435/69.2 |
| 5,856,133 A | 1/1999 | Stephens et al. | 435/69.2 |
| 5,859,201 A | 1/1999 | Stephens et al. | 530/350 |
| 5,869,271 A | 2/1999 | Stephens et al. | 435/15 |
| 5,874,273 A | 2/1999 | Stephens et al. | 435/194 |
| 5,885,777 A | 3/1999 | Stoyanov et al. | 435/6 |
| 5,916,764 A | 6/1999 | Bandman et al. | 435/69.1 |
| 5,919,659 A | 7/1999 | Hillman et al. | 435/69.1 |
| 5,955,277 A | 9/1999 | Hansen et al. | 435/6 |
| 5,955,338 A | 9/1999 | Hillman et al. | 435/196 |
| 6,004,938 A | 12/1999 | Frick et al. | 514/25 |
| 6,017,763 A | 1/2000 | Stephens et al. | 436/6 |
| 6,034,063 A | 3/2000 | Hillman et al. | 514/12 |
| 6,043,062 A | 3/2000 | Klippel et al. | 435/131 |
| 6,048,989 A | 4/2000 | Gordon et al. | 549/499 |
| 6,077,951 A | 6/2000 | Redmond et al. | 536/55.3 |
| 6,110,718 A | 8/2000 | Shisheva | 435/194 |
| 6,127,267 A | 10/2000 | Matsubara et al. | 435/656 |
| 6,133,419 A | 10/2000 | Braselman | 530/350 |
| 6,136,798 A | 10/2000 | Cody et al. | 514/141 |
| 6,218,546 B1 | 4/2001 | Watzele et al. | 548/304.1 |

(Continued)

FOREIGN PATENT DOCUMENTS

WO WO 01/85745 A1 * 11/2001

OTHER PUBLICATIONS

Madsen et al. (Journal of the American Chemical Society (1995), vol. 117. No. 5, pp. 1554-1565).*
Martin-Lomas et al. (Chem. Eur. J. 2000, 6, No. 19, pp. 3608-3621).*
Jaworek et al. (Carbohydrates Research 331 (2001) 375-391).*
Kong et al. (CN 1297892, Jun. 6, 20001) (Abstract Only).*
Jiang et al. (Chemical Communications (Cambridge) (1996), (18), 2193-2194).*
Baeschlin, D. K. et al., "1,2-Diacetals in synthesis: total synthesis of a Glycosylphosphatidyllinositol Anchor of *Trypanosoma brucei*", *Chem. Eur. J.*, 6(1):172-186 (VCH Publishers, US) (2000).
Hewitt, M. C. et al., "Rapid Synthesis of a Glycosylphosphatidylinositol-Based Malaria Vaccine Using Automated Solid-Phase Oligosaccharide Synthesis", *J. Am. Chem. Soc.*, 124(45):13434-13436 (2002).
Schofield, L. et al., "Synthetic GPI as a candidate anti-toxic vaccine in a model of malaria", *Nature*, 418(15):785-789 (Nature Publishing Group, London, GB)(Aug. 15, 2002).
Udodong, U. E. et al., "A Ready Convergent Synthesis of the Heptasaccharide GPI Membrane Anchor of Rat Brain Thy-1 Glycoprotein", *J. Am. Chem. Soc.*, 115:7886-7887 (American Chemical Society, Washington, DC, US)(1993).
Supplementary European Search Report dated Oct. 10, 2007.

* cited by examiner

*Primary Examiner* — Shaojia Anna Jiang
*Assistant Examiner* — Michael C Henry
(74) *Attorney, Agent, or Firm* — Dana M. Gordon; Foley Hoag LLP

(57) ABSTRACT

One aspect of the present invention relates to solution-phase approaches to GPI synthesis. Another aspect of the present invention relates to key building blocks, and syntheses thereof, useful for GPI assembly. Yet another aspect of the invention relates to an automated method for the synthesis of GPIs and fragments thereof.

18 Claims, 34 Drawing Sheets

U.S. PATENT DOCUMENTS

| | | | |
|---|---|---|---|
| 6,277,373 B1 | 8/2001 | Hillman et al. | 424/94.64 |
| 6,291,220 B1 | 9/2001 | Williams et al. | 435/194 |
| 6,300,111 B1 | 10/2001 | Klippel et al. | 435/194 |
| 6,323,332 B1 | 11/2001 | Fukuda et al. | 536/23.2 |
| 6,348,580 B1 | 2/2002 | Fukui et al. | 530/388.1 |
| 6,395,468 B1 | 5/2002 | Bandman et al. | 435/4 |
| 6,406,875 B1 | 6/2002 | Shisheva | 435/15 |
| 6,410,700 B1 | 6/2002 | Williams et al. | 536/18.7 |
| 6,413,773 B1 | 7/2002 | Ptasznik et al. | 435/377 |
| 6,518,277 B1 | 2/2003 | Sadhu et al. | 514/266 |
| 6,596,689 B2 | 7/2003 | Misevic | 514/8 |
| 6,667,300 B2 | 12/2003 | Sadhu et al. | 514/183 |
| 6,709,833 B2 | 3/2004 | Fukui et al. | 435/7.95 |
| 6,762,284 B1 | 7/2004 | Braselman | 530/350 |
| 6,800,620 B2 | 10/2004 | Sadhu et al. | 514/183 |
| 6,818,408 B2 | 11/2004 | Fukui et al. | 435/7.1 |
| 2002/0037276 A1 | 3/2002 | Ptasznik et al. | 424/93.7 |
| 2002/0120107 A1 | 8/2002 | Fukui et al. | 530/388.1 |
| 2002/0127217 A1 | 9/2002 | Hillman et al. | 424/94.6 |
| 2002/0161014 A1 | 10/2002 | Sadhu et al. | 514/266.2 |
| 2002/0164750 A1 | 11/2002 | Meyers et al. | 435/194 |
| 2002/0177699 A1 | 11/2002 | Bandman et al. | 536/23.1 |
| 2003/0008321 A1 | 1/2003 | Fukui et al. | 435/7.1 |
| 2003/0082621 A1 | 5/2003 | Misevic | 435/7.1 |
| 2003/0114400 A1 | 6/2003 | Bennett et al. | 514/44 |
| 2003/0190651 A1 | 10/2003 | Kossida | 435/6 |
| 2003/0195211 A1 | 10/2003 | Sadhu et al. | 514/234.5 |
| 2003/0232775 A1 | 12/2003 | Dobie et al. | 514/44 |
| 2003/0232777 A1 | 12/2003 | Marcusson et al. | 514/44 |
| 2004/0022793 A1 | 2/2004 | Severn et al. | 424/184.1 |
| 2004/0110263 A1 | 6/2004 | Schofield et al. | 435/196 |
| 2004/0147033 A1 | 7/2004 | Shriver et al. | 436/87 |
| 2004/0152201 A1 | 8/2004 | Murray | 436/94 |
| 2005/0043514 A1 | 2/2005 | Fukui et al. | 530/387.1 |
| 2006/0147476 A1* | 7/2006 | Schofield | 424/268.1 |

(continued in Figure 1B)

Figure 1B
(continued from Figure 1A)
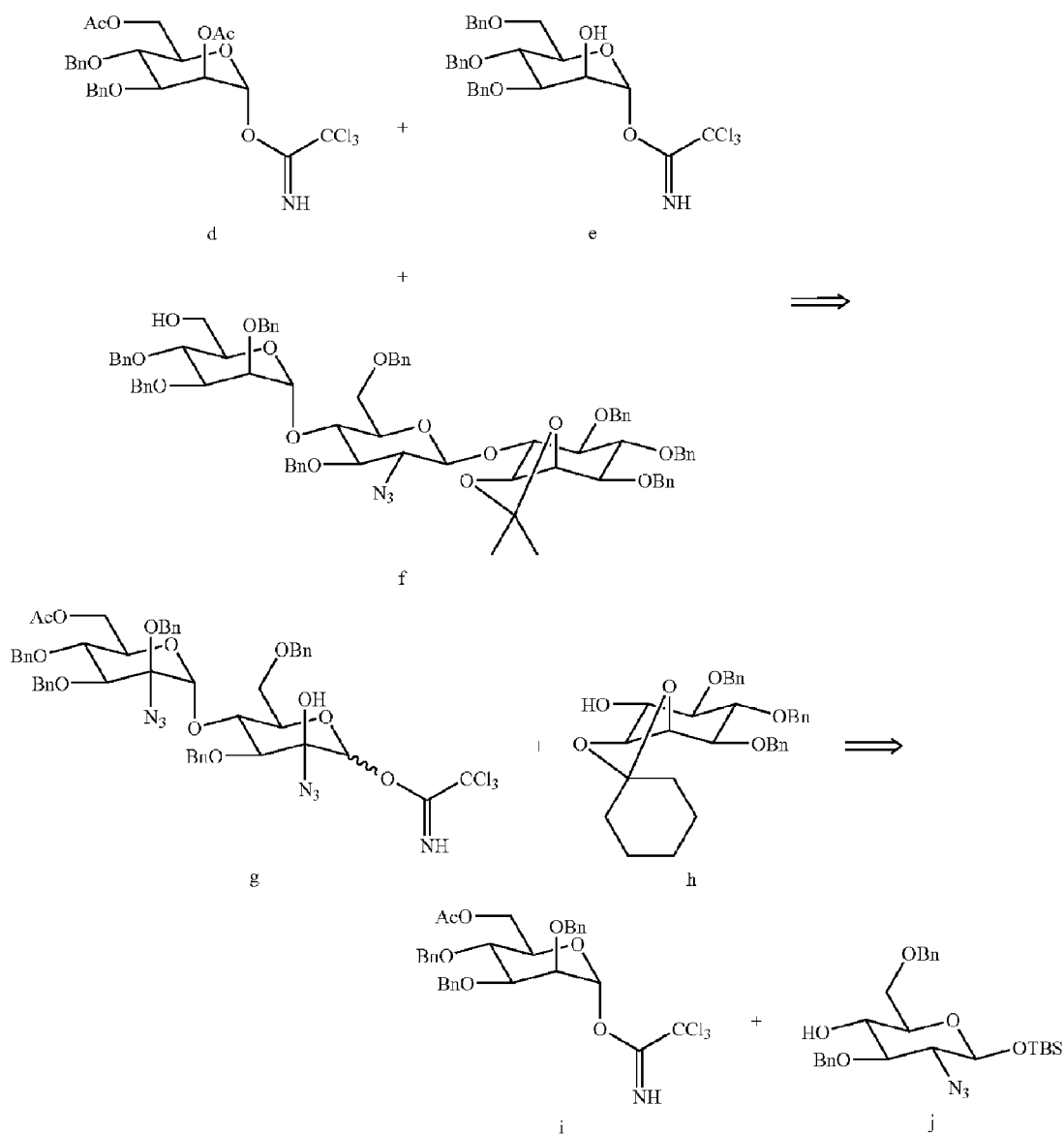

(continued in Figure 2B)

Figure 2B
(continued from Figure 2A)
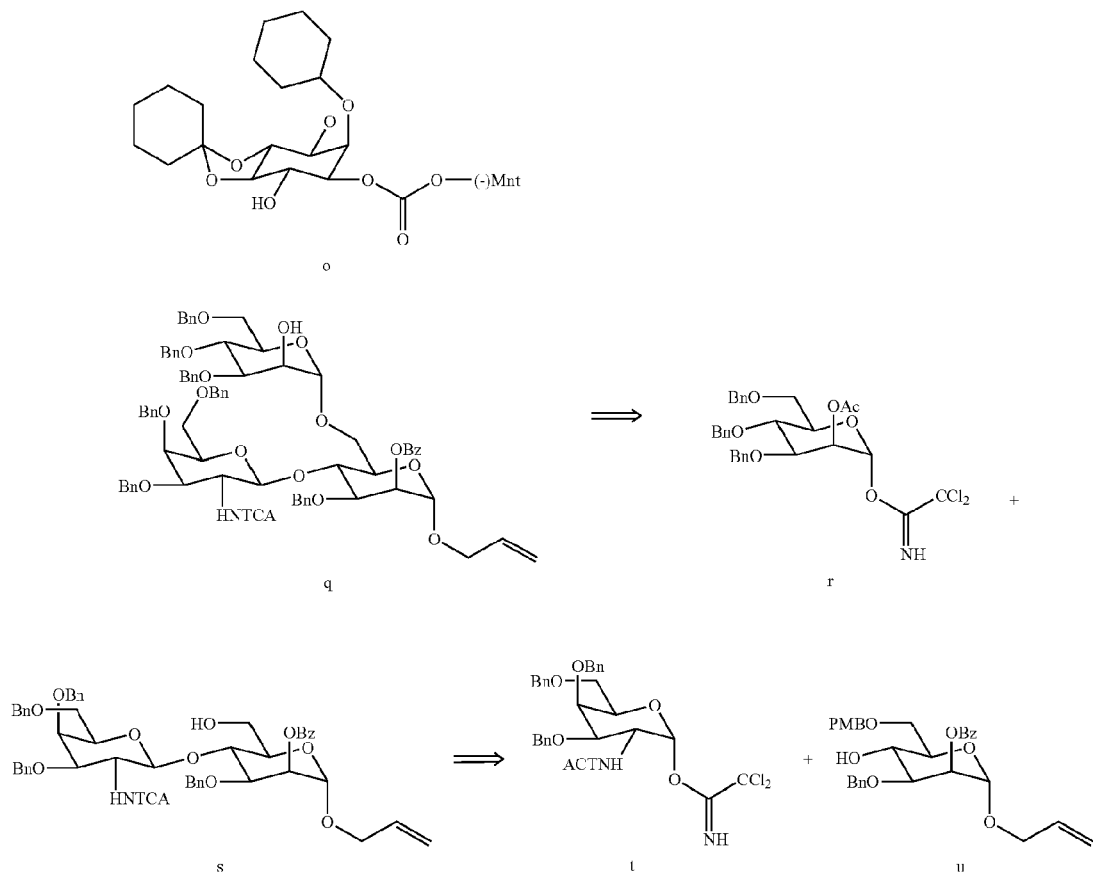

(continued in Figure 4B)

Figure 4B
(continued from Figure 4A)
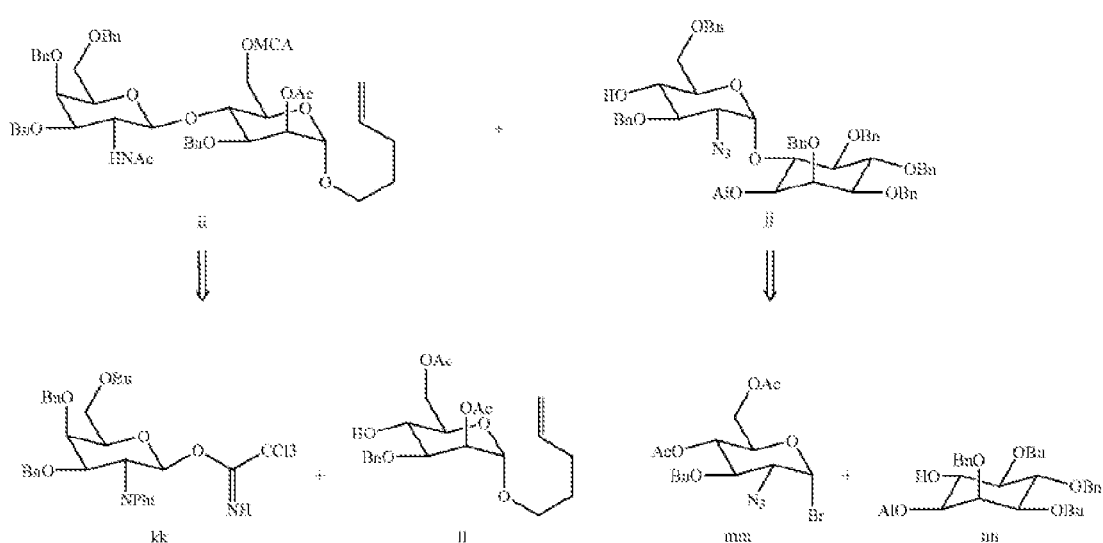

(continued in Figure 12B)

Figure 12B
(continued from Figure 12A)
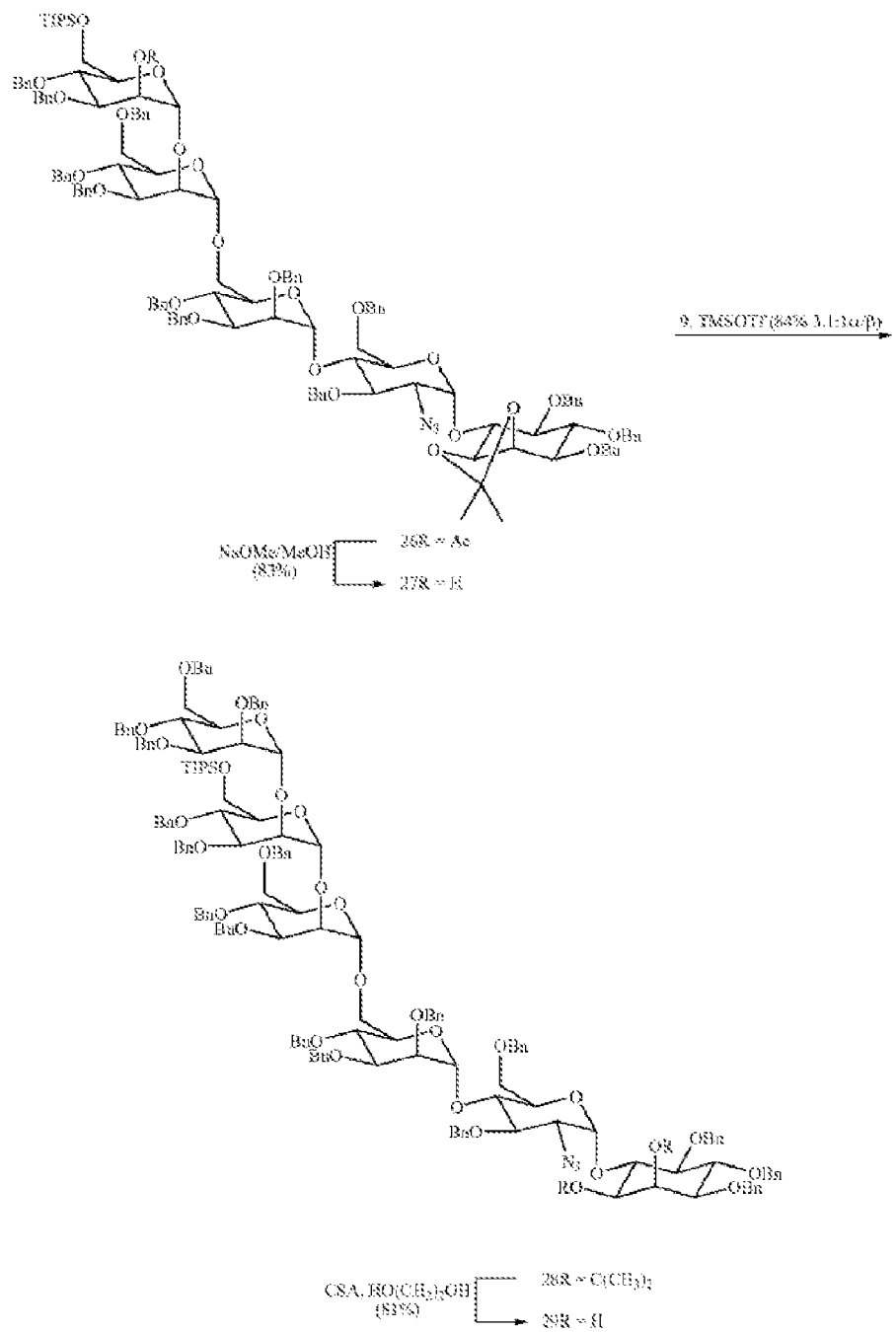

30

31

7, TMSOTf(quant.)

1. 0.5M HCl/MeOH
2. TBSCl, Imid. (67% 2 steps)

38 R = Ac
NaOMe/MeOH (72%) → 39 R = H
NaH, BnBr (95%) → 40 R = Bn (continued in Figure 15B)

Figure 15B
(continued from Figure 15A)
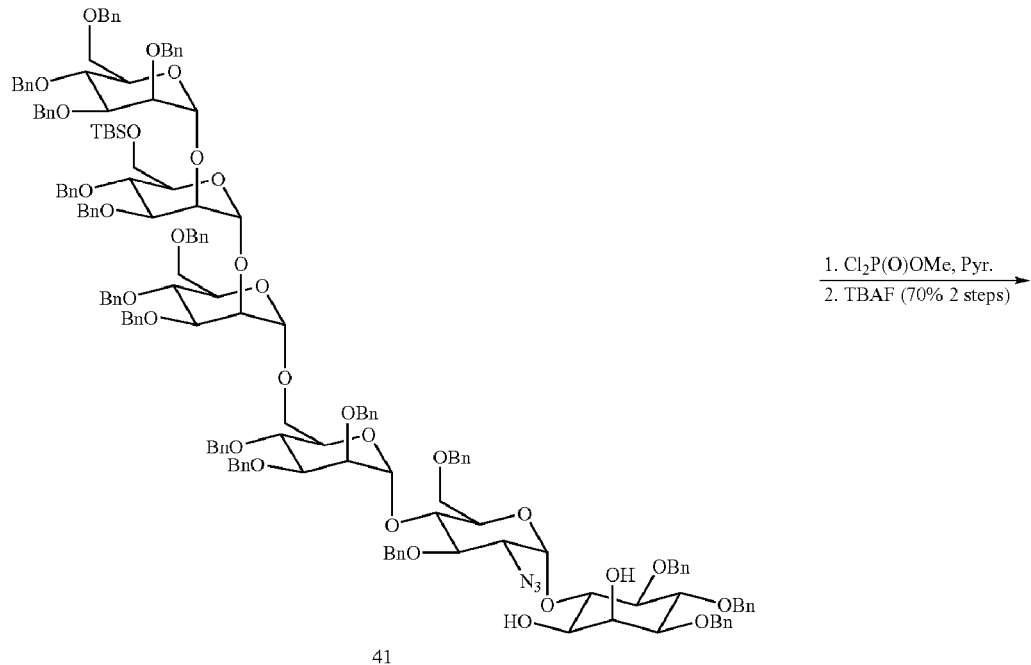
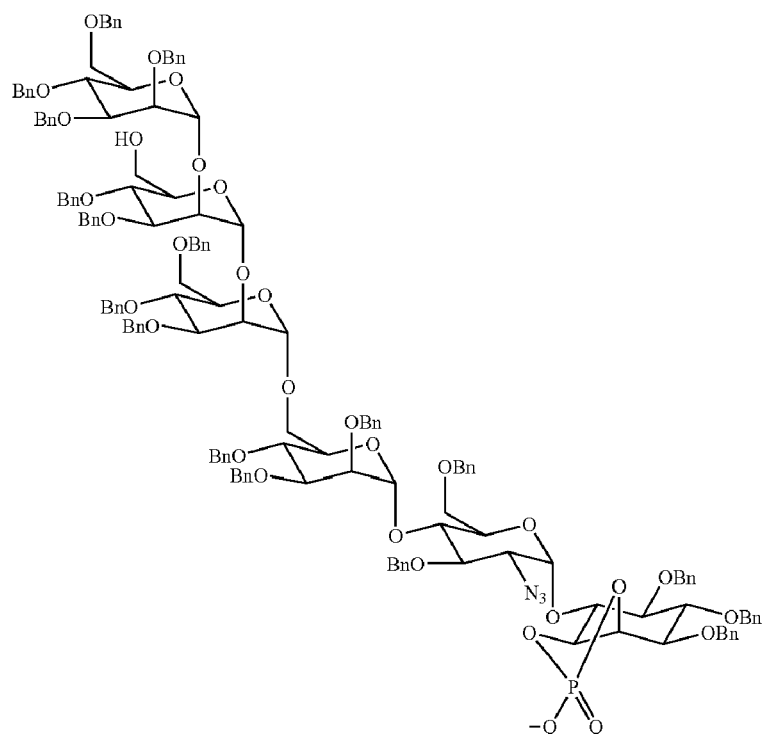

(continued in Figure 20B)

Figure 20 B
(continued from Figure 20A)
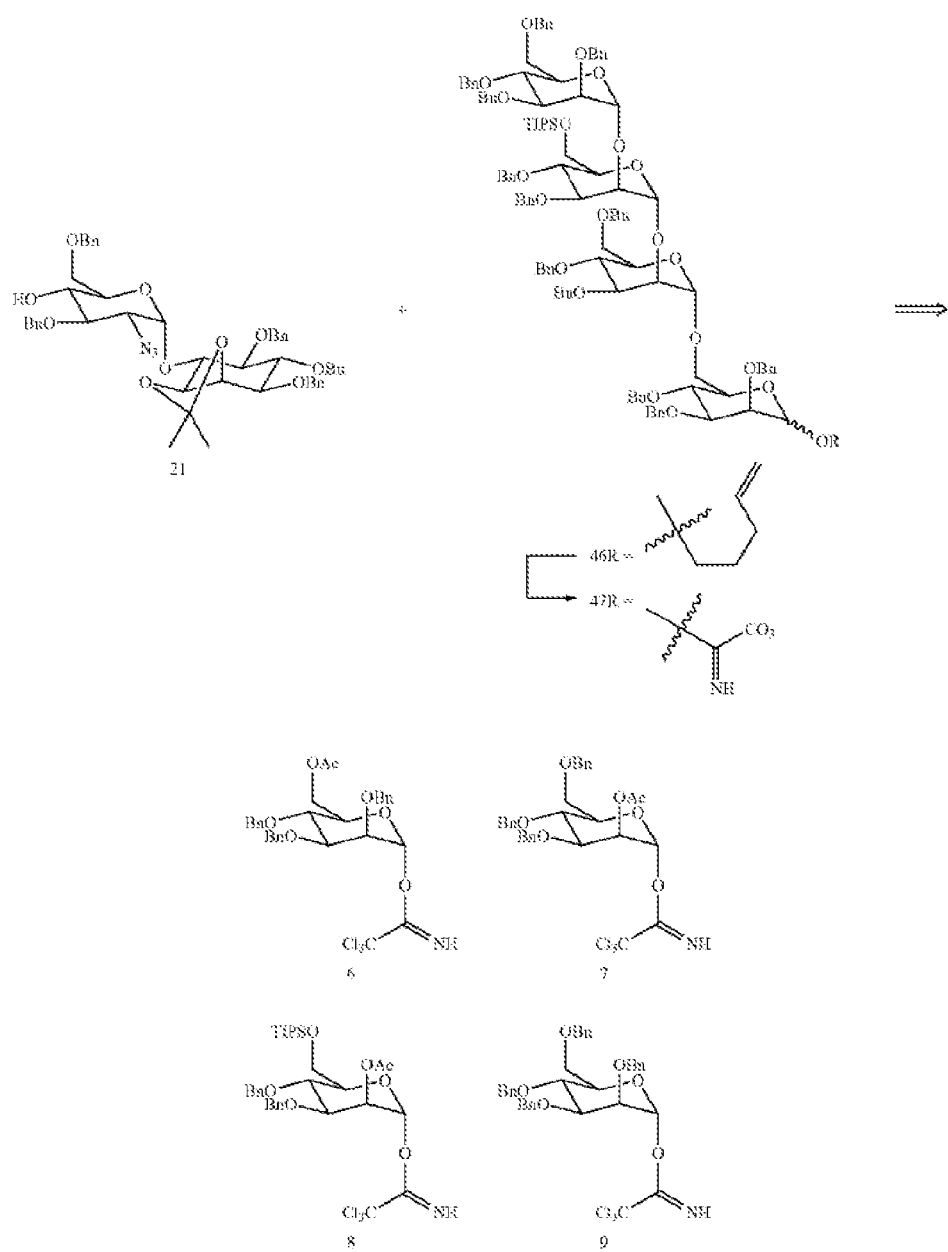

Figure 22

| Function | Reagent | Time (min) |
| --- | --- | --- |
| Glycosylation | 5 equiv. donor and 5 equiv. TMSOTf | 20 |
| Wash | Dichloromethane | 9 |
| Glycosylation | 5 equiv. donor and 5 equiv. TMSOTf | 20 |
| Wash | Dichloromethane | 9 |
| Deprotection | 2 × 10 equiv. NaOMe | 60 |
| Wash | 0.2 M AcOH/0.2 M MeOH/THF | 9 |
| Wash | Tetrahydrofuran | 9 |
| Wash | Dichloromethane | 9 |

(continued in Figure 27B)

Figure 27B
(continued from Figure 27A)
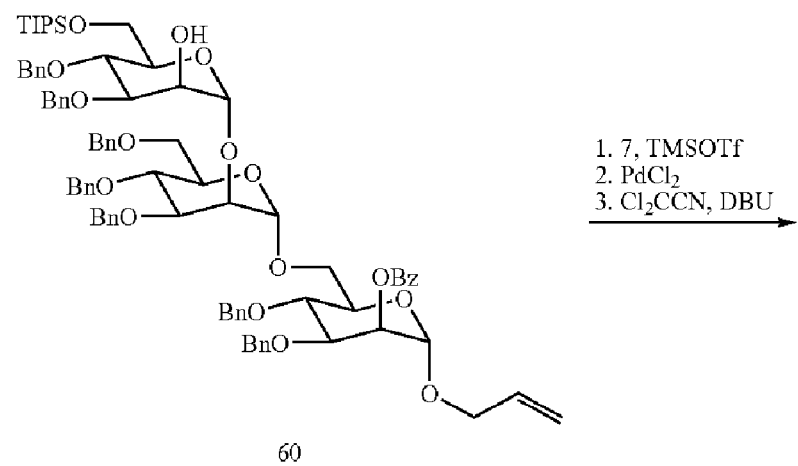
60
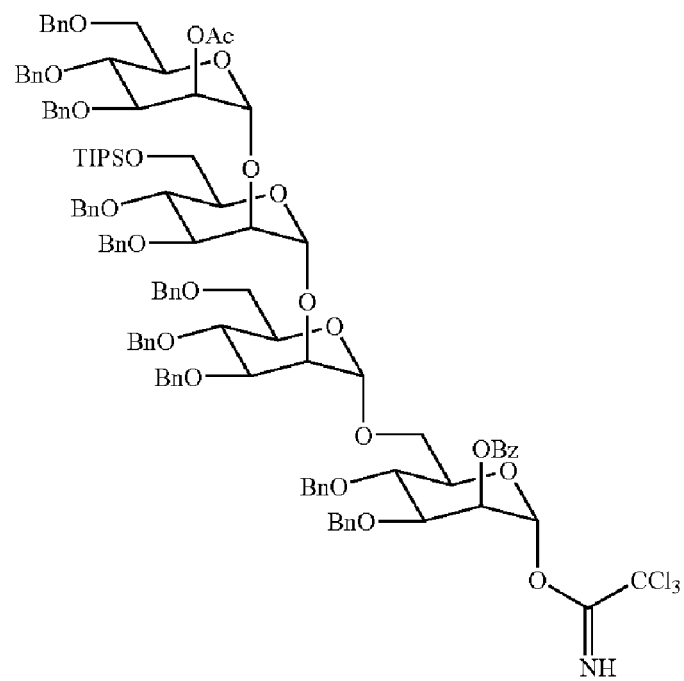
61

SOLID-PHASE AND SOLUTION-PHASE SYNTHESIS OF GLYCOSYLPHOSPHATIDYLINOSITOL GLYCANS

This application claims the benefit of priority to Patent Cooperation Treaty Application serial number PCT/US03/21564, filed Jul. 10, 2003; which claims the benefit of priority to U.S. Provisional Patent Application Ser. No. 60/394,794, filed Jul. 10, 2002.

BACKGROUND OF THE INVENTION

Glycosylphosphatidylinositol (GPI) structures are ubiquitous in nature—they occur in almost all organisms except eubacteria, and roughly 0.5% of all proteins are expected, based on genomic analysis, to be linked to the cell surface via GPI anchors.[1] Many organisms, especially protozoa, also express non-protein-linked GPI-type glycans on their cell surfaces; these are often essential for virulence, immune evasion, and other important properties.[2] In addition to their structural functions, GPI molecules serve as intermediate messengers in signal-transduction pathways involving hormones, cytokines, and growth factors.[3] GPIs are especially important because of their roles in tropical diseases such as malaria and typanosomiasis,[2] genetic disease,[4] diabetes,[3] and cancer.[5]

GPIs have substantial structural similarity, with a conserved Man($\alpha$1→2)Man($\alpha$1→6)Man($\alpha$1→4)GlcN($\alpha$1→6) myo-iositol core structure attached to protein via an ethanolamine phosphate on the 6-OH of the terminal mannose and to the outer membrane leaflet via a lipid on the 1-OH of inositol.[1] A given GPI may consist of this core only, or be decorated with saccharides or other moieties; for example, mammalian GPIs have additional phosphoethanolamine, whereas protozoa lack this modification. As many different functionalizations are possible, GPIs found in nature are usually highly heterogeneous.[6]

The difficulty of purifying polyfunctional molecules such as GPIs from natural sources, the paucity of different structures thus available, and the inevitable heterogeneity of the material isolated suggest chemical synthesis as a general solution to the application of GPIs.

Accordingly, GPIs have attracted the attention of synthetic organic chemists since their discovery, resulting in a number of syntheses. The ceramide-containing GPI anchor of yeast (*Saccharomyces cerevisiae*),[7] acylglycerol containing GPI anchor of *Trypanosoma brucei*,[8] and rat brain Thy-1[9] have all been completed in the last ten years using a variety of methodologies and protecting group combinations. In addition, GPI structures have been prepared for biological studies aimed at elucidating the insulin signaling pathway.[10]

Müller et al. have reported a synthesis using a.[10] See FIG. 1A and FIG. 1B. This route is non-convergent, making modification more difficult; it suffers from a dependence on protecting-group manipulations on large structures, which results in loss of more valuable material; and the protecting-group combinations used (esp. the TBS and isopropylidine) are incompletely orthogonal and restrict the diversity of structures possible.

Schmidt et al. have reported a method using k.[11] See FIG. 2A and FIG. 2B. This synthesis, much like the one mentioned previously, shows some similarity to our methods, indicating a limited degree of consensus among GPI chemists. See the extended commentary, infra, for analysis.

Martin-Lomas et al. used v as an intermediate.[10] See FIG. 3. Their method uses a variety of protecting group-patterns requiring late-stage manipulation; it also lacks the flexibility to install phosphate moieties in the natural manner (or at all), thus limiting the utility for making structures recognized by biological systems.

Fraser-Reid et al. have made cc, which incorporates many robust and generally useful protecting-group patterns.[12] See FIG. 4A and FIG. 4B. The principal drawback to this route is the near-exclusive use of n-pentenyl glycoside donors, developed by the group; although these do provide acceptable results, their lack of adoption by the carbohydrate-synthesis community at large is testament to the difficulty of applying them successfully. Our method uses more common techniques which are reliable even when applied by less-skilled operators.

Similarly, many of the protection schemes used by Ley et al. in oo are intended to demonstrate a new technology rather than produce optimal results or versatility.[8] See FIG. 5. Although the generation of large structures is possible, our simple, general methods provide greater opportunities for easy modification of the synthesis, minimize the chances of protecting-group incompatibility, and make deprotection of the final structures simpler.

SUMMARY OF THE INVENTION

One aspect of the present invention relates to solution-phase approaches to GPI synthesis. Another aspect of the present invention relates to key building blocks, and syntheses thereof, useful for GPI assembly. Yet another aspect of the invention relates to an automated method for the synthesis of GPIs and fragments thereof.

Further, despite the tremendous amount of work on the synthesis of GPIs, there have been no solid-phase or automated syntheses reported. The application of our automated carbohydrate synthesizer to this challenge has reduced the amount of time required for synthesis of GPIs, and may also be used to generate structurally related GPIs using a block coupling approach (vide supra). Herein we disclose inter alia the solution-phase synthesis of a GPI found within the context of malaria infections, and an automated solid-phase synthesis that was completed in a fraction of the time required for the solution-phase synthesis. Notably, the synthetic methods may be used to assemble any biologically important GPI.

Given the importance of GPI's in a variety of diseases including malaria, diabetes, neurodegenerative diseases and inflammation, access to defined structures of this class will be of major commercial significance. The methods of the present invention will serve as research tools for target identification, target validation and assay development; and certain GPIs of the present invention are expected to be drug candidates.

BRIEF DESCRIPTION OF THE FIGURES

FIGS. 1A and 1B depict a retrosynthesis from Muller et al. *Biochem.* 1998, 37, 13421.

FIGS. 2A and 2B depict a retrosynthesis from Schmidt et al. *J. Org. Chem.* 2001, 66, 7432.

FIGS. 4A and 4B depict a retrosynthesis from Fraser-Reid et al. *J. Am. Chem. Soc.* 1993, 115, 7886; *J. Am. Chem. Soc.* 1995, 117, 1554; and *J. Am. Chem. Soc.* 1995, 117, 10387.

FIGS. 12A and 12B depict a first generation synthesis.

FIGS. 15A and 15B depict a synthesis of cyclic phosphate.

FIGS. 20A and 20B depict a retrosynthesis for automated synthesis.

FIG. 22 depicts a table showing conditions for automated synthesis of 46.

FIGS. 27A and 27B depict a synthesis of more-versatile tetramannose donor.

DETAILED DESCRIPTION OF THE INVENTION

Figure 1A:
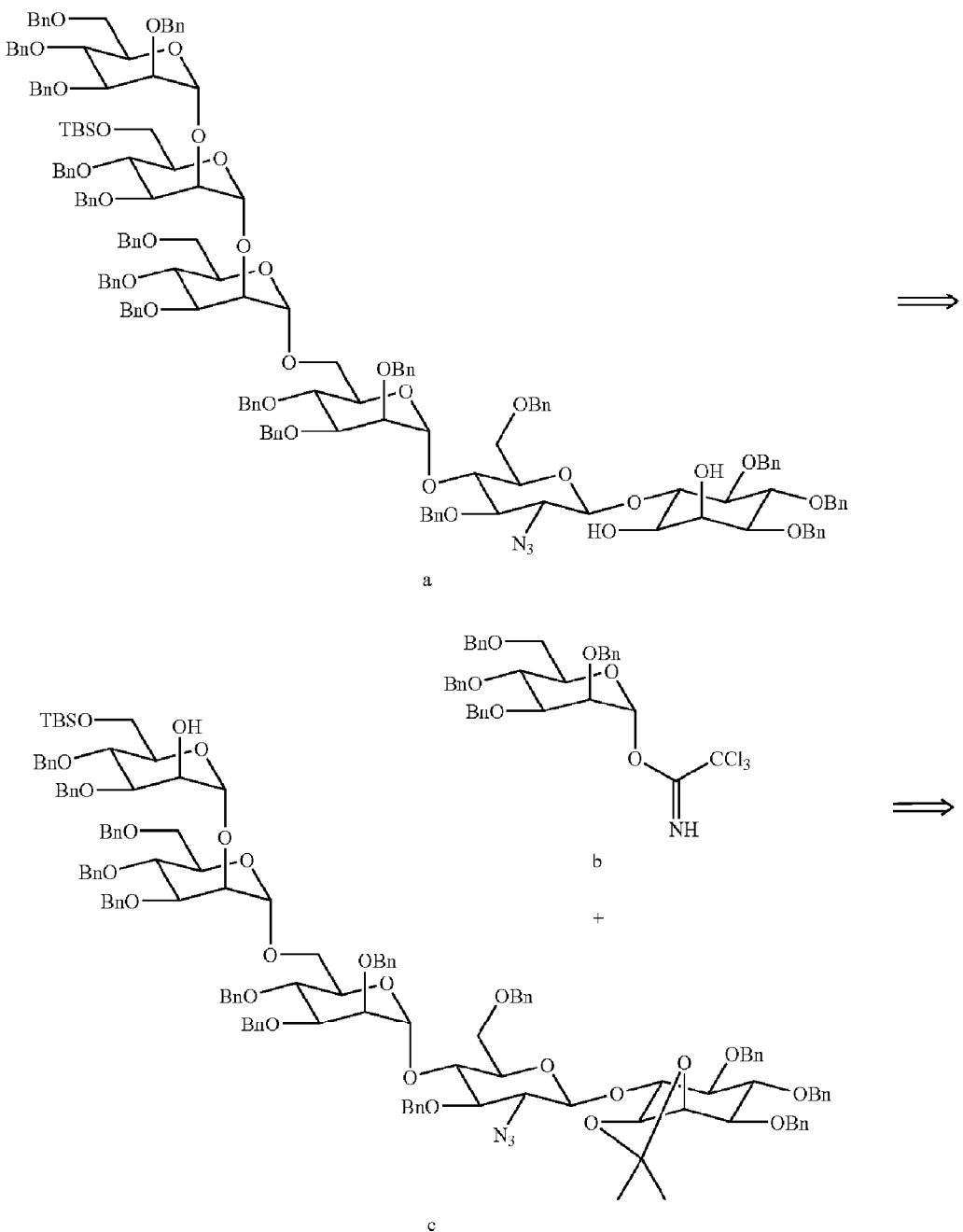
Figure 2A:
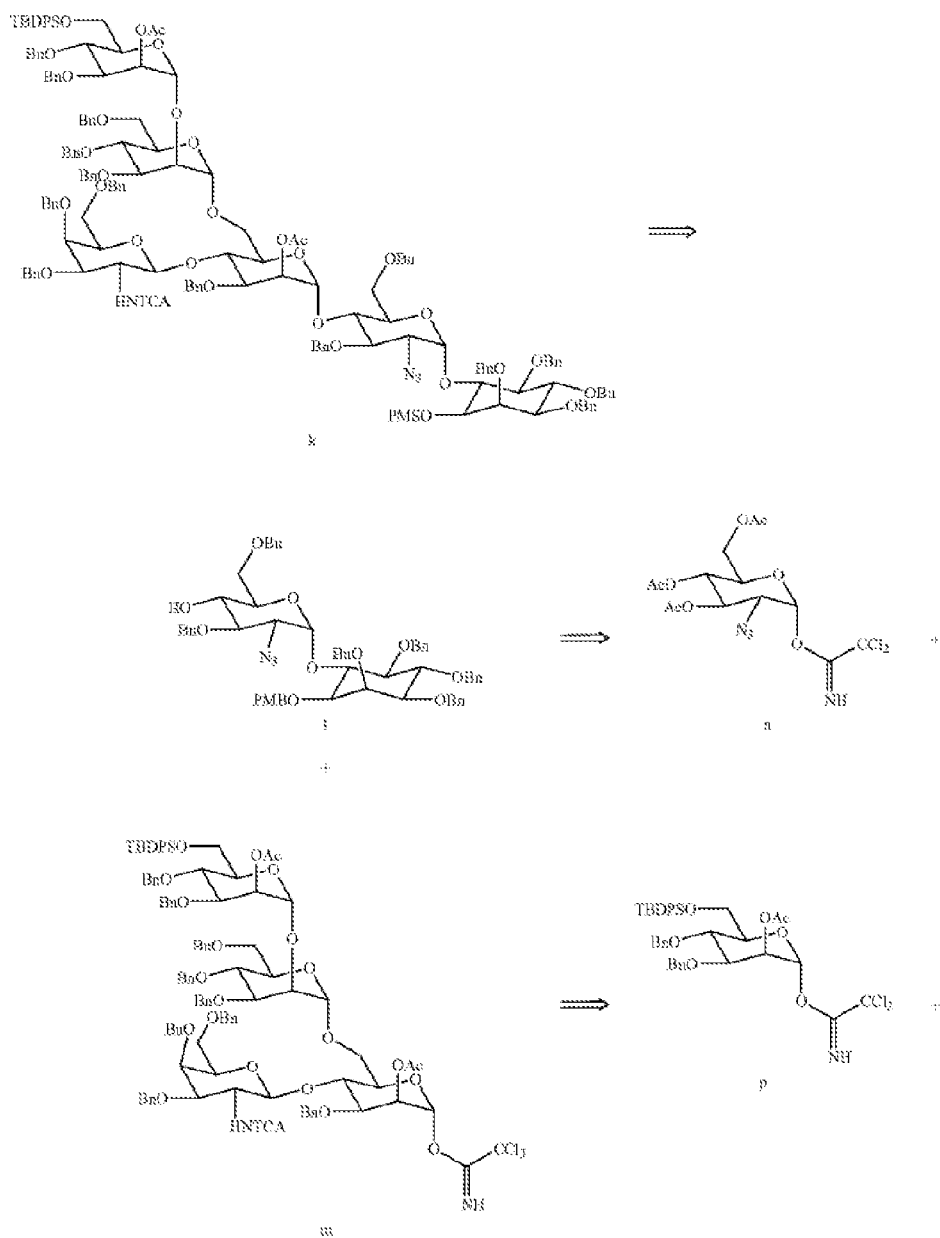
Figure 3:
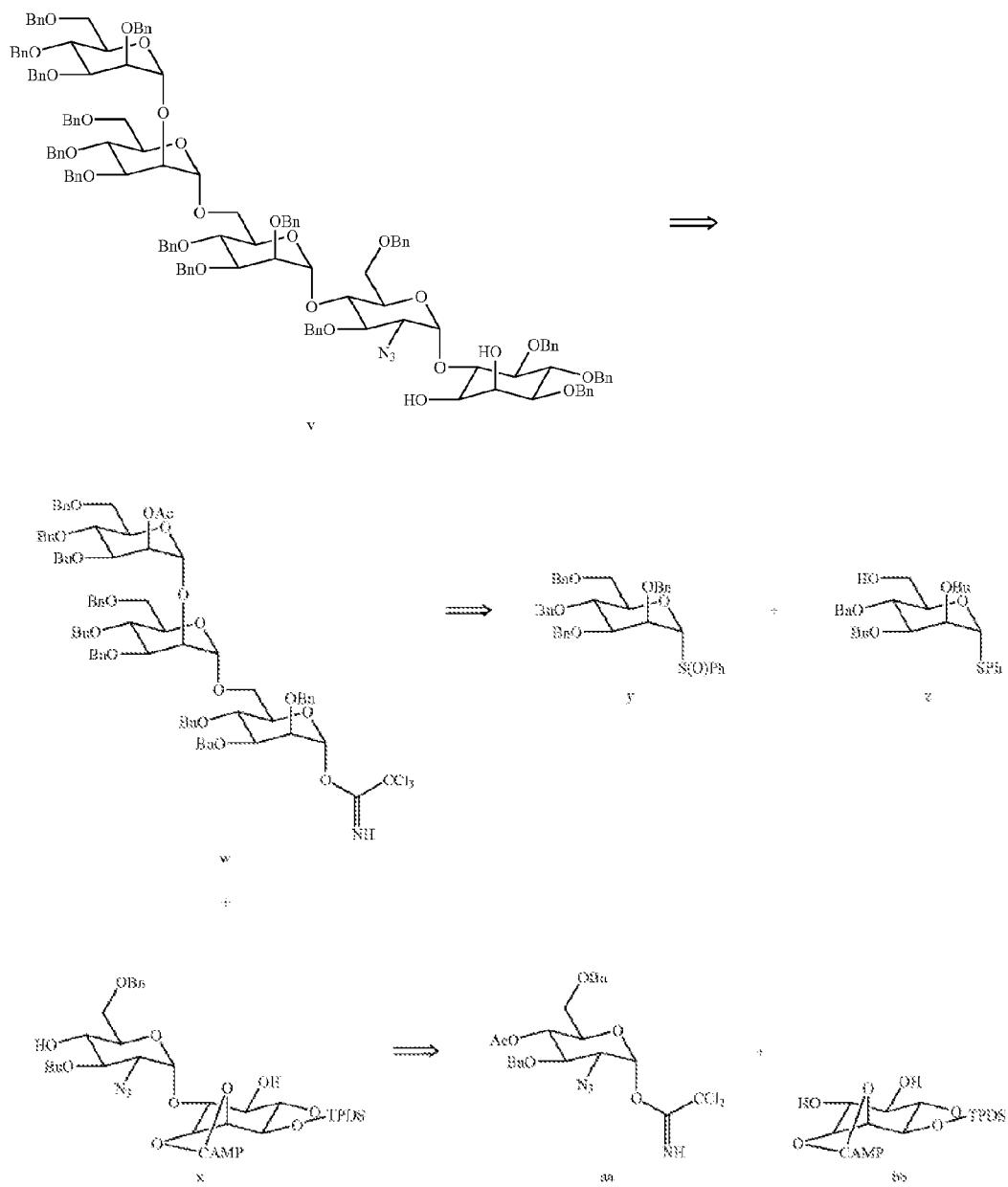
FIG. 3 depicts a retrosynthesis from Martin-Lomas et al. *Chem. Eur. J.* 2002, 6, 3608.
Figure 4A:
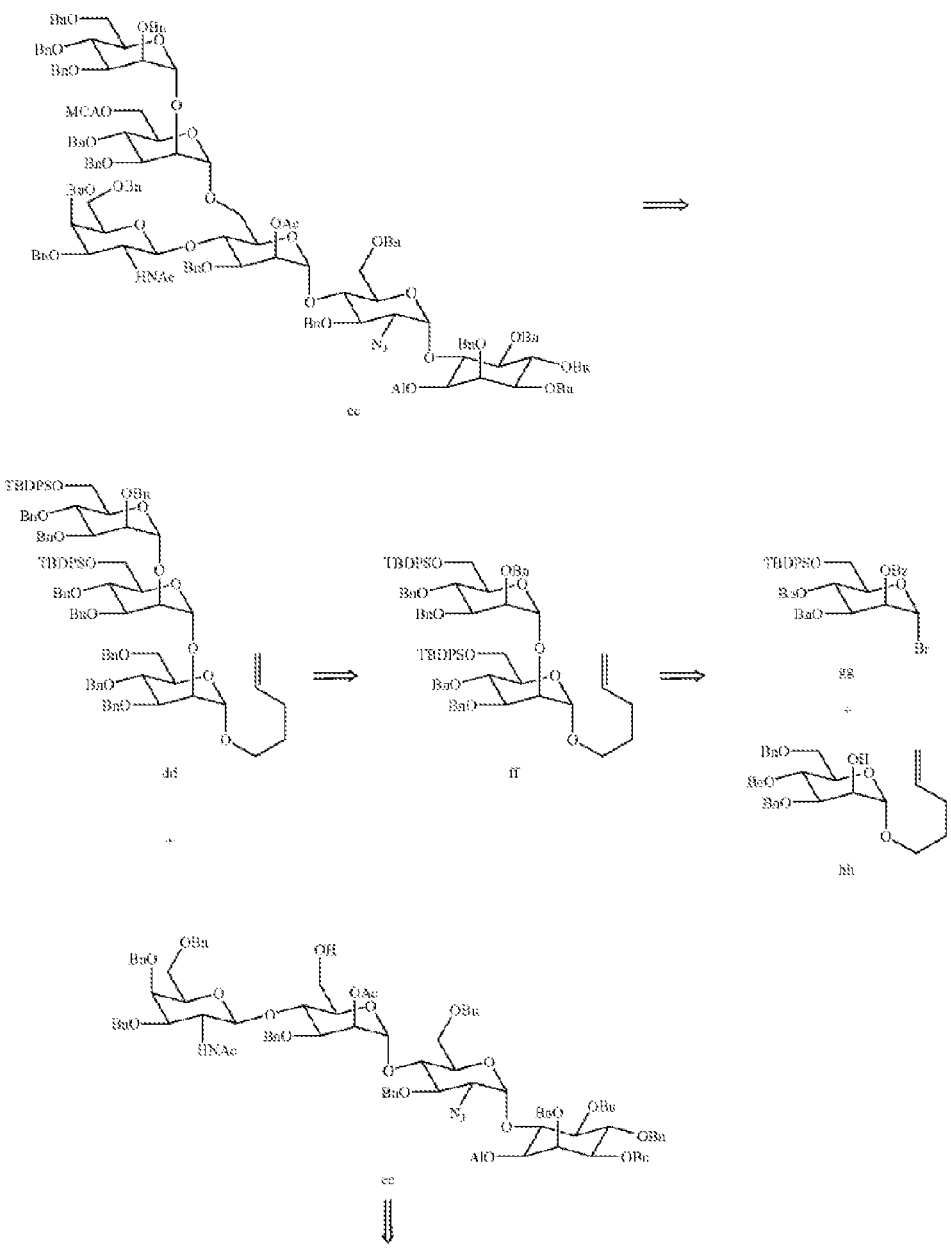
Figure 5:
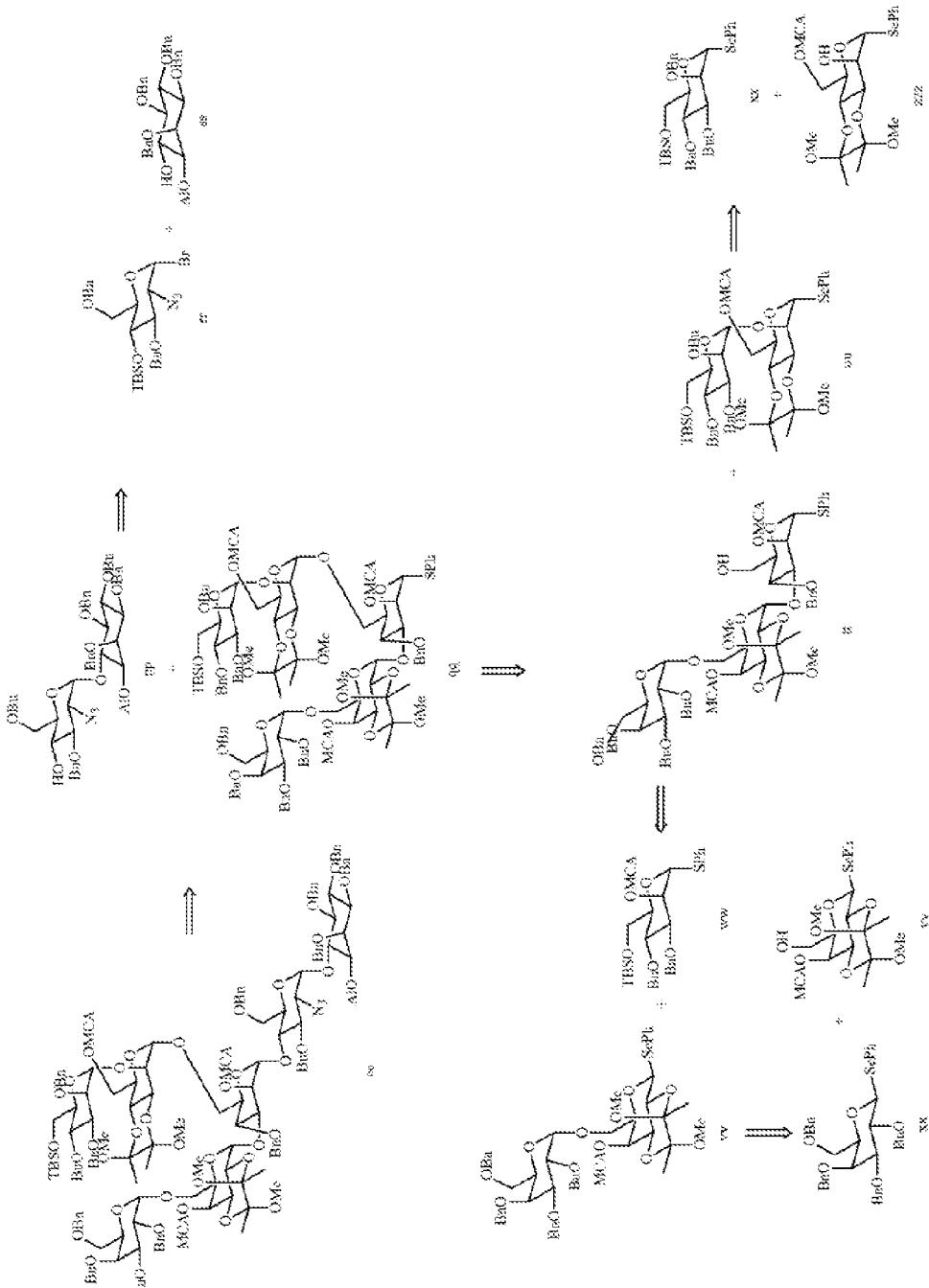
FIG. 5 depicts a retrosynthesis from Lay et al. *Chem. Eur. J.* 2000, 6, 172.

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Solution Phase Synthesis of a GPI Malaria Toxin for Use as a Vaccine

The malaria parasite is a formidable opponent for the human immune system. It proceeds through four distinct life cycles during the course of an infection, displaying different antigens to the immune system at each stage. Over 5000 proteins are displayed as the parasite changes from sporozoite to gametocyte. Therefore, a vaccine based on a protein found on the surface of sporozoites is ineffective once the parasite differentiates into a gametocyte. This stands in contrast to bacteria and viruses, where a consistent coating of antigens is displayed to the cells of the immune system.

Repeated exposure to the parasite over time (as the result of repeated infection), or infection with weakened sporozoites can both lead to antibody-based protection against infection. The former is called naturally acquired immunity (NAI), while the latter is referred to as the attenuated sporozoite model.[13] It is known that adults in malaria endemic areas can have parasites in their bloodstream yet be asymptomatic (i.e. they are naturally immune). If purified antibodies from the blood of these individuals are transferred to children who have high parasite loads, the parasite load is diminished, and the child is protected from subsequent infection. The attenuated sporozoite model is based on the observation that infection with sporozoites from mosquitoes irradiated with UV light does not lead to infection Rather, individuals vaccinated with these attenuated sporozoites are protected against subsequent infections for up to 9 months.

These two models are the main tenets behind modern vaccine design, and have led to four main schools of thought regarding vaccines: anti-infection, anti-transmission, anti-growth rate, and anti-toxin. In the case of malaria, these treatments all target the parasite at a different stage of its life cycle—the first three have defined protein targets derived from the cell surface of the parasite, while the last targets a toxin released following parasite replication. The limitation of the first three strategies are their specificity and inherent ineffectiveness once the parasite differentiates past the targeted life cycle stage. The parasite is versatile, and has shown the ability to vary its surface coating over time, rendering a previously effective vaccine useless. Anti-infection, -transmission, and -growth vaccine approaches are greatly aided by the bounty of information known about proteins on the cell surface of the parasite. The anti-toxin strategy has the advantage that the target appears to be invariable.[14] Neutralization of the toxin would work regardless of the protein coating on the surface of the parasite.

Figure 6:
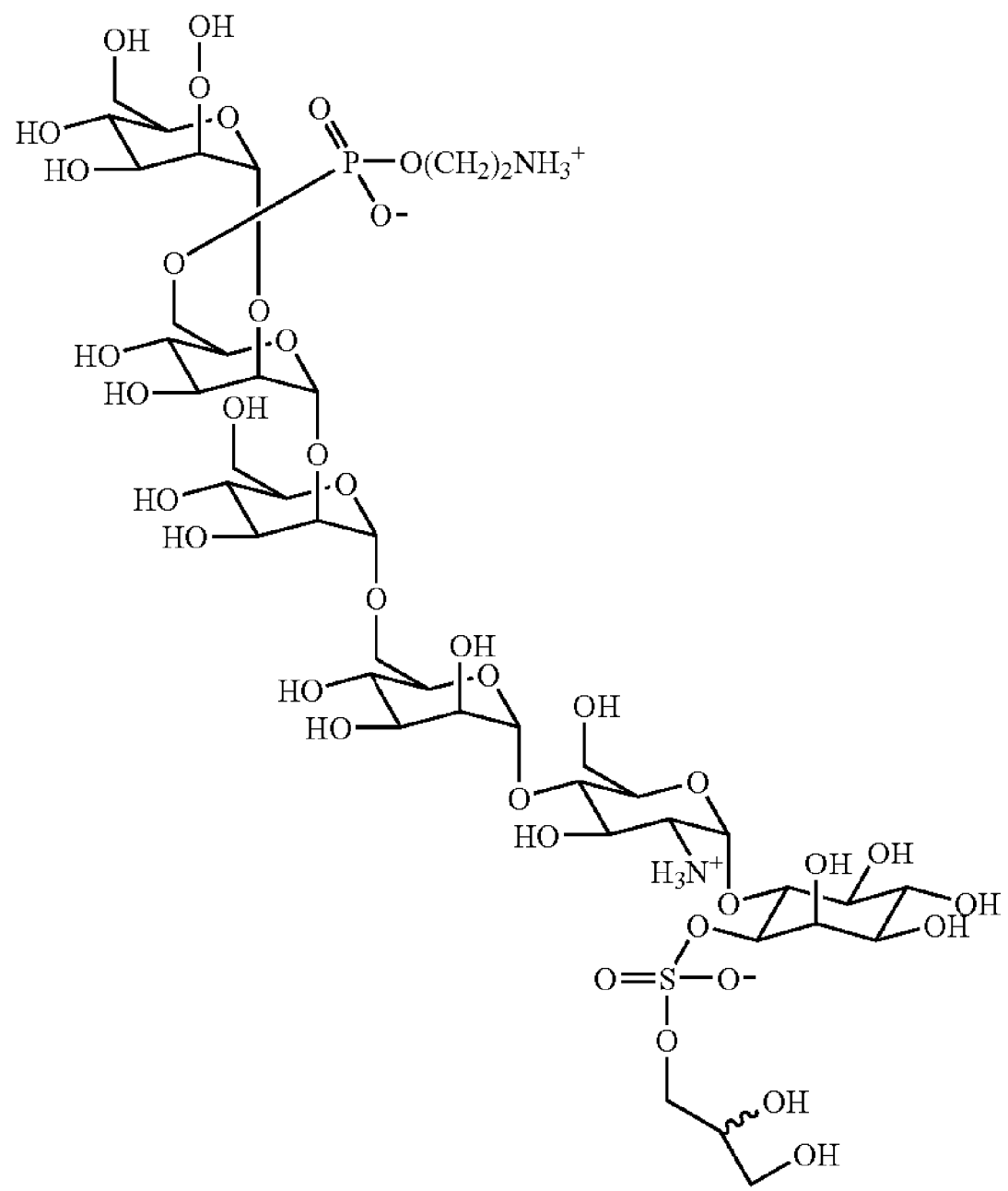
FIG. 6 depicts a *P. falciparum* GPI (1).

Anti-toxin vaccines target the toxin that is released following erythrocyte rupture, and represent the second form of protection against blood-stage parasites. Release of this toxin is thought to initiate an inflammatory cascade in the host, resulting in the release of harmful cytokines such as tumor necrosis factor (TNFα). An effective anti-toxin vaccine would prevent the inflammatory cascade in the host through antibody sequestration and neutralization of the parasite toxin; as the cascades caused by the toxin are necessary for parasite success, evolved resistance should be blunted. A GPI of parasite origin (1) was recently isolated that induced several of the pathological effects associated with severe malaria and was thus a candidate toxin (FIG. 6).[15] Purified GPI induced TNFα expression and NO output in macrophages, both of which occur during real infections and lead to clinical manifestations of malaria.

In addition, a recent study found that adults with resistance to malaria had high levels of persistant anti-GPI antibodies, while susceptible children had low levels or lacked these protective anti-GPI antibodies.[16] The absence of anti-GPI antibody response correlated with malaria specific anemia and fever, suggesting that anti-GPI antibodies played a major protective role against malaria.

Figure 7:
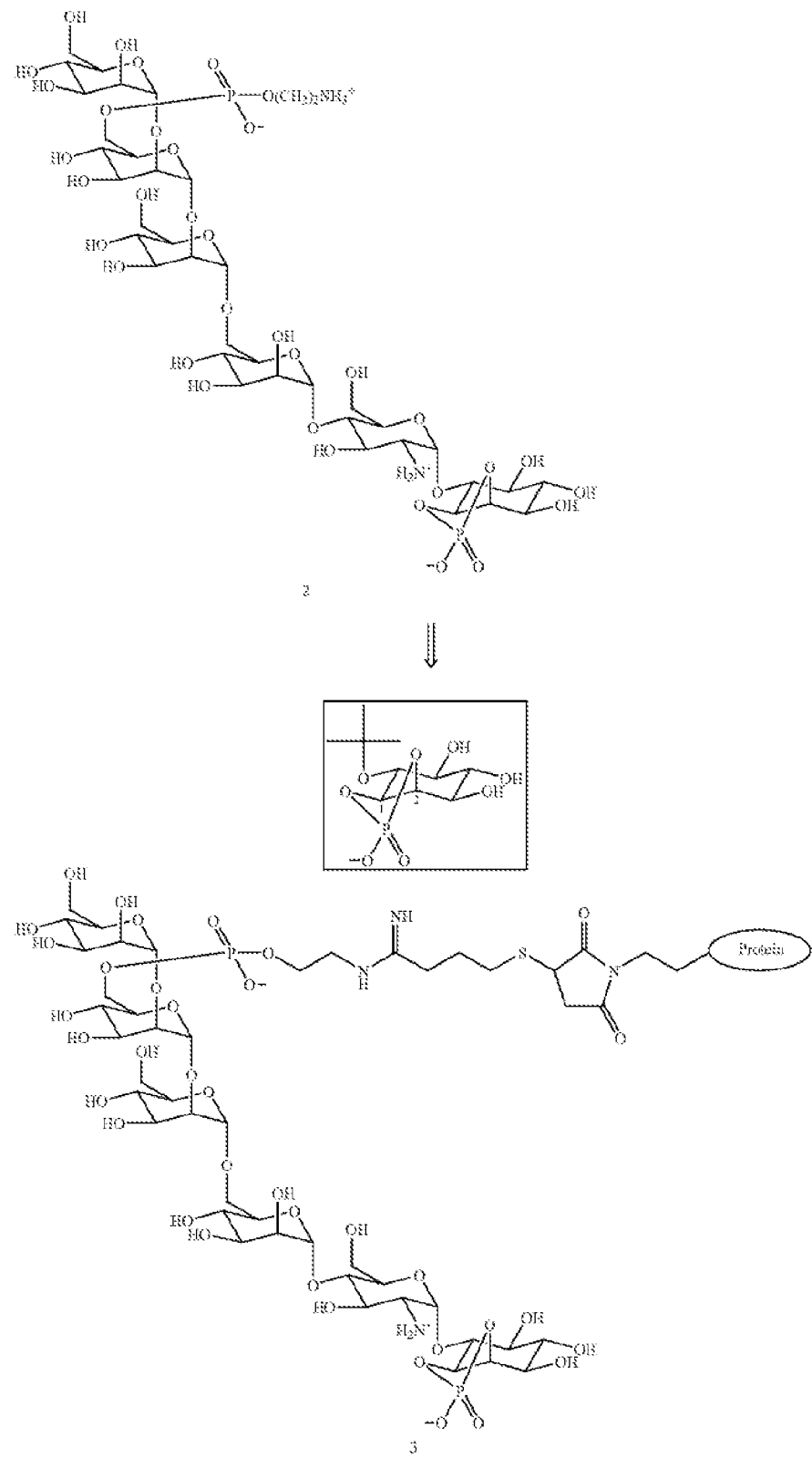
FIG. 7 depicts a potential GPI anti-toxin vaccine 3.

What remained to be established was if an anti-toxin vaccine based on the structure of the isolated GPI would reduce pathogenesis or fatalities in any disease condition. Anti-toxin vaccines have been discussed for some time,[17] but never reduced to practice. We sought to determine whether immunization with GPI oligosaccharide fragment 3, prepared by chemical synthesis, could prevent pathology and fatalities in a rodent model of severe malaria (FIG. 7).

One facet of the vaccine design deserves mention: our proposed synthetic fragment 2 differs from the authentic malarial GPI1 in the phosphorylation of the inositol ring.

Selective installation of a phosphate on the 1-position of an inositol ring in the course of a GPI synthesis requires preparation of an inositol building block that is orthogonally protected on the 1-position (i.e. leading to 1). This is not a trivial operation, and the search for new methods to solve this problem has been the subject of intense research.[18] We chose to install a cyclic phosphate on the 1,2-position on potential vaccine precursor 2 rather than focusing on developing new methodology.

GPI Synthesis

Figure 8:
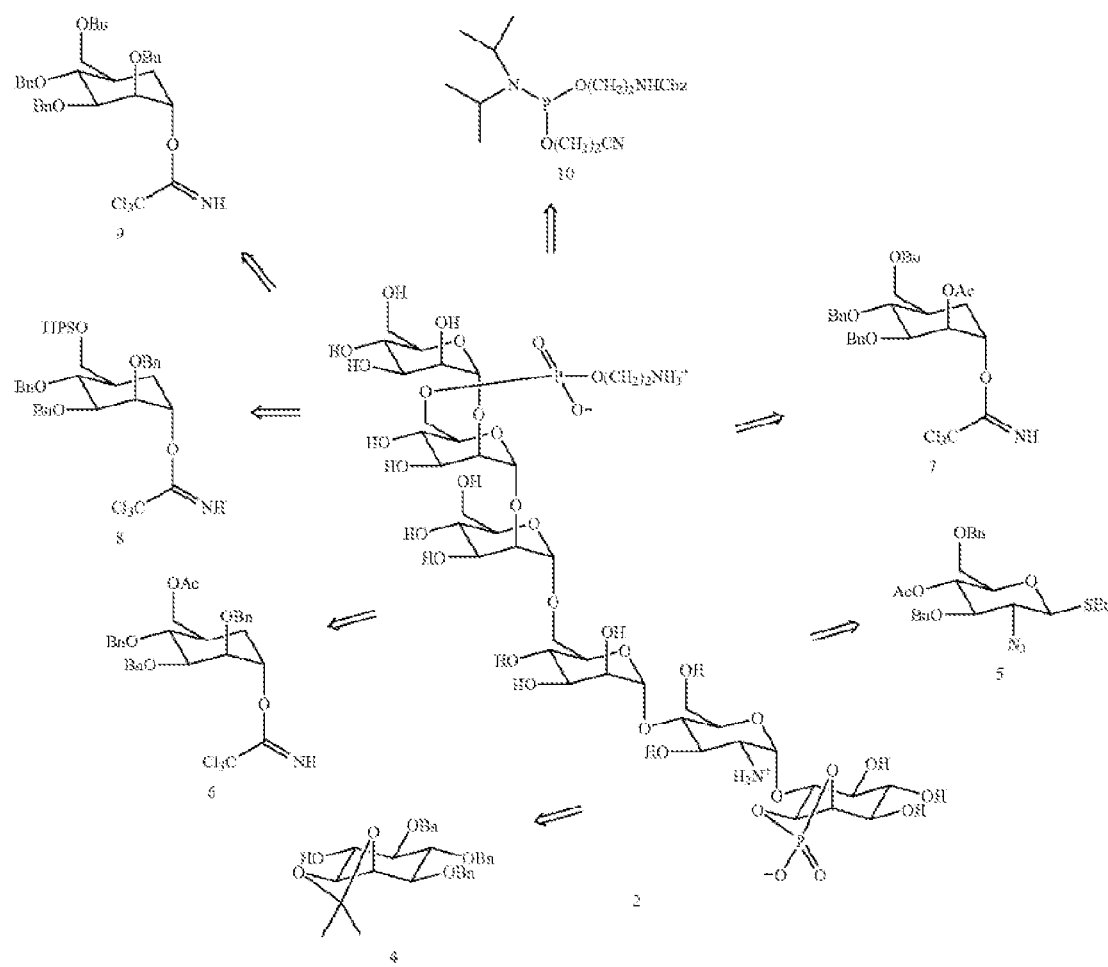
FIG. 8 depicts a retrosynthesis of GPI 2.

We developed a synthetic route for 2 that employed five differentially-protected glycosyl donors, one inositol and one phosphoramidite building block (FIG. 8). While the initial synthesis of 2 was carried out in solution, our ultimate goal was automated solid-phase synthesis,[19] which helped guide our selection of protecting groups and glycosyl donors.

Figure 9:
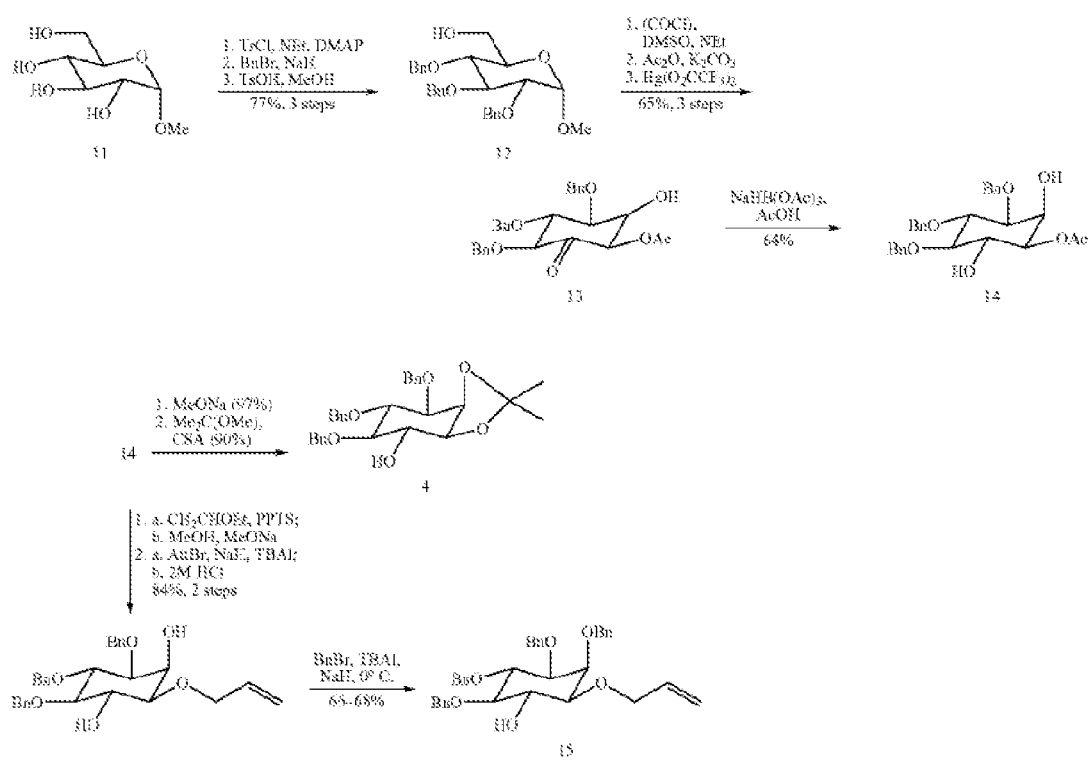
FIG. 9 depicts a synthesis of inositol acceptors.

Building blocks 4,[20] 7,[7a] 9,[7a] and 10[7b] were prepared following known procedures, while thiodonor 5 and imidates 6 and 8 required novel syntheses. The route to myo-inositol acceptor 4 (FIG. 9) followed literature precedent.[20a] Selective mono tritylation[21] of the methyl-α-D-glucopyranoside 11 followed by benzylation and removal of the temporary trityl ether gave 12. Swern oxidation,[22] formation of a mixture of isomeric enol acetates ($Ac_2O$, $K_2CO_3$), and Ferrier reaction[23] under the catalysis of mercuric acetate provided hydroxy-ketone 13 in 53% for 3 steps. Internal-delivery reduction with sodium triacetoxyborohydride gave the anti diol in 64% yield. Cleavage of the acetate with NaOMe/MeOH provided a known triol,[23] and protection of the cis alcohols as their isopropylidene under thermodynamic control gave acceptor 4. Alternatively, protection of the hydroxyls of diol 14 as ethoxyethyl ethers, replacement of acetyl by allyl, and removal of the acetals allowed production of differentiated acceptor 15. This molecule should allow use of non-cyclic phosphodiesters.

Figure 10:
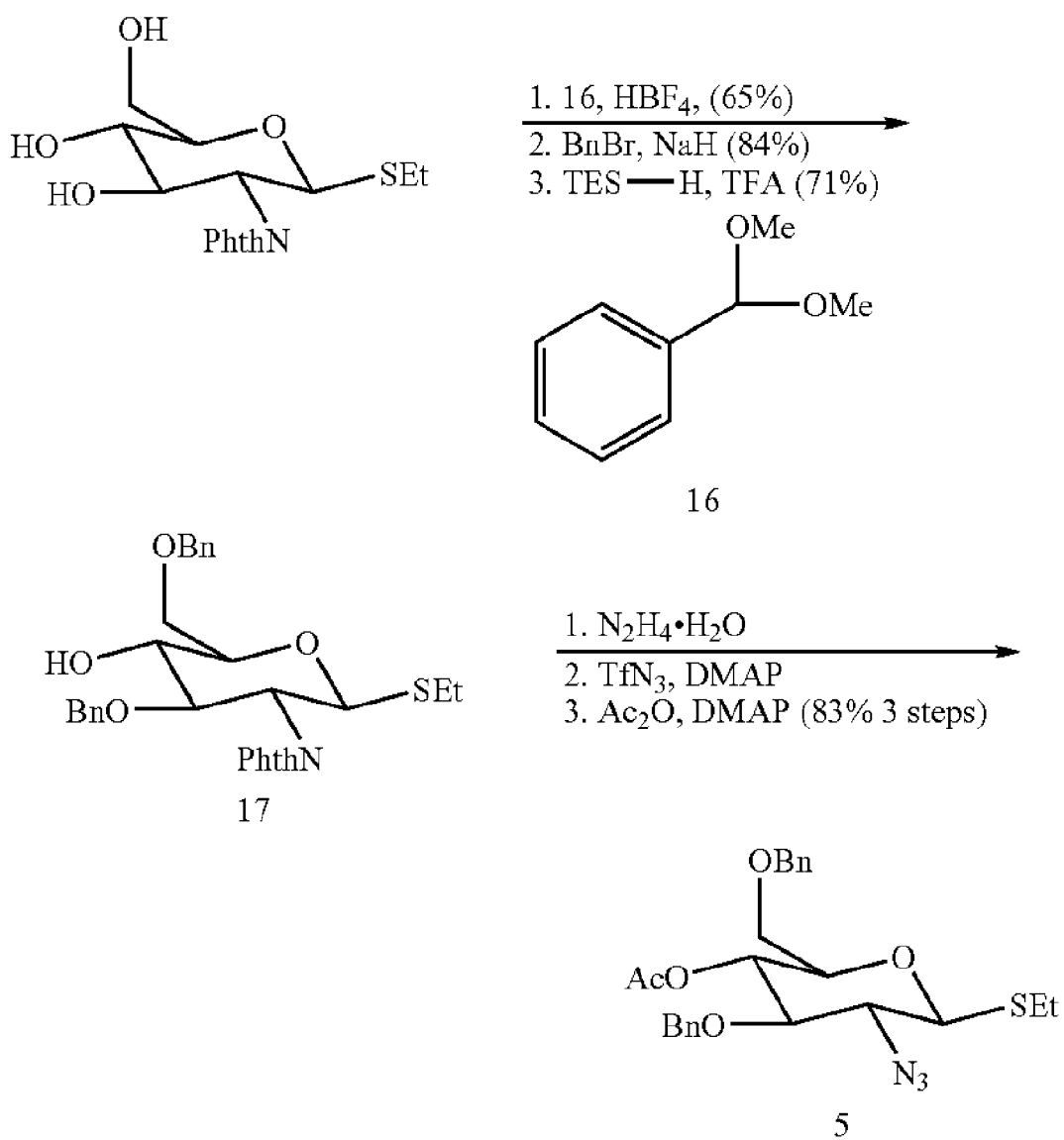
FIG. 10 depicts a synthesis of a glucosamine building block.

For preparation of glucosamine building block 5, we started from known phthalimide-protected triol[25] (FIG. 10). Protection of the 4,6-diol as a benzylidene ring proceeded under the agency of tetrafluoroboric acid[26] in 65% yield, followed by benzylation of the remaining alcohol (84% yield). Regioselective opening of the benzylidene using triethylsilane and trifluoroacetic acid[27] afforded 3,6 di-benzyl thioglycoside 17 in 71% yield. The next transformation en route to the desired donor was an amine protecting group switch, from phthalamide to azide. Phthlamide groups are not compatible with the conditions used for cleavage of acetate esters (vide infra), and would also favor an undesirable β-linkage in the initial coupling event. Cleavage of the phthlamide with hydrazine monohydrate was followed by treatment of the crude amine with freshly prepared triflic azide.[28] Treatment of the crude product with acetic anhydride and DMAP followed by chromatography provided thiodonor 5 in 83% yield for the three steps.

Figure 11:
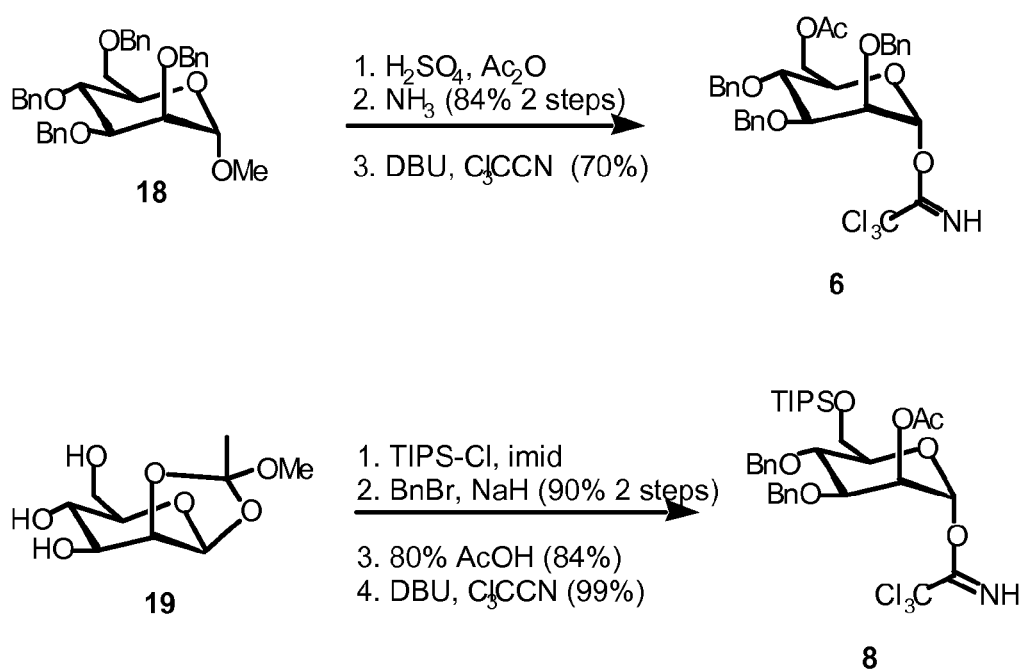
FIG. 11 depicts a synthesis of trichloroacetimidate building blocks.

The synthesis of imidate 6 began with per-benzylated methyl mannopyranoside 18[29] (FIG. 11). Conversion of both the anomeric methoxy group and the 6-O-benzyl group to acetates was accomplished using concentrated sulfuric acid with acetic anhydride as solvent.[30] The anomeric acetate was cleaved using ammonia, and the resulting lactol was converted into trichloroacetimidate[31] 6 using trichloroacetonitrile and catalytic DBU. The additional degree of orthogonality required of building block 8 necessitated the use of orthoester 19.[32] Regioselective protection of the 6-position as a silyl ether was followed by dibenzylation in 90% yield over two steps. Aqueous acetic acid was employed for the opening of the orthoester (82%), resulting in formation of a 2-O-Ac anomeric lactol. Preparation of imidate 8 proceeded in high yield using trichloroacetonitrile and DBU.

Figure 12A:
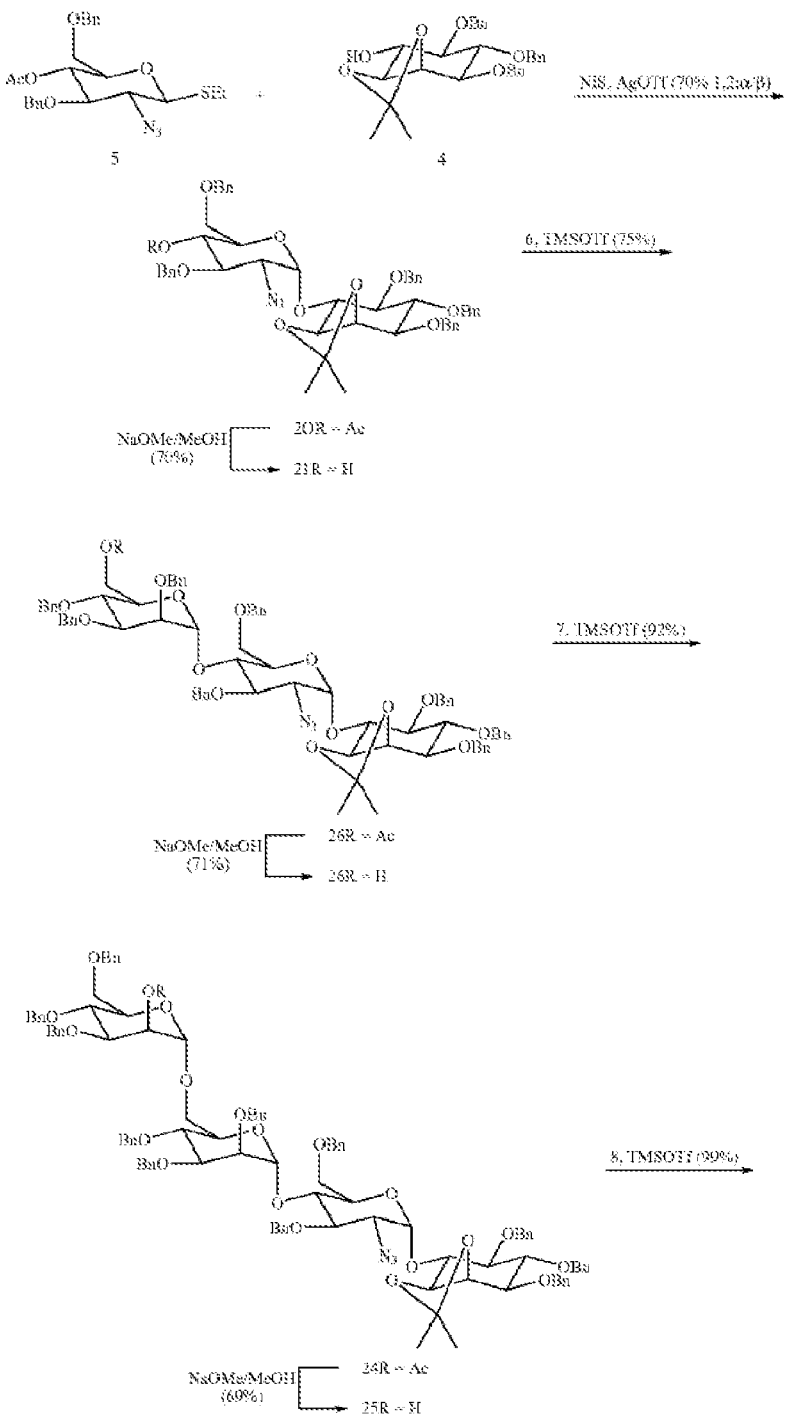

The first glycosidic linkage to be formed was the difficult union between thiodonor 5 and inositol derived acceptor 4 (FIG. 12A and FIG. 12B). Activation with N-iodosuccinimide/silver triflate provided pseudo-disaccharide product 20 in 70% yield as a separable 1.2:1 mixture in favor of the desired α-isomer. Deprotection with sodium methoxide removed the acetyl group to give acceptor 21, which was then coupled to trichloroacetimidate 6 in 75% yield. Cleavage of the acetate of the resultant pseudo-trisaccharide 22 provided acceptor 23, which was positioned for the next coupling with building block 7. This coupling proceeded in high yield (92%) and furnished exclusively α-linked pseudo-tetrasaccharide acceptor 25 following deprotection with sodium methoxide in methanol. Coupling of acceptor 25 and donor 8 proceeded in excellent yield under slightly milder conditions (TBSOTf), and was followed by deprotection to give pseudo-pentasaccharide acceptor 27. The addition of a terminal mannose subunit proceeded in high yield (84%) with donor 9, but afforded a mixture of anomers that were inseparable by silica gel chromatography. Deprotection of the isopropylidene acetal[7b] on the inositol ring proved to be a difficult transformation, providing mixtures of starting material, desired diol 29, and triol arising from concomitant TIPS cleavage. After multiple recycling steps and tedious column chromatography 29 was isolated in a modest yield of 67%, albeit still as a mixture of isomers from the 5+1 coupling event.

Figure 13:
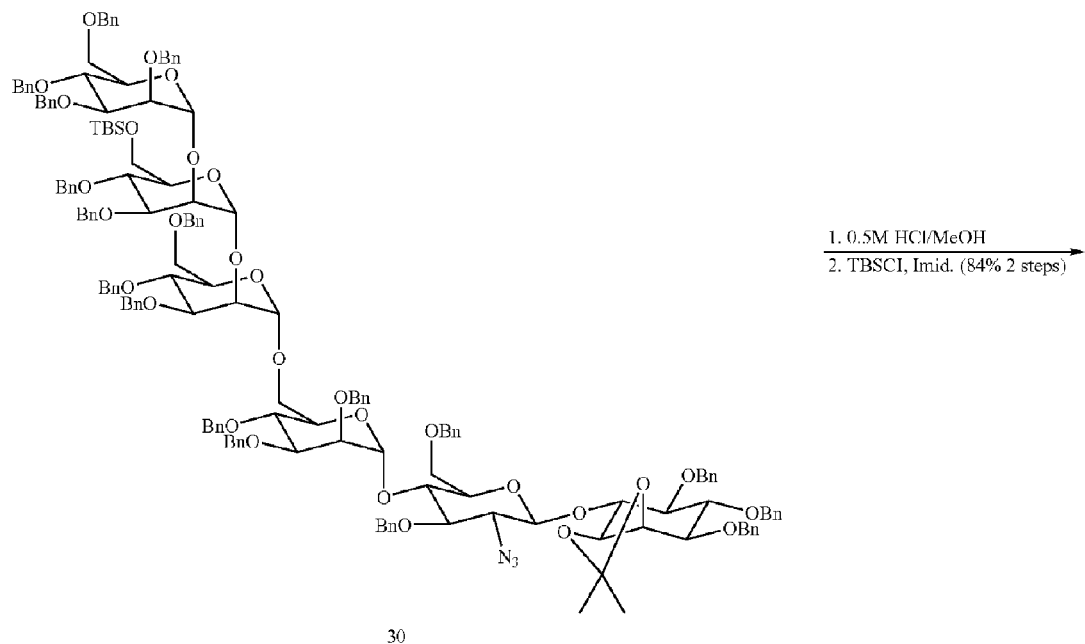
FIG. 13 depicts alternative hydrolysis conditions.
Figure 13:
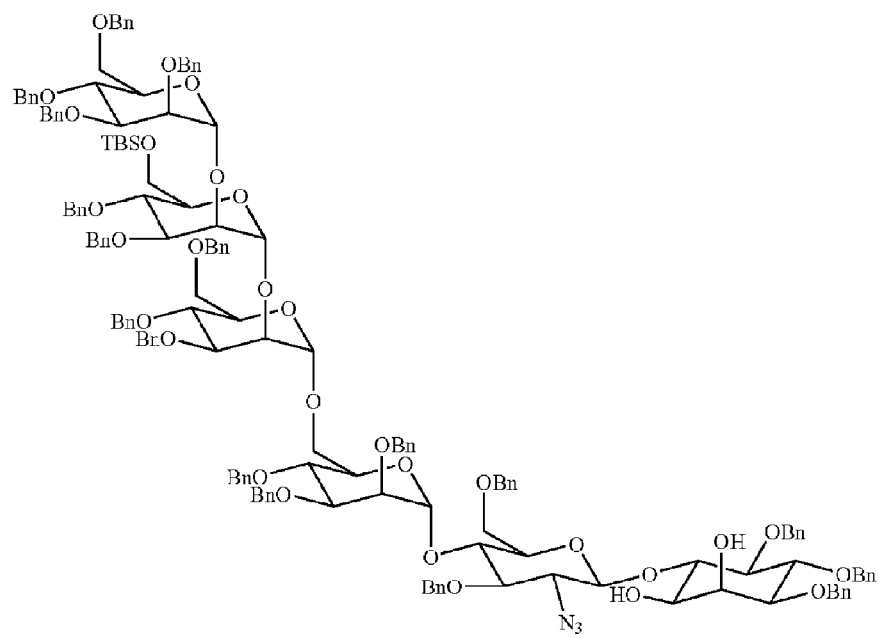

The difficulties encountered in the final coupling event and problematic hydrolysis of the isopropylidene group prompted us to explore an alternate route to a protected diol such as 29. Replacing per-benzylated donor 9 with 2-acetate donor 7 would be a straightforward solution to the first problem. Following saponification and benzylation the protected pseudo-hexasaccharide should be isolable as a single isomer. For a solution to the sluggish hydrolysis reaction, we turned to an earlier GPI synthesis by Frick et al.[10a] Instead of trying to prevent concomitant silyl ether cleavage in the course of acetal cleavage, the authors had hydrolysed all acid labile groups (FIG. 13). After workup, the silyl ether had been regioselectively re-installed on the primary alcohol to give 31.

Figure 14:
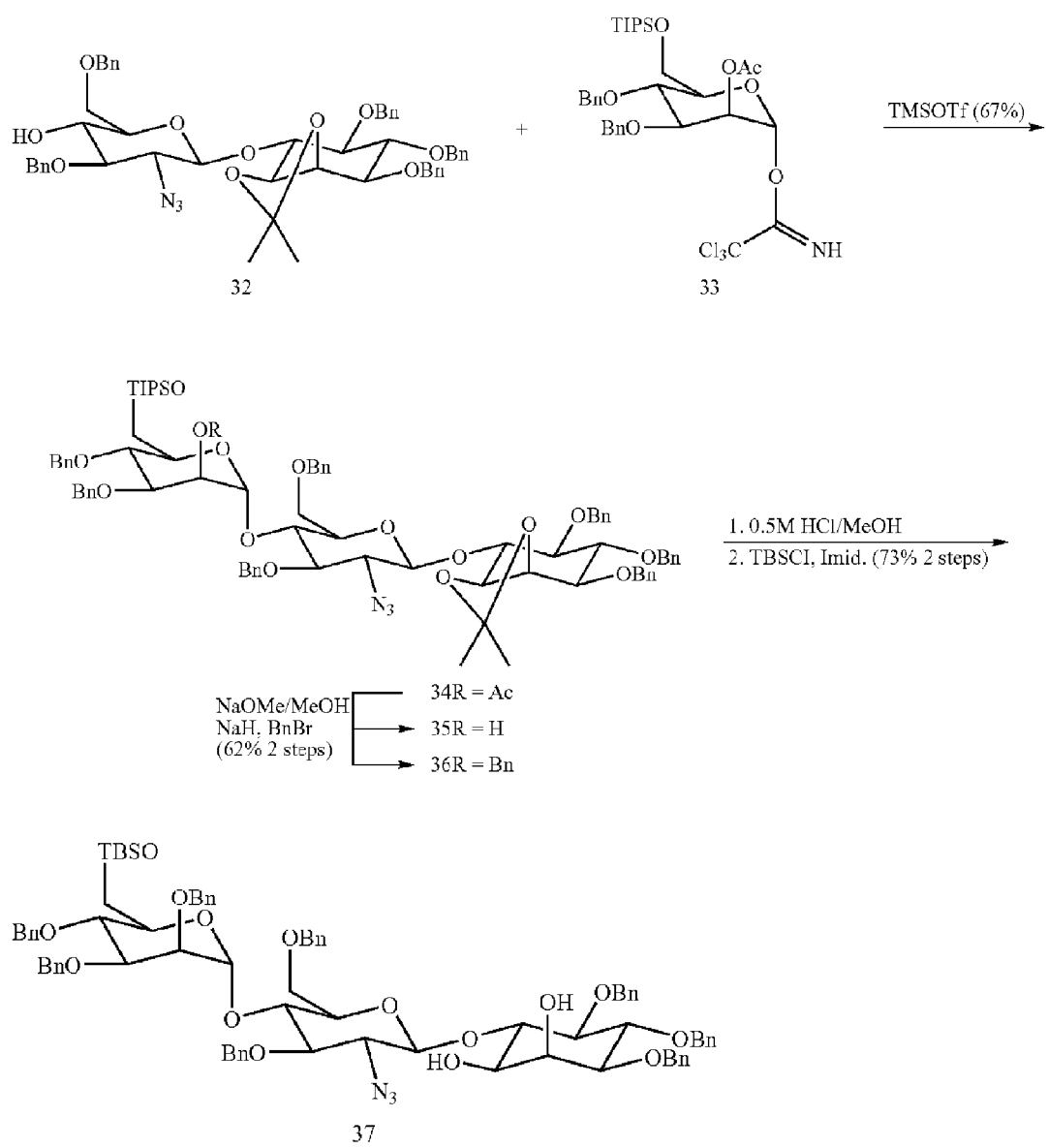
FIG. 14 depicts a model trisaccharide synthesis.

A model trisaccharide bearing the appropriate functionality was constructed to examine the hydrolysis reaction (FIG. 14). Disaccharide acceptor 32 was reacted with donor 33 to give a 67% yield of desired pseudo-trisaccharide 34. Saponification and benzylation proceeded smoothly in a combined 62% yield for the two steps, and set the stage for the model hydrolysis. Hydrolysis of the TIPS ether and isopropylidene groups was accomplished using 0.5 M HCl in methanol over 12 hours, followed by alkaline workup. Following reaction with TBS-Cl and imidazole (imid.), a 73% yield of desired diol 37 was isolated. The good yield of the model reaction coupled with its operational simplicity prompted us to apply these hydrolysis conditions.

Figure 15A:
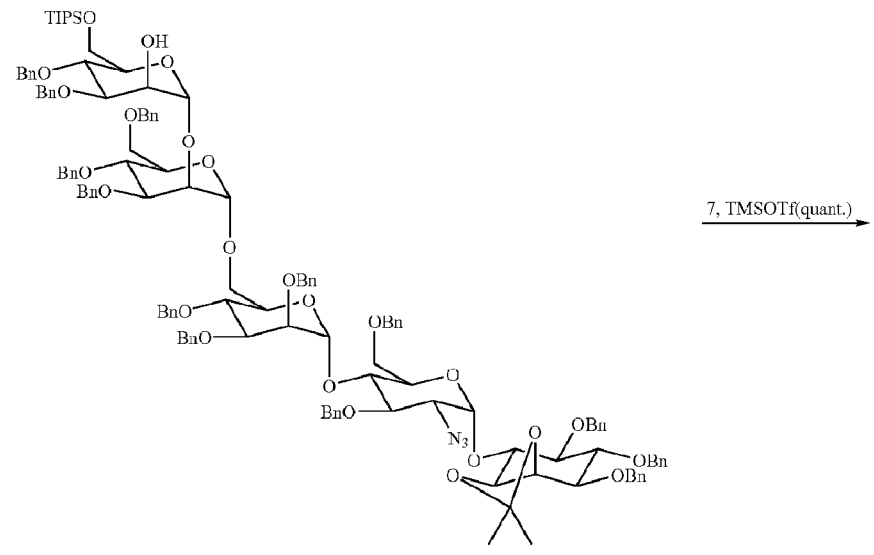
Figure 15A:
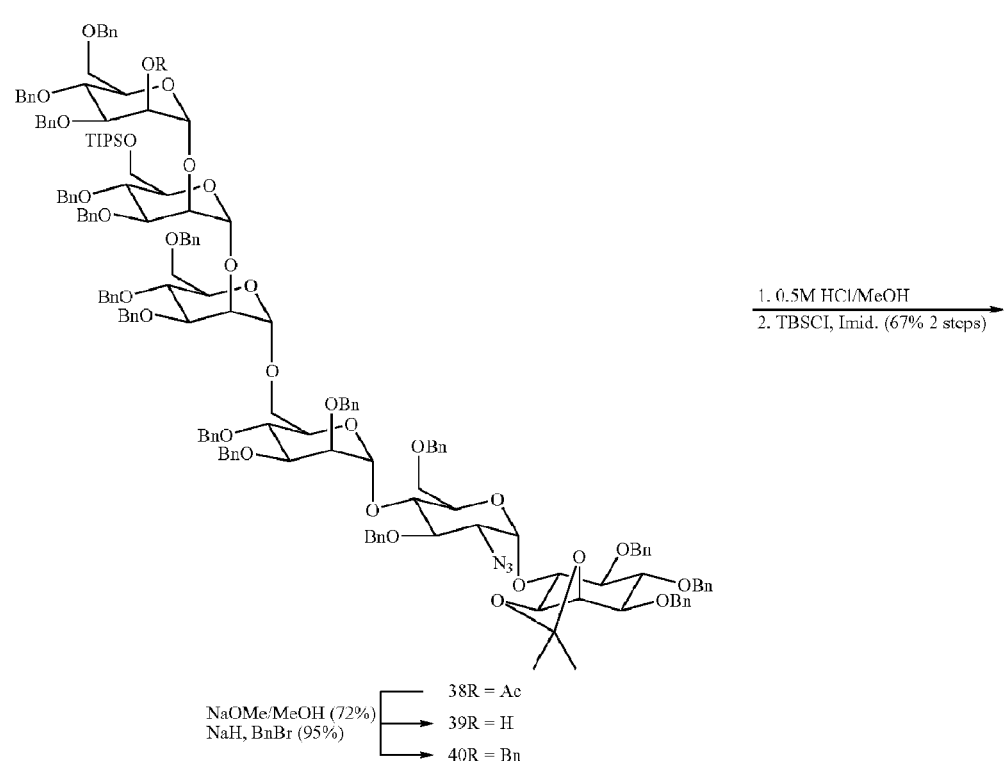

Starting from pseudo-pentasaccharide acceptor 27, 2-Ac donor 7 was installed to give a quantitative yield of the desired pseudo-hexasaccharide as a single isomer (FIG. 15A and FIG. 15B). The structure of 38 was confirmed using several 2D-NMR experiments (COSY, HSQC, HMBC, TOCSY).[33] Deprotection gave a 72% yield of the pseudo-hexasaccharide 39 before benzylation afforded compound 40 in 96% yield. Following the conditions used for our model trisaccharide, hydrolysis and re-installation of the silyl ether proceeded smoothly to afford 67% of 41. Using a mixture of methyldichlorophosphate in pyridine,[34] pseudo-hexasacharide cyclic phosphate could be isolated after acidic workup. The crude material was subjected to silyl ether cleavage using TBAF to give a 70% yield of 42.

Figure 16:
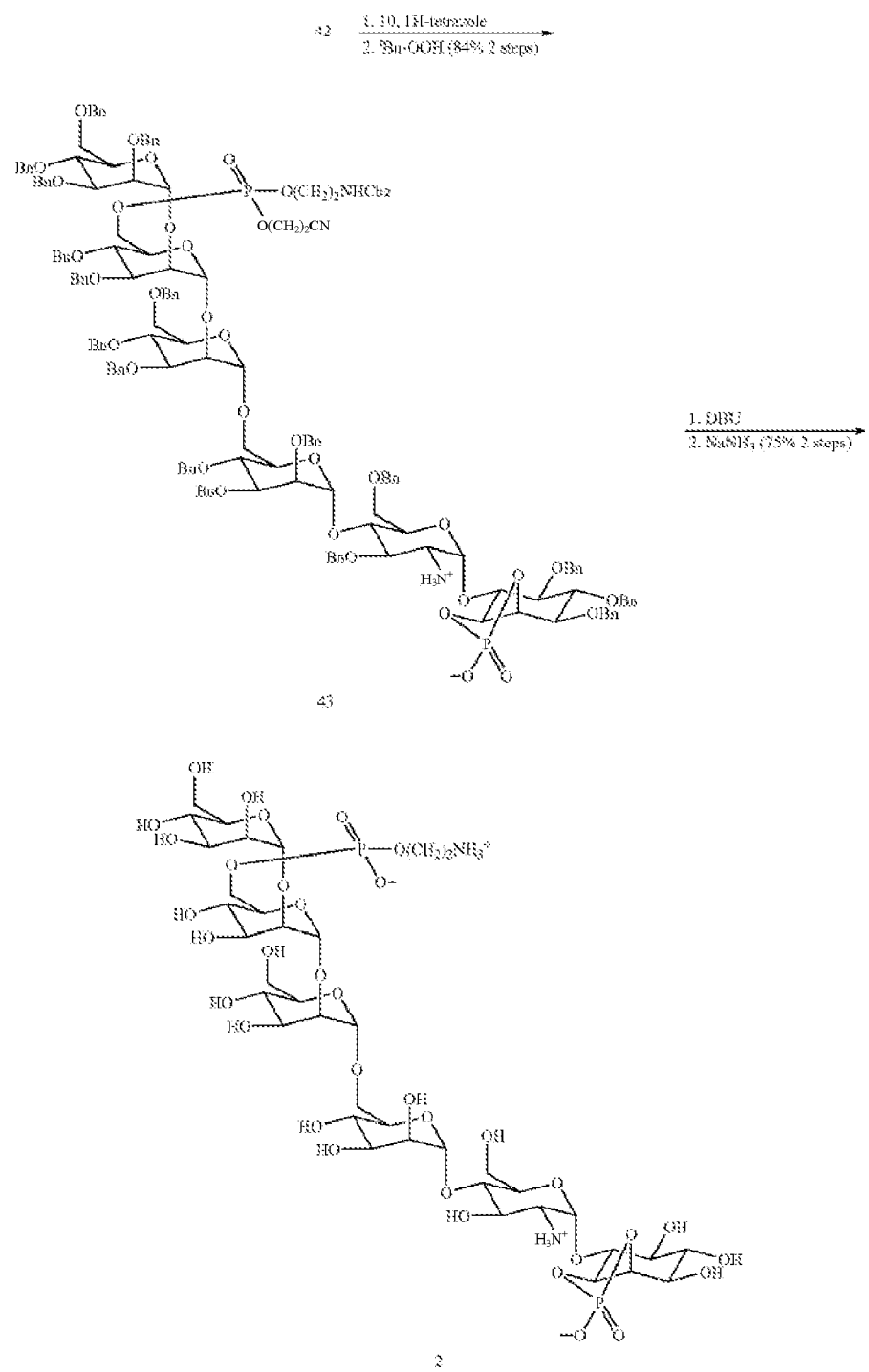
FIG. 16 depicts a synthesis of target 2.

Reaction with phosphoramidite 10[7b] and oxidation provided bis-phosphate 43 as a mixture of diastereomers. DBU was used to cleave the -cyanoethoxy blocking group, and removal of the benzyl ethers, benzyloxy (Cbz) carbamate, and azide was accomplished in a single step with Na/NH$_3$ to afford desired GPI 2. See FIG. 16. The final product was characterized by $^1$H, and $^{31}$P NMR, as well as by MALDI-TOF mass spectrometry.

Preparation and Evaluation of Anti-Toxin Vaccine 3

Figure 17:
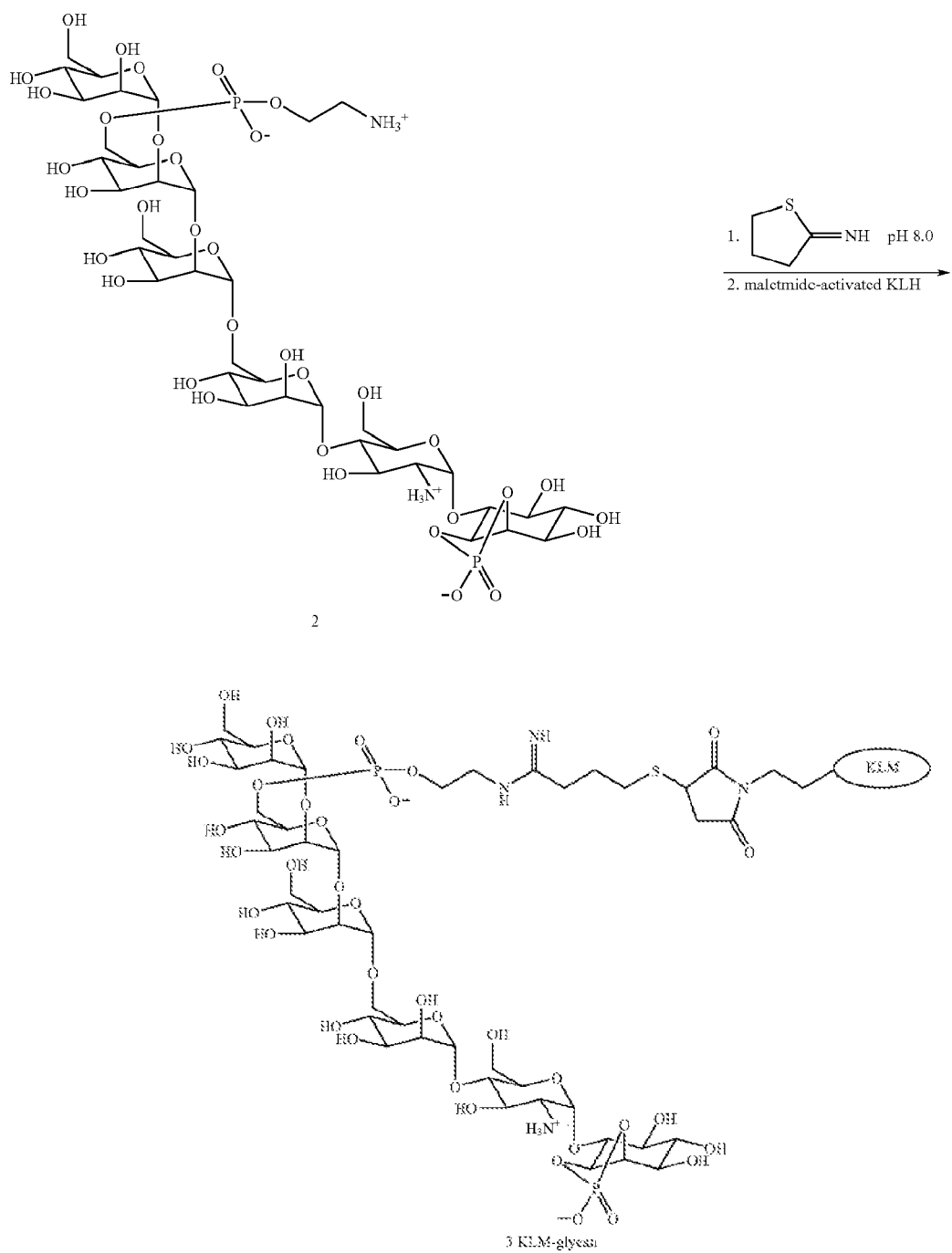
FIGS. 17 and 18 depict a preparation of immunogen and sham.
Figure 18:
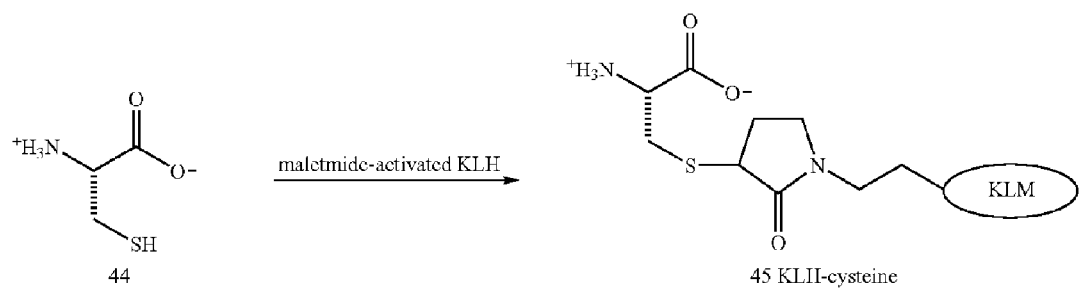

To prepare an immunogen, the synthetic GPI glycan 3 was treated with 2-iminothiolane (FIG. 17) to introduce a sulfhydryl at the primary amine within the ethanolamine phosphate, desalted, and conjugated to maleimide-activated ovalbumin (OVA, in molar ratio 3.2:1) or Key-Hole Limpet Haemocyanin (KLH, in molar ratio 191:1), and used to immunize mice. The synthetic malarial GPI glycan was immunogenic in rodents. Antibodies from KLH-glycan 3 immunized animals gave positive IgG titres against OVA-glycan but not sham-conjugated OVA-cysteine 45 containing identical carrier and sulfhydryl bridging groups (FIG. 18). No reactivity to GPI glycan was detected in pre-immune sera or in animals receiving sham-conjugated KLH. More significantly, antibodies raised against synthetic *P. falciparum* GPI glycan bound to native GPI as judged by several methods.

Figure 19:
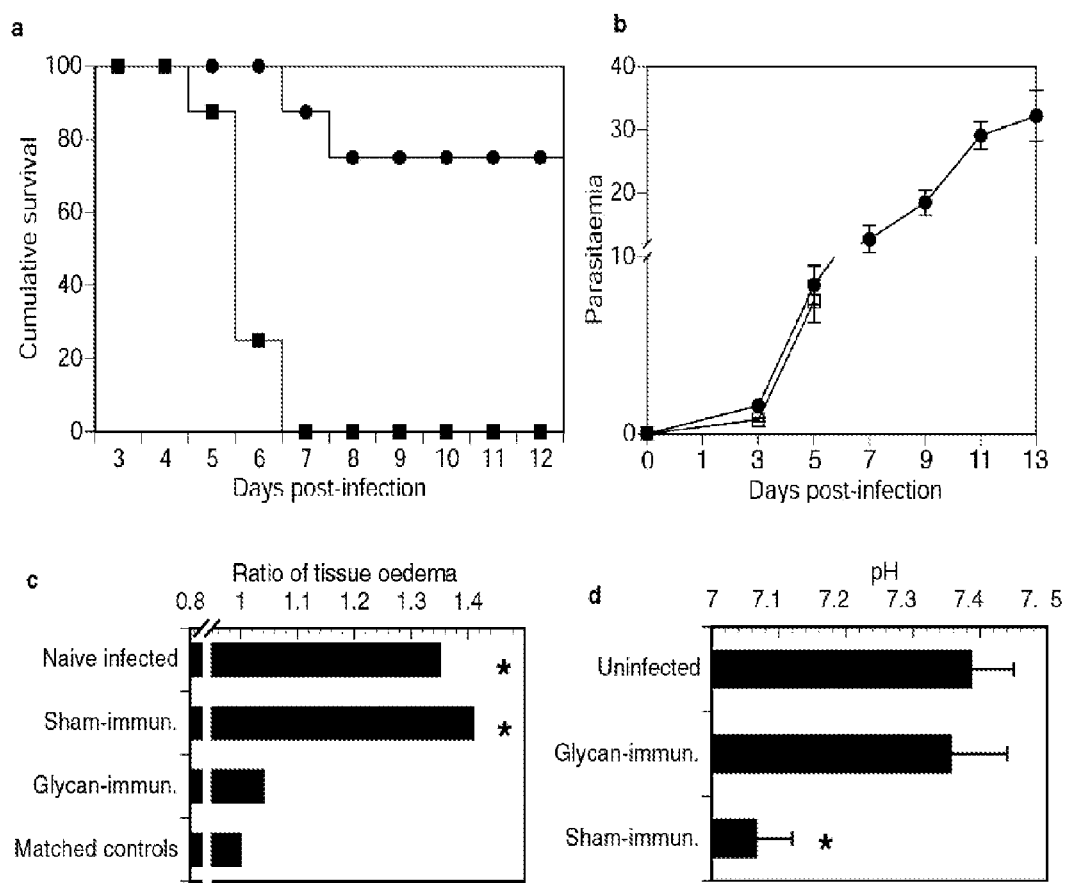
FIG. 19 shows that immunization against the synthetic GPI glycan substantially protects against murine cerebral malaria, pulmonary edema and acidosis. a) Kaplan-Meier survival plots, and b) parasitaemias, to 2 weeks post-infection, of KLH-glycan-immunized (closed circles) and sham-immunized (open squares) mice challenged with P. berghei ANKA; c) As an index of pulmonary edema, the ratio of wet weight to dry weight of lungs from KLH-glycan-immunized and sham-immunized animals at day 6 post-infection are expressed as a proportion of the lung wet:dry weight ratio of age/sex matched uninfected controls; and d) pH of serum drawn at day 6 from uninfected and P. berghei-ANKA-infected immunized and sham-immunized donors.

The murine *P. berghei* ANKA severe malaria model has salient features in common with the human severe and cerebral malaria syndromes and is the best available small animal model of clinically severe malaria. To determine whether anti-GPI immunization prevents systemic and cerebral pathogenesis in this pre-clinical model, C57B16 mice primed and twice boosted with 6.5 µg KLH-glycan (0.18 µg glycan) or KLH-cysteine in Freund's adjuvant were challenged with *P. berghei* ANKA, and the course of disease monitored (FIG. 19A). 100% of both sham-immunized and naïve control mice died within 5-8 days. There were no differences between naïve and sham-immunized mice indicating exposure to carrier protein alone in Freund's adjuvant does not influence disease rates. In contrast, mice immunized with synthetic *P. falciparum* GPI glycan coupled to KLH were substantially protected against cerebral malaria, with significantly reduced death rates (75% survival, FIG. 19A). In four separate additional experiments, results over the range of 58.3-75% survival over this time-period in vaccine recipients (n=50 total) vs. 0-8.7% survival in sham-immunized controls (n=85) were obtained. Parasitaemias were not significantly different between test and control groups in these experiments, demonstrating that prevention of fatality by anti-GPI vaccination does not operate through effects on parasite growth rates (FIG. 19B).

Severe malaria in both humans[35] and rodents[36] may be associated with additional organ-specific and systemic symptoms, including pulmonary edema and serum acidosis. Our collaborators sought to determine whether anti-GPI vaccination protects against these additional non-cerebral disease syndromes in mice. Both sham-immunized and naive individuals developed pronounced pulmonary edema by day 6 post-infection, as measured by lung dry:wet weight ratios, and this symptom was markedly reduced in vaccine recipients (FIG. 19C). Similarly, whereas sham-immunized and unimmunized mice developed significant acidosis as shown by reduced blood pH at day 6 post-infection, in vaccinated mice blood pH was maintained at physiological levels (FIG. 19D). Immunizing against GPI clearly prevented the development of pulmonary edema and acidosis as well as cerebral malaria in *P. berghei* infection.

The findings of the mouse study demonstrated that GPI is the dominant endotoxin of *P. falciparum* and *P. berghei* origin. A synthetic GPI oligosaccharide coupled to carrier protein was immunogenic and provided significant protection against malarial pathogenesis and fatalities in a preclinical rodent model. It is therefore possible that GPI contributes to life-threatening disease in human malaria. The data suggest that an anti-toxin vaccine against malaria might be feasible and that synthetic fragments of the *P. falciparum* GPI may be developed further toward that goal.

Automated Synthesis of GPIs

The mouse trials using anti-toxin vaccine 3 showed that synthetic GPI fragments are highly immunogenic when applied to malaria infection. The minimal structure required for an effective anti-toxin vaccine based on the malarial GPI was not defined. The rapid synthesis of GPI fragments for subsequent biological evaluation would be highly desirable, and could lead to a more potent anti-toxin vaccine. Application of our automated carbohydrate synthesizers to this problem seemed natural.

Figure 20A:
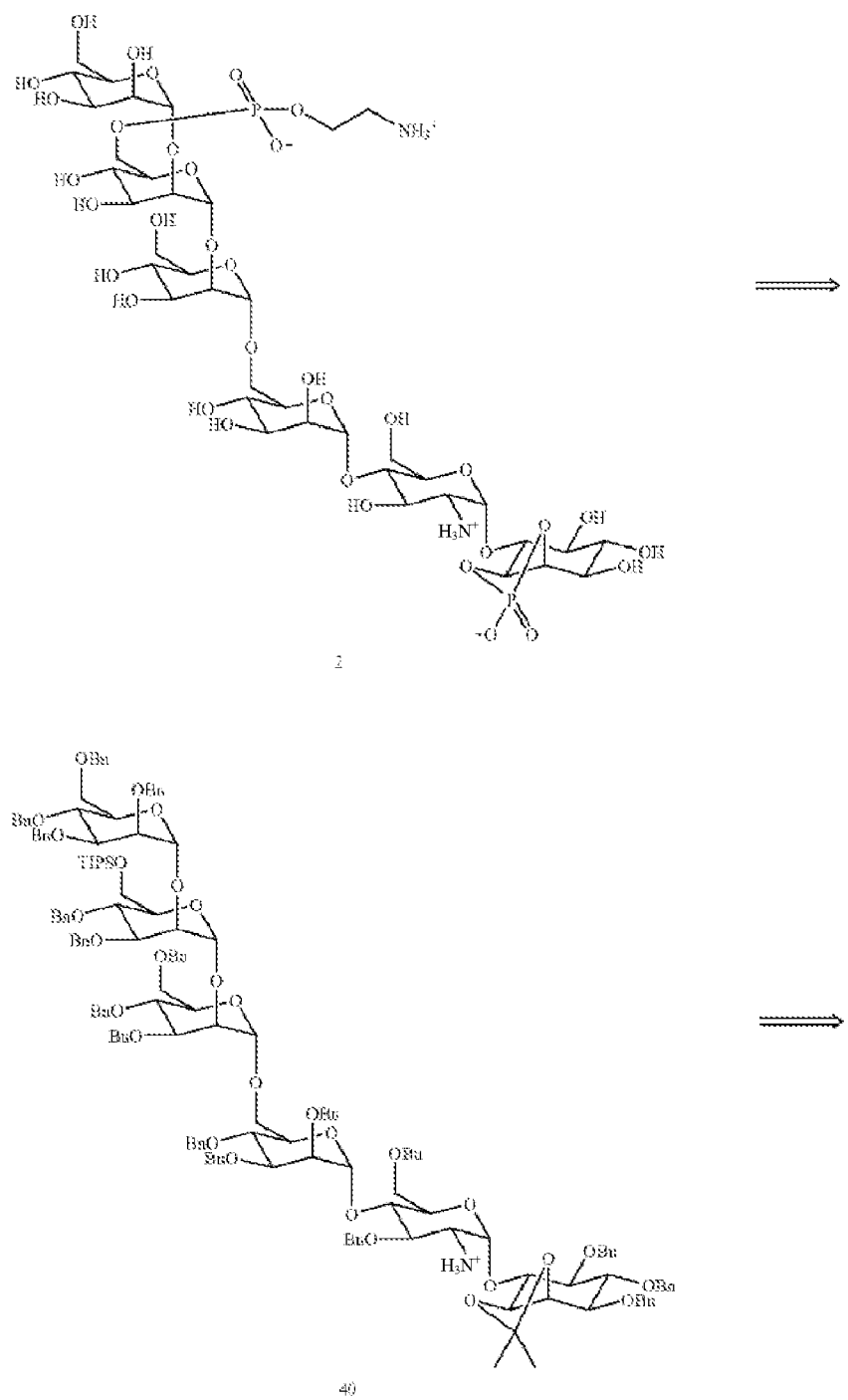

Using our solution phase synthesis as a guide, we contemplated the automated synthesis of 2. While it would be ideal to prepare the entire skeleton on solid-phase, the α-linkage between the inositol and glucosamine residues presented a serious impediment to a fully automated synthesis. Relatively few methods are available for the preparation of 1,2-cis glycosidic linkages.[37] Previous GPI syntheses addressed this problem by either separating mixtures of isomers, or utilizing completely α-selective coupling methods followed by protecting group manipulations.[38] Neither of these solutions was amenable to solid-phase, which led us to dissect GPI 2 into two fragments: a known disaccharide 21 not readily accessible on solid phase, and a tetra-mannosyl fragment (46) readily prepared using our automated solid-phase methodology (FIG. 20A and FIG. 20B). The two fragments could be joined using n-pentenyl glycoside (NPG) coupling methodology,[39] or via hydrolysis and conversion into tetrasaccharide trichloroacetimidate 47.

Figure 21:
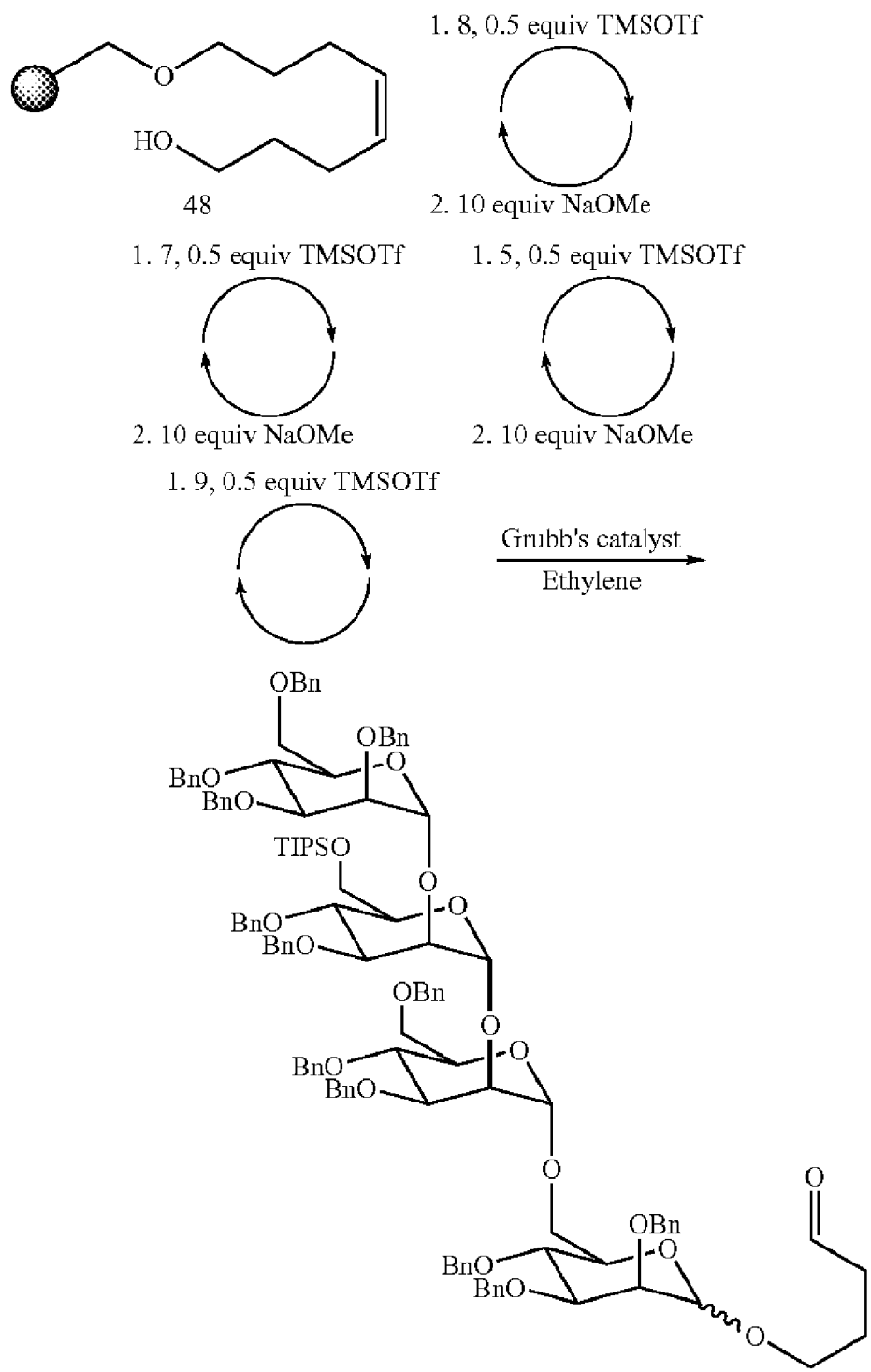
FIG. 21 depicts an automated synthesis of GPI 46.
Figure 23:
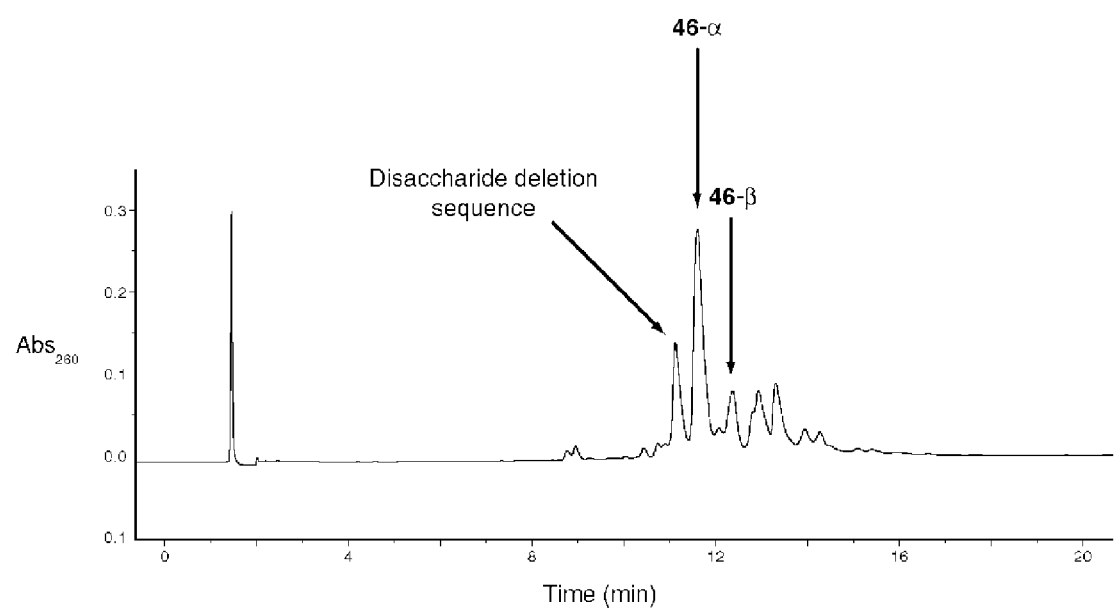
FIG. 23 depicts an HPLC analysis of automated synthesis of 46. Flow rate: 1 mL/min, 5→20% EtOAc/hexanes (20 min).

Tetrasaccharide 46 was accessed on solid-phase using four readily available trichloroacetimidate building blocks 6-9 (FIG. 21). The automated synthesis was carried out on a modified ABI 433A peptide synthesizer using octenediol-functionalized Merrifield resin 48. Each coupling cycle (FIG. 22) relied on double glycosylations to ensure high coupling efficiencies and a single deprotection event. Coupling of 6 to resin 48 using catalytic TMSOTf was followed by removal of the acetate ester upon exposure to NaOMe.

Based on a solution-phase model, we did not anticipate a selective coupling between donor 6 and the functionalized resin; the stereochemistry of this first coupling was inconsequential since the NPG resulting from the automated synthesis was to be coupled at the reducing end. Elongation of the oligosaccharide chain was achieved using monosaccharide 7[7a], followed by deprotection of the 2-O-acetate using NaOMe. Coupling of building block 8 employing catalytic TMSOTf and deprotection with NaOMe proceeded smoothly to create a resin-bound trisaccharide, before the final coupling with donor 9.[1a] Cleavage of the octenediol linker using Grubbs' catalyst 40 under an atmosphere of ethylene provided crude n-pentenyl tetrasaccharide 46. HPLC analysis of the crude reaction products revealed two major peaks (FIG. 22): the desired tetrasaccharide 46 (44% relative area) and deletion sequences (15% relative area).

Figure 24:
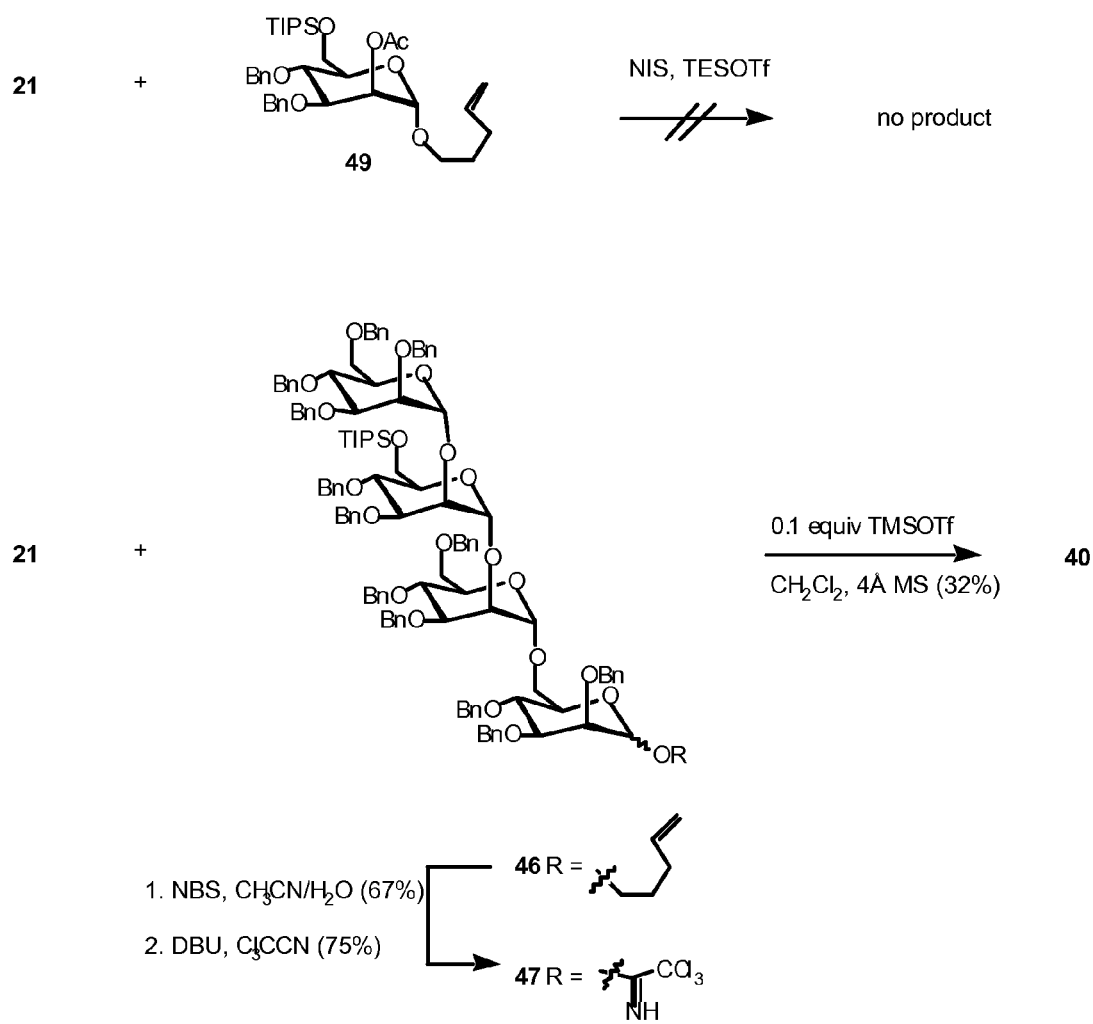
FIG. 24 depicts a 4+2 coupling.

The crude material was purified by HPLC to provide 46 as a mixture of α and β-anomers. Prior to attempting the crucial 4+2 coupling, a model coupling between NPG-monosaccharide 49 and disaccharide 21 was carried out but failed to produce the desired product (FIG. 24). The failure of 49 as an effective glycosyl donor led us to examine glycosyl trichloroacetimidate 47 as a coupling partner. Conversion of 46 into glycosyl donor 47 proceeded smoothly over two steps. Reaction of trichloroacetimidate 47 with disaccharide 21 afforded the desired hexasaccharide 40 in modest yield.

The material produced via the automated route was identical in all regards to material made previously in solution, and constitutes a formal synthesis of anti-toxin malaria vaccine 2.

Extentions to Other Structures

Figure 25:
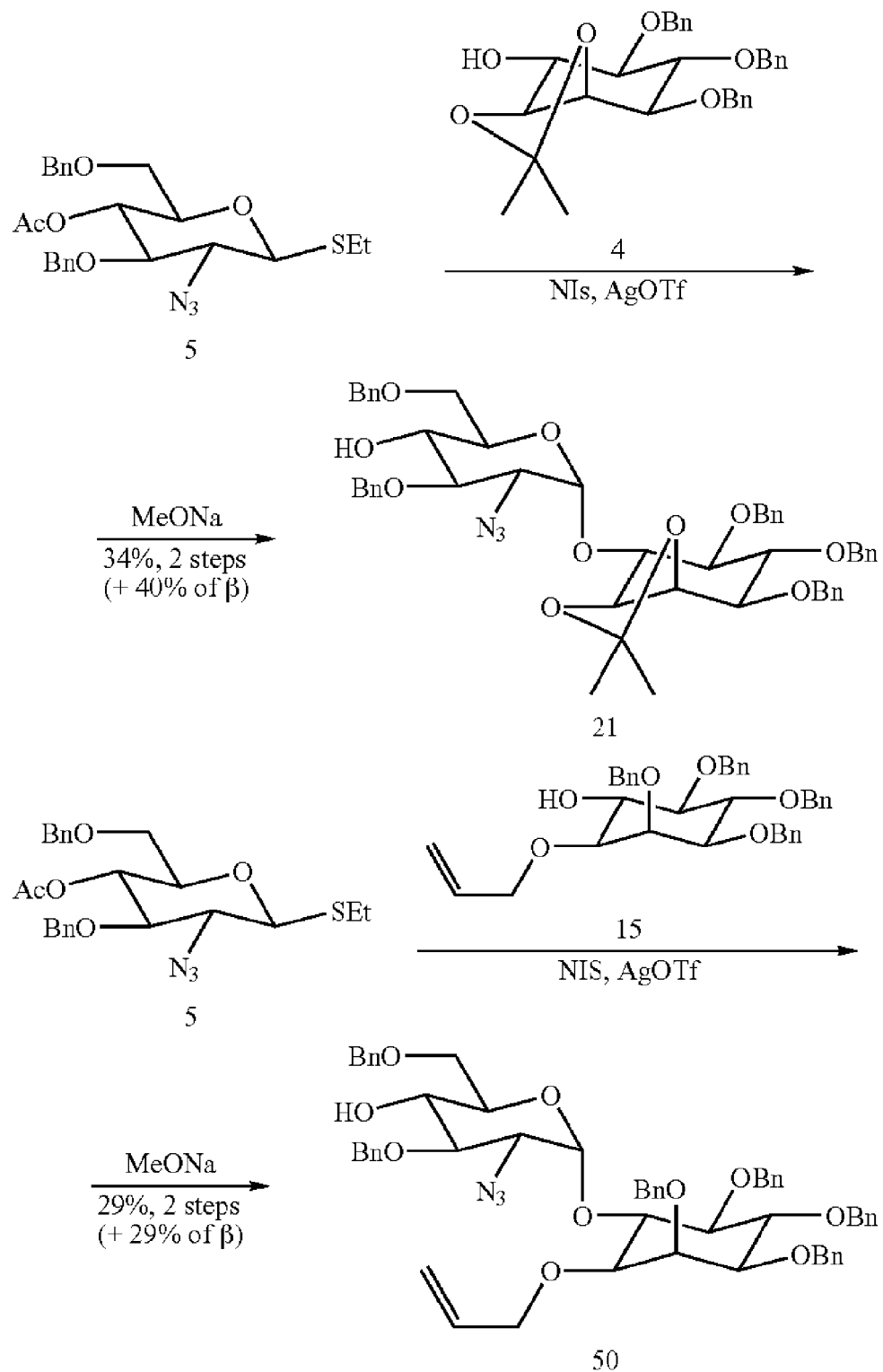
FIG. 25 depicts differentially-protected disaccharide acceptors.

To allow other phosphorylation patterns, use of the inositol acceptors with different protection patterns were necessary. Coupling acceptor 15 with thiodonor 5 under the same conditions as with acceptor 4 gave, following deacetylation, a separable anomeric mixture of disaccharide acceptors 50. (FIG. 25).

Figure 26:
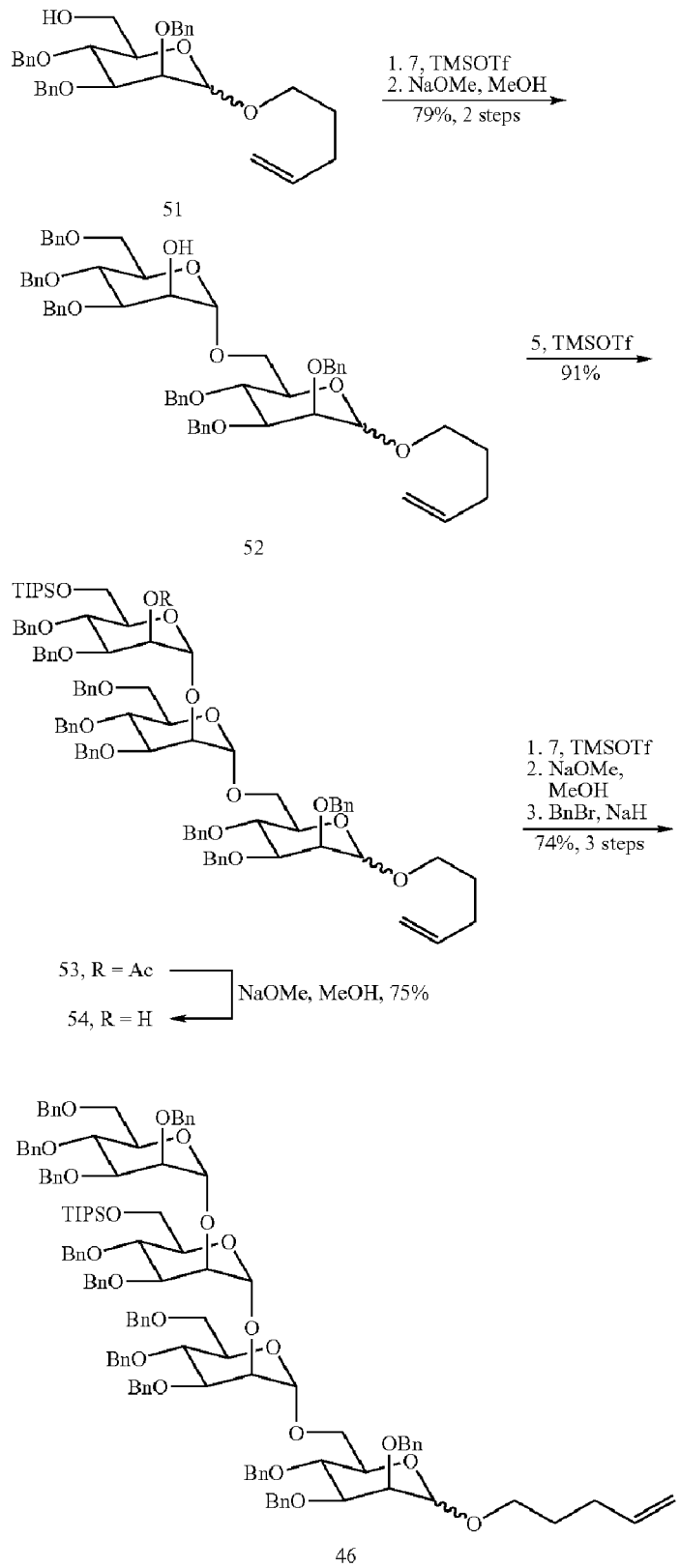
FIG. 26 depicts a solution-phase synthesis of tetramannose structure.

Tetramannose component 46 can also be prepared in solution, if large quantities are required (FIG. 26). Sequential coupling/deprotection of donors 7, 8, and 7 to acceptor 51, followed by benzylation of the free hydroxyl, gave 46 as expected.

Figure 27A:
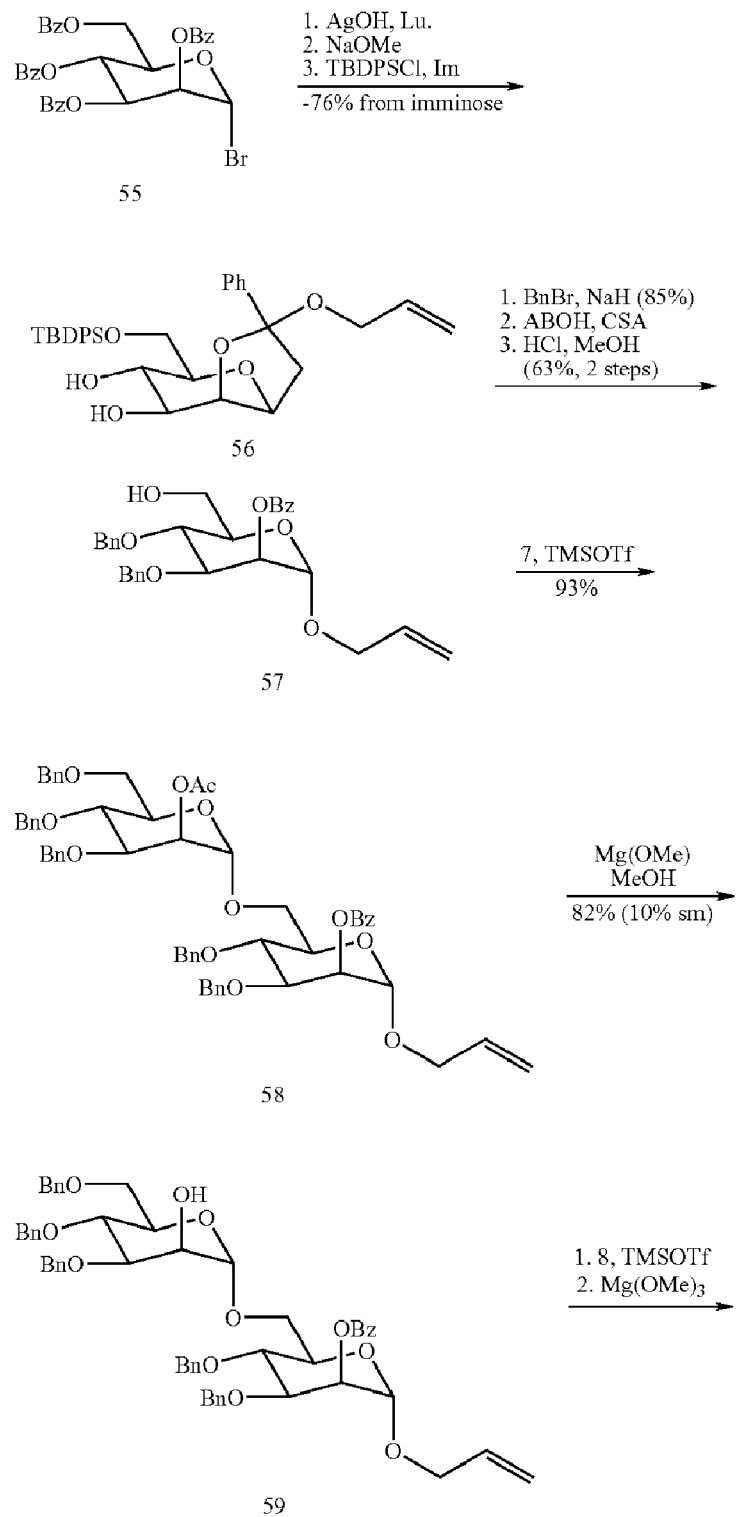

The modest 4+2 coupling yields seen above are partially due to the instability of the highly-activated tribenzyl donor being used. Furthermore, mammalian GPI structures have a phosphoethanolamine on the 2-OH of the first mannose residue. Both of these issues were addressed simultaneously by the use of an ester on the 2-position of the reducing-end mannose in the tetrasaccharide donor; the presence of ester attenuates the activity of the donor, resulting in less decomposition, and it is removed to enable installation of phosphoethanolamine. Our route is shown in FIG. 27: from known tetrabenzylmannose bromide, closure to the allyl orthoester takes place in the presence of the alcohol and 2,6-lutidine; debenzoylation and selective silylation of the primary hydroxyl gave 56 in good yield. Benzylation was followed by opening of the orthoester (in the presence of excess allyl alcohol) and acid-catalyzed desilation gave acceptor 57. This was coupled to 7 under standard conditions; selective removal of the acetate ester using magnesium methoxide gave 59 in 90% yield, based on the recovery of a small amount of starting material. Polymer extension proceeded using the same techniques, and allyl removal used standard conditions, providing the new tetrasaccharide donor 61.

SUMMARY

The synthesis of a pseudo-hexasaccharide glycosylphosphatidylinositol has been reduced to practice, both in solution and using a combination of solution and automated solid-phase methodologies. The material made in solution was covalently attached to a protein carrier and used to vaccinate mice. Innoculated mice were substantially protected against a subsequent challenge with *Plasmodium* parasites. This discovery further implicates GPI as the dominant toxin in malaria infections, and lays the groundwork for future trials in human volunteers. Combinations of solution and automated solid-phase synthetic methodologies will see continued usage in this context, and are expected to lead to the rapid generation of more potent vaccines for malaria and other maladies.

Compounds of the Invention

One aspect of the invention relates to compounds represented by formula I:

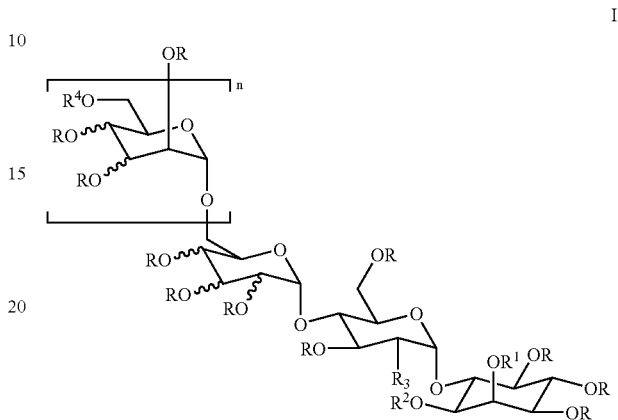

wherein, n is 1-4;

R represents independently for each occurrence H, alkyl, aryl, —CH$_2$-aryl, —C(O)-alkyl, —C(O)-aryl, or —Si(alkyl)$_3$;

R$^1$ and R$^2$ are independently H, —CH$_2$-aryl, —C(O)-alkyl, —C(O)-aryl, —Si(alkyl)$_3$; or R$^1$ and R$^2$ taken together are C(CH$_3$)$_2$, P(O)OH, or P(O)OR$^5$;

R$^3$ is amino, —N$_3$, or —NH$_3$X;

R$^4$ represents independently for each occurrence H, alkyl, aryl, —CH$_2$-aryl, —C(O)-alkyl, —C(O)-aryl, —Si(alkyl)$_3$, or —P(O)(OR$^5$)$_2$;

R$^5$ represents independently for each occurrence H, Li$^+$, Li$^+$, Na$^+$, K$^+$, Rb$^+$, Cs$^+$, aryl, or an optionally substituted alkyl group; and X is a halogen, alkyl carboxylate, or aryl carboxylate.

In certain embodiments, the present invention relates to the aforementioned compound, wherein n is 1, 2, or 3.

In certain embodiments, the present invention relates to the aforementioned compound, wherein n is 3.

In certain embodiments, the present invention relates to the aforementioned compound, wherein R is H.

In certain embodiments, the present invention relates to the aforementioned compound, wherein R$^1$ and R$^2$ taken together are P(O)OR$_5$.

In certain embodiments, the present invention relates to the aforementioned compound, wherein R$^3$ is N$_3$.

In certain embodiments, the present invention relates to the aforementioned compound, wherein R$^3$ is —NH$_3$X.

In certain embodiments, the present invention relates to the aforementioned compound, wherein R$^4$ represents independently for each occurrence H, —CH$_2$Ph, or Si(alkyl)$_3$;

In certain embodiments, the present invention relates to the aforementioned compound, wherein R$^4$ represents independently for each occurrence H, —CH$_2$Ph, or P(O)OR$^5$; and R$^5$ is an optionally substituted alkyl group.

In certain embodiments, the present invention relates to the aforementioned compound, wherein said compound of formula I is selected from the group consisting of:

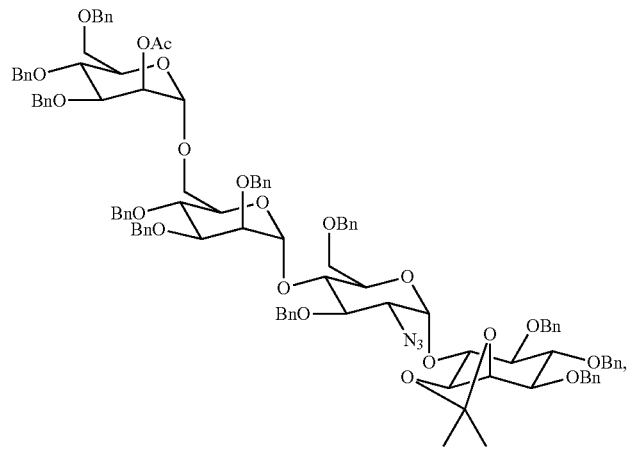
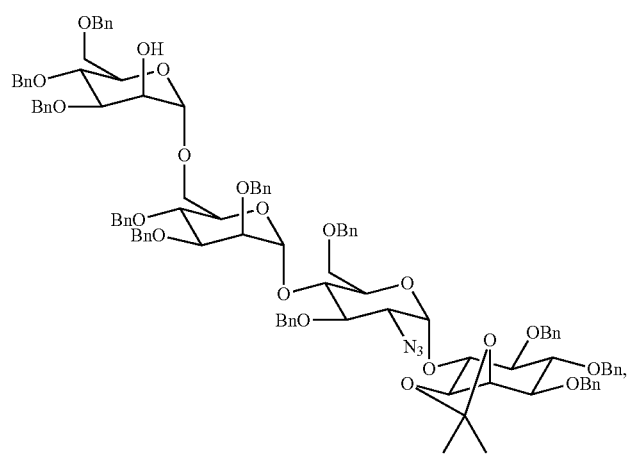
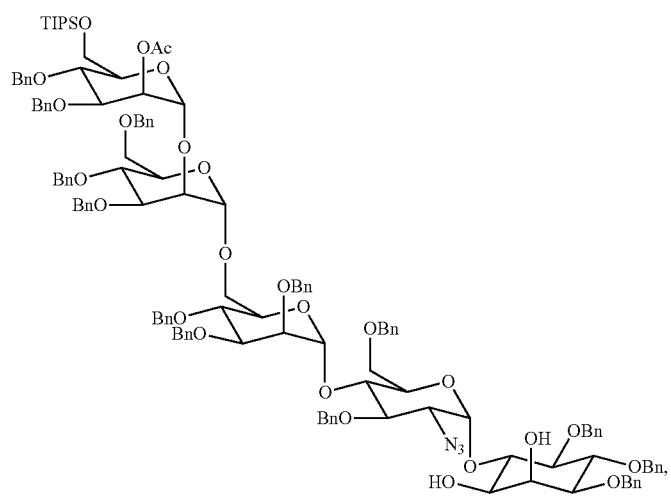

-continued
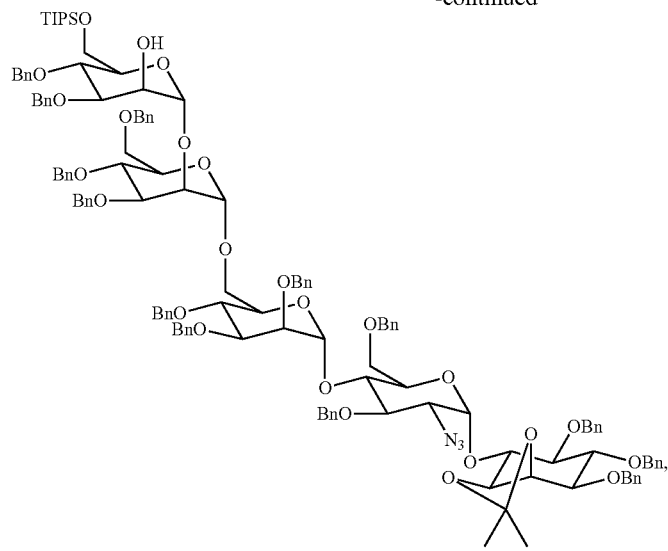
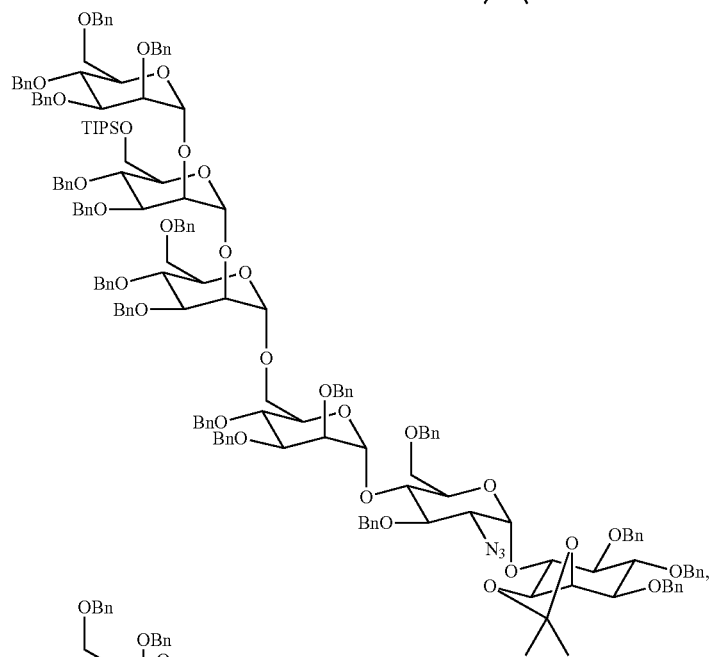
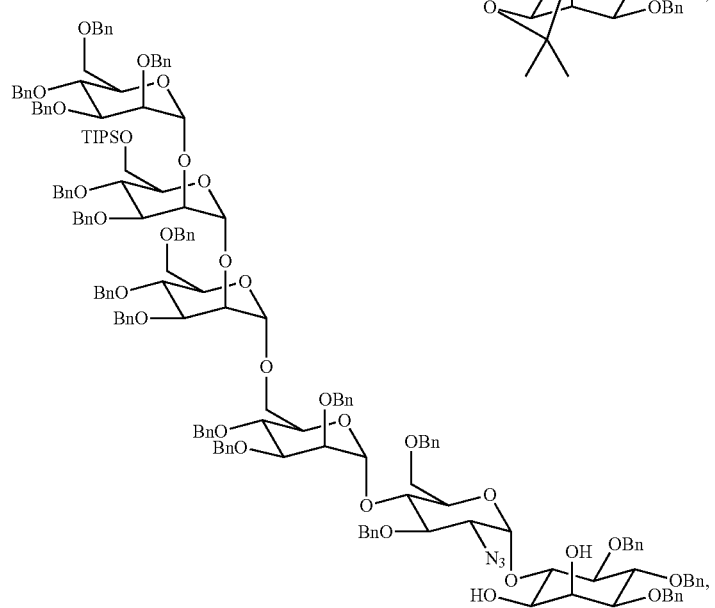

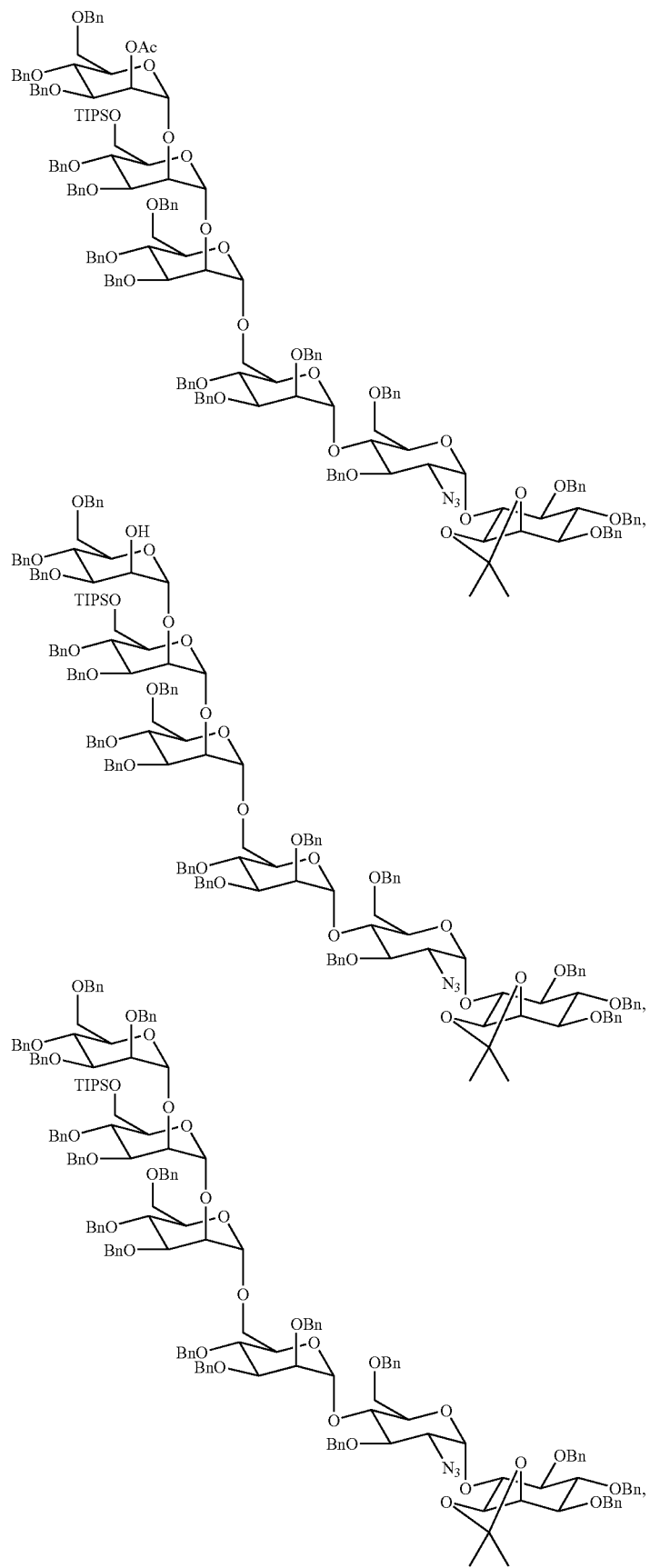

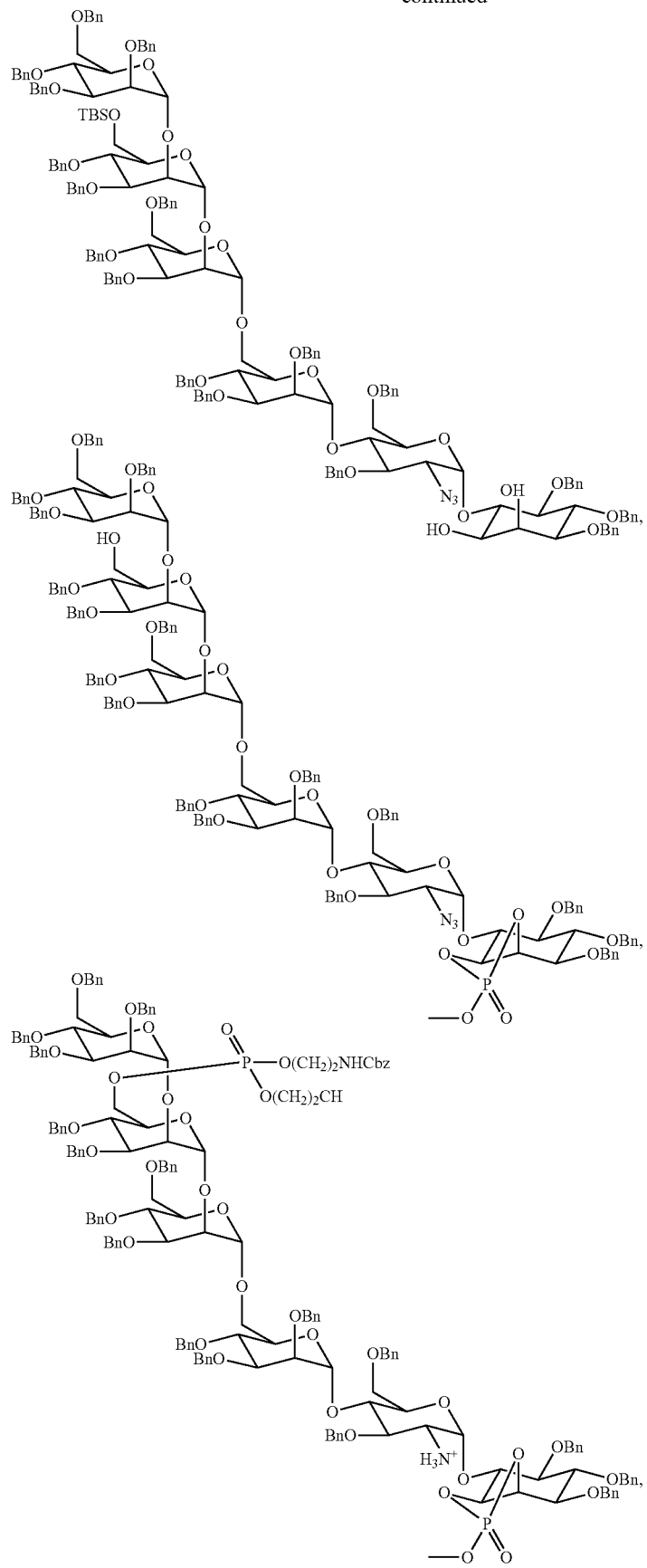

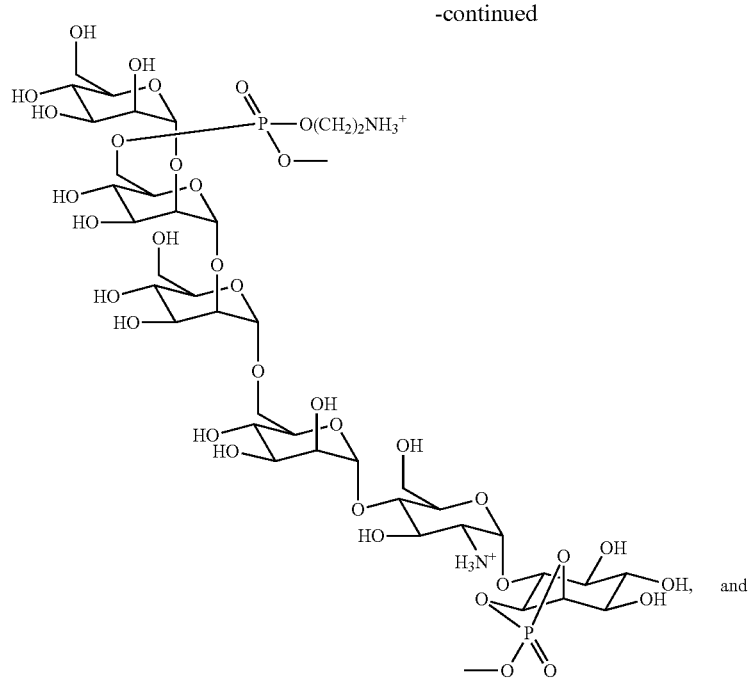
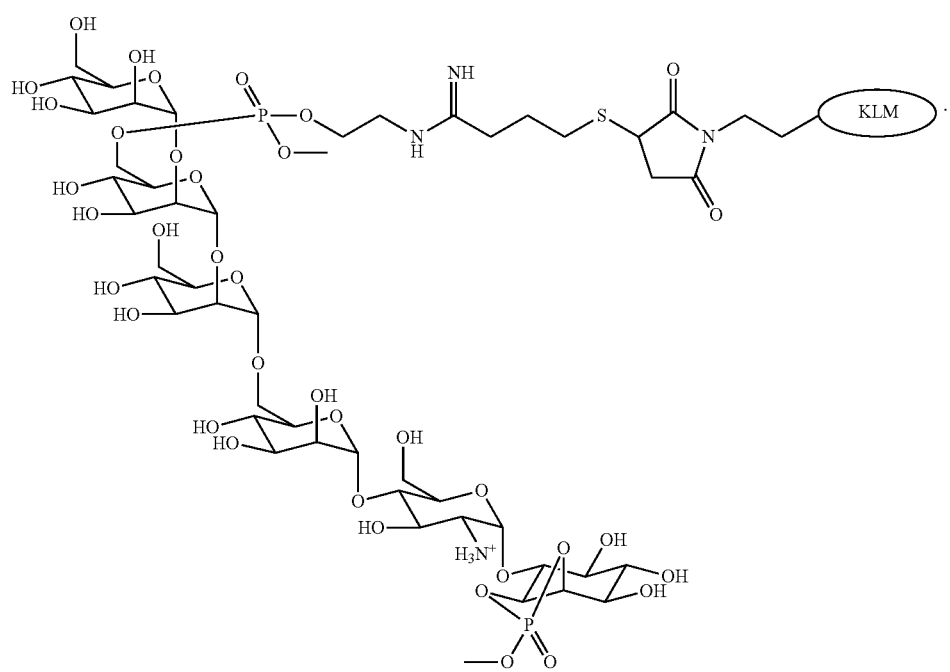

Another aspect of the invention relates to compounds represented by formula II:

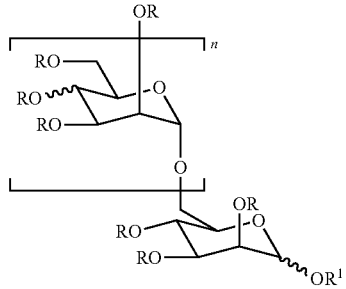

wherein, n is 1-4;

R represents independently for each occurrence H, alkyl, aryl, —CH$_2$-aryl, —C(O)-alkyl, —C(O)-aryl, or —Si(alkyl)$_3$;

R$^1$ is —(CH$_2$)$_m$CH=CH$_2$ or trichloroacetimidate; and m is 1-6.

In certain embodiments, the present invention relates to the aforementioned compound, wherein n is 2 or 3.

In certain embodiments, the present invention relates to the aforementioned compound, wherein n is 3.

In certain embodiments, the present invention relates to the aforementioned compound, wherein m is 3.

In certain embodiments, the present invention relates to the aforementioned compound, wherein R represents independently for each occurrence —CH$_3$-aryl or —Si(alkyl)$_3$.

In certain embodiments, the present invention relates to the aforementioned compound, wherein R represents independently for each occurrence benzyl or —Si(iPr)$_3$.

In certain embodiments, the present invention relates to the aforementioned compound, wherein said compound of formula II is selected from the group consisting of:

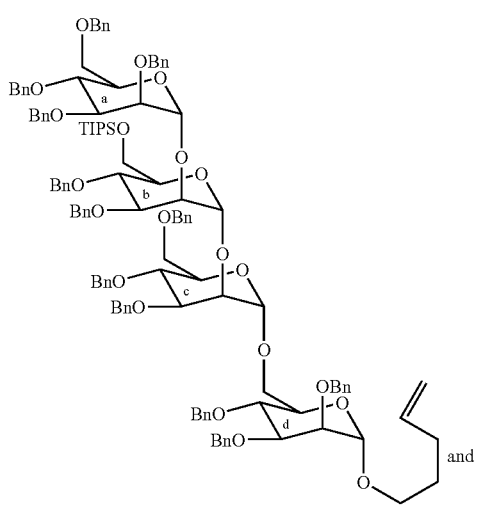

and

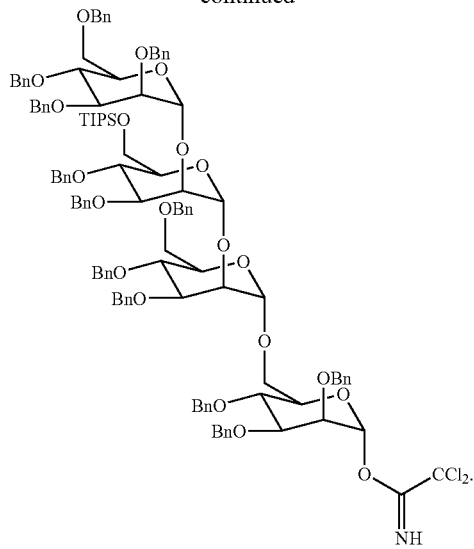

Preparation of Glycosylphosphatidylinositol Glycans

One aspect of the present invention relates to a method of preparing glycosylphosphatidylinositol glycans as depicted in Scheme 5:

Scheme 5

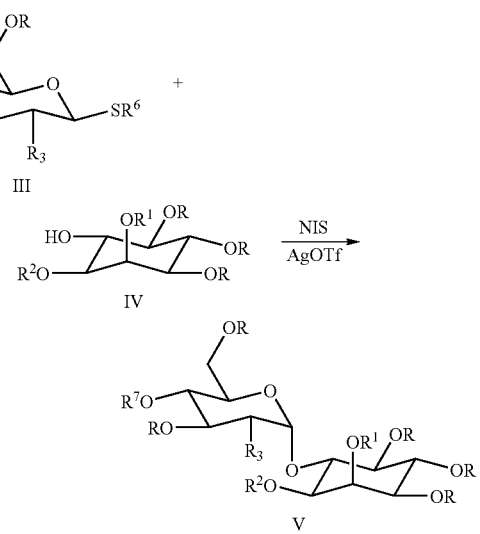

wherein,

R represents independently for each occurrence H, alkyl, aryl, —CH$_2$-aryl, —C(O)-alkyl, —C(O)-aryl, or —Si(alkyl)$_3$;

R$^1$ and R$^2$ are independently H, —CH$_2$-aryl, —C(O)-alkyl, —C(O)-aryl, —Si(alkyl)$_3$; or R$^1$ and R$^2$ taken together are C(CH$_3$)$_2$, P(O)OH, or P(O)OR$^5$;

R$^3$ is amino, —N$_3$, or —NH$_3$X;

R$^5$ represents independently for each occurrence H, Li$^+$, Li$^+$, Na$^+$, K$^+$, Rb$^+$, Cs$^+$, aryl, or an optionally substituted alkyl group;

R$^6$ is alkyl or aryl;

R$^7$ is alkyl, aryl, —CH$_2$-aryl, —C(O)-alkyl, —C(O)-aryl, or —Si(alkyl)$_3$; and X is a halogen, alkyl carboxylate, or aryl carboxylate.

In certain embodiments, the present invention relates to the aforementioned method, wherein R is —CH$_2$-aryl.

In certain embodiments, the present invention relates to the aforementioned method, wherein R$^1$ and R$^2$ taken together are C(CH$_3$)$_2$.

In certain embodiments, the present invention relates to the aforementioned method, wherein R$^3$ is —N$_3$.

In certain embodiments, the present invention relates to the aforementioned method, wherein R$^6$ is alkyl.

In certain embodiments, the present invention relates to the aforementioned method, wherein R$^7$ is —C(O)-alkyl.

In certain embodiments, the present invention relates to the aforementioned method, wherein R is benzyl, R$^1$ and R$^2$ taken together are C(CH)$_2$, and R$^3$ is —N$_3$.

In certain embodiments, the present invention relates to the aforementioned method, wherein R is benzyl, R$^1$ and R$^2$ taken together are C(CH$_3$)$_2$, R$^3$ is —N$_3$, and R$^6$ is ethyl.

Method of Preparing Glycosylphosphatidylinositol Glycans Using Automatic Synthesis on Solid Support One aspect of the present invention relates to a method of preparing glycosylphosphatidylinositol glycans, comprising the steps of:

binding a mannopyranoside to a solid support to provide a first substrate, reacting said first substrate with a mannopyranose trichloroacetimidate to give a disaccharide bound to said solid support, reacting said disaccharide with a mannopyranose trichloroacetimidate to give a triisaccharide bound to said solid support, reacting said trisaccharide with a mannopyranose trichloroacetimidate to give a tetrasaccharide bound to said solid support, and cleaving said tetrasaccharide from said solid support.

In certain embodiments, the present invention relates to the aforementioned method, wherein said mannopyranoside is bound to said solid support through a glycosidic linkage.

In certain embodiments, the present invention relates to the aforementioned method, wherein said tetrasaccharide is cleaved from said solid support using Grubbs' catalyst.

In certain embodiments, the present invention relates to the aforementioned method, wherein said tetrasaccharide is

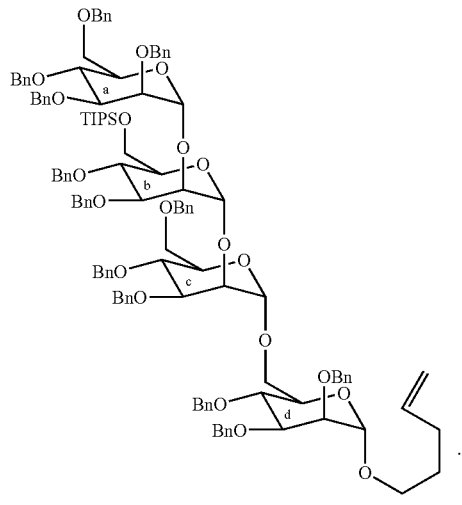

DEFINITIONS

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

For purposes of this invention, the chemical elements are identified in accordance with the Periodic Table of the Elements, CAS version, Handbook of Chemistry and Physics, 67th Ed., 1986-87, inside cover.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C$_1$-C$_{30}$ for straight chain, C$_3$-C$_{30}$ for branched chain), and more preferably 20 or fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means —NH$_2$; the term "nitro" means —NO$_2$; the term "halogen" designates —F, —Cl, —Br or —I; the term "thiol" means —SH; the term "hydroxyl" means —OH; the term "sulfonyl" means —SO$_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

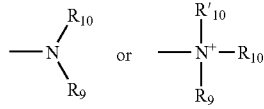

wherein R$_9$, R$_{10}$ and R'$_{10}$ each independently represent a group permitted by the rules of valence.

The term "acylamino" is art-recognized and refers to a moiety that can be represented by the general formula:

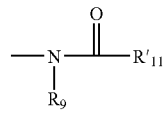

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art-recognized as an amino-substituted carbonyl and includes a moiety that can be represented by the general formula:

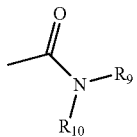

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art-recognized and includes such moieties as can be represented by the general formula:

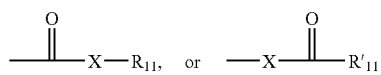

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an either is or resembles an alkoxyl, such as can be represented by one of —O-alkyl, —O-alkenyl, —O-alkynyl, —O—$(CH_2)_m$—$R_8$, and $R_8$ are described above.

The term "sulfonate" is art-recognized and includes a moiety that can be represented by the general formula:

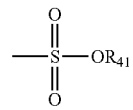

in which $R_{41}$ is an electron pair, hydrogen, alkyl, cycloalkyl, or aryl.

The term "sulfonylamino" is art-recognized and includes a moiety that can be represented by the general formula:

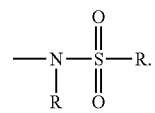

The term "sulfamoyl" is art-recognized and includes a moiety that can be represented by the general formula:

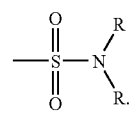

The term "sulfonyl", as used herein, refers to a moiety that can be represented by the general formula:

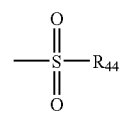

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

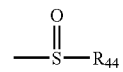

In which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

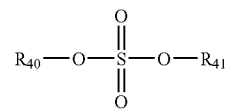

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

The term "trichloroacetimidate" refers a moiety that can be represented by the general structure:

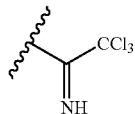

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

EXEMPLIFICATION

The invention now being generally described, it will be more readily understood by reference to the following examples, which are included merely for purposes of illustration of certain aspects and embodiments of the present invention, and are not intended to limit the invention.

Materials and Methods

All reactions were performed in oven-dried glassware under an atmosphere of nitrogen unless noted otherwise. Reagent grade chemicals were used as supplied except where noted. Phosphate buffered saline (PBS) was purchased from Boehringer Mannheim and diluted to the desired concentration. Pd-10 columns were purchased from Pharmacia. Trimethylsilyl trifluoromethanesulfonate (TMSOTf) was purchased from Acros Chemicals. N,N-Dimethylformamide (DMF) was obtained from Aldrich Chemical Co. (Sure-Seal Grade) and used without further purification. Merrifield's resin (1% crosslinked) was obtained from Novabiochem. Dichloromethane ($CH_2Cl_2$) and tetrahydrofuraran (THF) were purchased from J. T. Baker (Cycletainer™) and passed through neutral alumina columns prior to use. Toluene was purchased from J. T. Baker (Cycletainer™) and passed through a neutralalumina column and a copper (II) oxide column prior to use. Pyridine, triethylamine and acetonitrile were refluxed over calcium hydride and distilled prior to use. Analytical thin-layer chromatography was performed on E. Merck silica column 60 $F_{254}$ plates (0.25 mm). Compounds were visualized by dipping the plates in a cerium sulfate-ammonium molybdate solution followed by heating. Liquid column chromatography was performed using forced flow of the indicated solvent on Silicycle 230-400 mesh (60 Å pore diameter) silica gel.

Instrumentation

IR spectra were obtained on a Perkin-Elmer 1600 series FTIR spectrometer. Optical rotations were recorded on a Perkin-Elmer 241 polarimeter using a sodium lamp (589 nm). $^1$H NMR spectra were obtained on a Varian VXR-300 (300 MHz), a Varian VXR-500 (500 MHz) or a Bruker (400 MHz) spectrometer and are reported in parts per million (δ) relative to $CHCl_3$ (7.27 ppm). Coupling constants (J) are reported in Hertz. $^{13}$C NMR spectra were obtained on a Varian VXR-300 (75 MHz), a Varian VXR-500 (125 MHz) or a Bruker (100 MHz) spectrometer and are reported in δ relative to $CDCl_3$ (77.23 ppm) as an internal reference. $^{31}$P NMR spectra were obtained on a Varian VXR-300 (120 MHz) and are reported in δ relative to H₃PO₄ (0.0 ppm) as an external reference.

Example 1

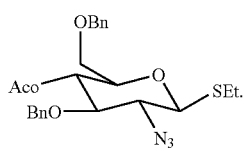

5

Ethyl-4-O-acetyl-2-azido-3,6-di-O-benzyl-2-deoxy-thio-β-D-glucopyranoside 5. $[\alpha]^{24}_D$: −43.5° (c 1.07, CH₂Cl₂); IR (thin film) 2916, 2108, 1743, 1222, 1047 cm⁻¹; ¹H NMR (500 MHz, CDCl₃) δ 7.40-7.29 (m, 10H), 5.06-5.02 (m, 1H), 4.86 (d, J=11.3 Hz, 1H), 4.68 (d, J=11.3 Hz, 1H), 4.52 (s, 2H), 4.34 (d, J=9.5 Hz, 1H), 3.59-3.48 (m, 6H), 2.83-2.73 (m, 2H), 1.87 (s, 3H), 1.35 (t, J=7.3 Hz, 3H); ¹³C-NMR (125 MHz, CDCl₃) δ 169.9, 138.0, 137.8, 128.8, 128.6, 128.3, 128.1, 128.0, 84.5, 82.8, 77.9, 75.9, 73.8, 71.1, 69.9, 66.0, 25.0, 21.0, 15.4; FAB MS m/z (M+Na)⁺ calcd 494.1726, found 494.1716.

Example 2

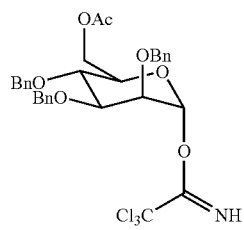

6

6-O-Acetyl-2,3,4-tri-O-benzyl-α-D-mannopyranose trichloroacetimidate 6. $[\alpha]^{24}_D$: +34.4° (c 2.18, CH₂Cl₂); IR (thin film) 2938, 2880, 1707, 1683, 1220 cm⁻¹; ¹H NMR (500 MHz, CDCl₃) δ 8.53 (s, 1H), 7.38-7.21 (m, 14H), 6.29 (d, J=2.1 Hz, 1H), 4.91 (d, J=10.7 Hz, 1H), 4.73 (s, 2H), 4.61-4.55 (m, 3H), 4.33 (dd, J=2.1, 12.2 Hz, 1H), 4.24 (dd, J=4.3, 11.9 Hz, 1H), 4.00-3.90 (m, 4H), 3.84-3.83 (m, 1H), 2.00 (s, 3H); ¹³C-NMR (125 MHz, CDCl₃) δ 170.8, 160.3, 137.8, 137.8, 137.7, 128.5, 128.4, 128.3, 128.3, 128.0, 127.8, 127.8, 95.6, 78.8, 75.3, 73.6, 73.2, 72.7, 72.5, 72.2, 63.0, 20.8; FAB MS m/z (M+Na)⁺ calcd 658.1137, found 658.1123.

Example 3

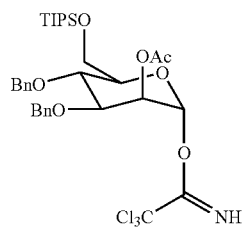

8

2-O-Acetyl-3,4-di-O-benzyl-6-O-triisopropylsilyl-α-D-mannopyranose trichloroacetimidate 8. $[\alpha]^{24}_D$: +43.4° (c 2.20, CH₂Cl₂); IR (thin film) 2940, 2865, 1752, 1674, 1229 cm⁻¹; ¹H NMR (500 MHz, CDCl₃) δ 8.63 (s, 1H), 7.38-7.26 (m, 10H), 6.26 (d, J=1.8 Hz, 1H), 5.46 (dd, J=2.1, 3.1 Hz, 1H), 4.93 (d, J=10.4 Hz, 1H), 4.75 (d, J=11.3 Hz, 1H), 4.71 (d, J=10.7 Hz, 1H), 4.62-4.57 (m, 1H), 4.17 (t, J=9.8 Hz, 1H), 4.09-4.05 (m, 2H), 3.95 (d, J=11.3 Hz, 1H), 3.85 (dd, J=1.5, 9.8 Hz, 1H), 2.16 (s, 3H), 1.15-1.05 (m, 22H); ¹³C-NMR (125 MHz, CDCl₃) δ 170.8, 160.7, 139.1, 138.3, 129.1, 129.1, 129.0, 128.8, 128.6, 128.5, 96.2, 91.6, 77.9, 76.3, 74.0, 72.8, 68.1, 62.8, 21.6, 18.7, 18.6, 12.8; FAB MS m/z (M+Na)⁺ calcd 724.2007, found 724.2006.

Example 4

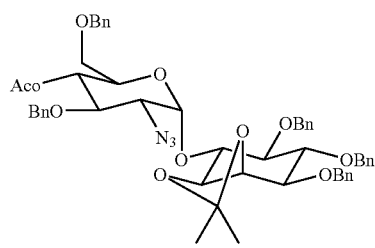

20

O-(4-O-Acetyl-2-azido-3,6-di-O-benzyl-2-deoxy-α-D-glucopyranosyl)-(1→6)-3,4,5-tri-O-benzyl-1,2-O-isopropylidene-D-myo-inositol 20. A mixture of thiodonor 5 (3.21 g, 6.82 mmol) and inositol 4 (2.78 g, 5.68 mmol) were azeotroped with toluene (3×100 mL) and dried under vacuum for 16 h; The oil was dissolved in Et₂O (110 mL)/CH₂Cl₂ (30 mL) and freshly dried 4 Å molecular sieves (4 g) were added. After stirring for 30 min at room temperature, the cloudy mixture was cooled to −40° C., and NIS (2.04 g, 9.09 mmol) was added. A 0.5 M solution of AgOTf in toluene (4.54 ml, 2.27 mmol) was added via cannula, and the flask was covered with aluminum foil and allowed to warm to room temperature. After 15 h, the sieves were filtered off and the orange solution was diluted with CH₂Cl₂ (100 mL), washed with sat. aqueous NaHCO₃ (2×100 mL) and brine (1×100 mL). Following drying (Na₂SO₄), filtration and concentration the crude product was purified by flash silica column chromatography (20→30% EtOAc/hexanes) to afford 20 (3.56 g, 70%) as a 1.2:1 α/β mixture. α-isomer: $[\alpha]^{24}_D$: +58.4° (c 1.92, CH₂Cl₂); IR (thin film) 2106, 1742, 1454, 1229, 1042 cm⁻¹; ¹H NMR (500 MHz, CDCl₃) δ 7.40-7.22 (m, 20H), 5.62 (d, J=3.4 Hz, 1H), 5.14 (app t, 1H), 4.88-4.73 (m, 5H), 4.68 (d, J=11.3 Hz, 1H), 4.57 (d, J=11.0 Hz, 1H), 4.46 (d, J=11.9 Hz, 1H), 4.33 (d, J=11.9 Hz, 1H), 4.25 (app t, 1H), 4.18 (app t, 1H), 4.13-4.09 (m, 2H), 3.94 (app t, 1H), 3.88 (t, J=9.8 Hz, 1H), 3.72 (dd, J=3.7, 8.5 Hz, 1H), 3.46-3.40 (m, 2H), 3.27 (dd, J=2.4, 11.0 Hz, 1H), 3.12 (dd, J=4.0, 11.0 Hz, 1H), 1.74 (s, 3H), 1.55 (s, 3H), 1.36 (s, 3H); ¹³C-NMR (125 MHz, CDCl₃) δ 170.0, 139.0, 138.9, 138.7, 138.5, 138.3, 129.2, 129.2, 129.1, 128.9, 128.9, 128.8, 128.7, 128.7, 128.6, 128.4, 128.3, 128.3, 128.1, 111.0, 96.0, 81.7, 81.2, 79.8, 78.3, 77.9, 77.4, 75.9, 75.4, 75.0, 74.0, 73.9, 71.0, 69.2, 68.5, 63.4, 28.4, 26.5, 21.5; FAB MS m/z (M+Na)$^+$ calcd 922.3891, found 922.3864.

Example 5

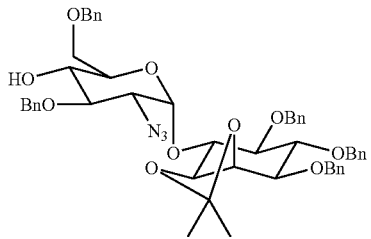

21

O-(2-Azido-3,6-di-O-benzyl-2-deoxy-α-D-glucopyranosyl)-(1→6)-3,4,5-tri-O-benzyl-1,2-O-isopropylidene-D-myo-inositol 21. α-Disaccharide 20 (1.85 g, 2.0 mmol) was dissolved in CH$_2$Cl$_2$ (8 mL) and a 0.5 M solution of sodium methoxide in methanol (8 mL, 4.0 mmol) was added. After 21 h, the clear solution was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (10→40% EtOAc/hexanes) to afford 21 (1.24 g, 70%). [α]$^{24}_D$: +47.2° (c 2.76, CH$_2$Cl$_2$); IR (thin film) 2105, 1496, 1454, 1044, 726 cm$^{-1}$; $^1$H NMR (500 MHz, CDCl$_3$) δ 7.40-7.09 (m, 25H), 5.57 (d, J=3.7 Hz, 1H), 4.88-4.74 (m, 8H), 4.67 (d, J=10.7 Hz, 1H), 4.48 (d, J=12.2 Hz, 1H), 4.40 (d, J=12.2 Hz, 1H), 4.25 (dd, J=4.0, 5.5 Hz, 1H), 4.19-4.16 (m, 1H), 4.07 (dd, J=7.0, 10.1 Hz, 1H), 4.00-3.97 (m, 1H), 3.95 (t, J=8.6 Hz, 1H), 3.78-3.69 (m, 3H), 3.48-3.41 (m, 3H), 3.31 (dd, J=3.7, 9.8 Hz, 1H), 1.55 (s, 3H), 1.35 (s, 3H); $^{13}$C-NMR (125 MHz, CDCl$_3$) δ 139.1, 138.8, 138.8, 138.7, 138.6, 129.3, 129.2, 129.1, 129.1, 128.9, 128.8, 128.8, 128.7, 128.6, 128.6, 128.4, 128.4, 110.9, 96.2, 81.6, 81.3, 80.0, 79.9, 78.0, 77.8, 77.5, 76.1, 75.8, 75.6, 75.4, 74.0, 73.2, 70.3, 70.1, 63.4, 28.4, 26.5; FAB MS m/z (M+Na)$^+$ calcd 880.3785, found 880.3769.

Example 6

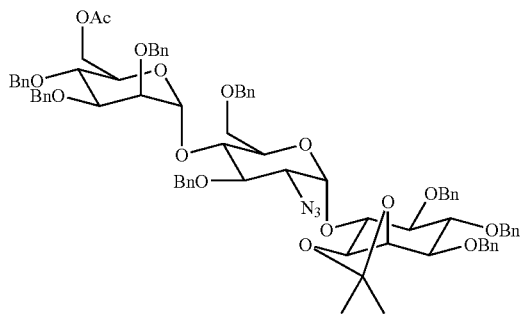

22

O-(6-O-Acetyl-2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 22. A mixture of disaccharide acceptor 21 (1.24 g, 1.17 mmol) and donor 6 (890 mg, 1.4 mmol) were azeotroped with toluene (3×40 mL) and dried under vacuum for 16 h. The mixture was dissolved in CH$_2$Cl$_2$ (11 mL) and TMSOTf (11 µL, 0.058 mmol) was added. After 30 min, the orange solution was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (10→30% EtOAc/hexanes) to afford 22 (592 mg, 47%) and 75 (797 mg, 75% based on recovered 74). [α]$^{24}_D$: +55.2° (c 1.01, CH$_2$Cl$_2$); IR (thin film) 2923, 2104, 1740, 1454, 697 cm$^{-1}$; $^1$H NMR (500 MHz, CDCl$_3$) δ 7.39-7.07 (m, 33H), 5.63 (d, J=3.7 Hz, 1H), 5.20 (d, J=1.5 Hz, 1H), 4.94-4.90 (m, 2H), 4.82-4.74 (m, 4H), 4.68 (d, J=10.7 Hz, 1H), 4.65-4.50 (m, 3H), 4.43 (d, J=8.8 Hz, 1H), 4.41 (d, J=8.8 Hz, 1H), 4.30 (d, J=11.9 Hz, 1H), 4.27-4.25 (m, 1H), 4.22-4.06 (m, 6H), 3.93-3.88 (m, 2H), 3.83-3.78 (m, 3H), 3.74-3.67 (m, 3H), 3.57 (d, J=2.4 Hz, 1H), 3.45-3.41 (m, 1H), 3.37-3.34 (m, 1H), 1.96 (s, 3H), 1.55 (s, 3H), 1.35 (s, 3H); $^{13}$C-NMR (125 MHz, CDCl$_3$) δ 170.5, 138.2, 138.1, 138.0, 137.9, 137.8, 137.8, 137.4, 128.3, 128.2, 128.2, 128.1, 128.1, 128.0, 127.9, 127.8, 127.7, 127.6, 127.5, 127.5, 127.4, 127.3, 127.2, 127.0, 126.8, 126.5, 110.0, 100.6, 95.1, 80.6, 80.4, 79.5, 79.2, 78.8, 78.0, 78.0, 77.1, 76.3, 75.7, 75.0, 74.8, 74.7, 74.4, 74.0, 73.8, 73.0, 72.7, 71.8, 71.7, 70.7, 69.6, 68.2, 63.2, 62.9, 29.4, 27.3, 25.5, 20.6; FAB MS m/z (M+Na)$^+$ calcd 1354.5827, found 1354.5859.

Example 7

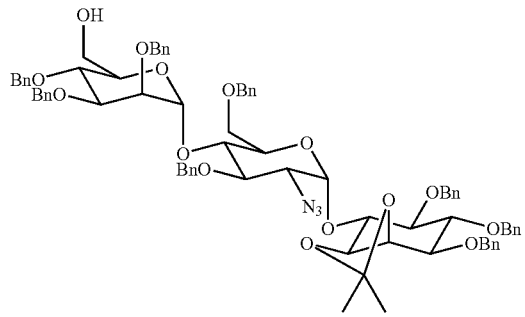

23

O-(2,3,4-Tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 23. Trisaccharide 22 (1.42 g, 1.06 mmol) was dissolved in CH$_2$Cl$_2$ (11 mL) and a 0.5 M solution of sodium methoxide In methanol (2.12 mL, 1.06 mmol) was added. After 2 h, the clear solution was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (10→40% EtOAc/hexanes) to afford 23 (973 mg, 71%). [α]$^{24}_D$: +42.0° (c 1.76, CH$_2$Cl$_2$); IR (thin film) 2291, 2104, 1454, 1360, 735 cm$^{-1}$; $^1$H NMR (500 MHz, CDCl$_3$) δ 7.40-7.10 (m, 42H), 5.61 (d, J=3.7 Hz, 1H), 5.24 (d, J=2.1 Hz, 1H), 4.90-4.88 (m, 2H), 4.83-4.67 (m, 6H), 4.63-4.54 (m, 4H), 4.51 (s, 2H), 4.44 (d, J=11.9 Hz, 1H), 4.34 (d, J=11.9 Hz, 1H), 4.25 (dd, J=3.7, 5.5 Hz, 1H), 4.20-4.17 (m, 1H), 4.15-4.03 (m, 3H), 3.94-3.79 (m, 5H), 3.77 (dd, J=2.4, 8.85 Hz, 1H), 3.74-3.72 (m, 1H), 3.66-3.62 (m, 3H), 3.59-3.56 (m, 2H), 3.49-3.47 (m, 1H), 3.42 (dd, J=8.2, 9.8 Hz, 1H), 3.36 (dd, J=3.7, 10.1 Hz, 1H), 2.16 (bs, 1H), 1.56 (s, 3H), 1.36 (s, 3H); $^{13}$C-NMR (125 MHz, CDCl$_3$) δ 139.3, 139.2, 139.1, 139.0, 138.9, 138.7, 138.5, 129.4, 129.3, 129.3, 129.2, 129.2, 129.1, 129.0, 129.0, 129.0, 128.9, 128.8, 128.8, 128.7, 128.6, 128.6, 128.5, 128.5, 128.4, 128.4, 128.3, 128.2, 128.0, 127.9, 127.7, 111.0, 101.5, 96.1, 81.6, 81.3, 80.8, 79.9, 79.9, 78.3, 78.0, 77.3, 77.3, 76.8, 76.6, 75.9, 75.8, 75.6, 75.5, 75.4, 74.9, 74.8, 74.8, 74.6, 74.1, 74.0, 73.4, 73.2, 73.0, 72.7, 71.0, 68.7, 64.0, 63.1, 61.7, 30.4, 28.4, 26.5; FAB MS m/z (M+Na)$^+$ calcd 1312.5722, found 1312.5680.

Example 8

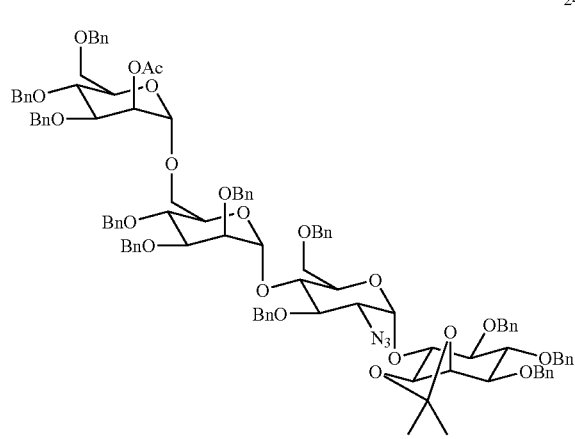

24

O-(2-O-Acetyl-3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 24. A mixture of trisaccharide acceptor 23 (970 mg, 0.75 mmol) and donor 7 (1.00 g, 1.50 mmol) were azeotroped with toluene (3×30 mL) and dried under vacuum for 1 h. The mixture was dissolved in CH$_2$Cl$_2$ (7 mL) and a 0.5 M solution of TMSOTf in CH$_2$Cl$_2$ (76 μL, 0.038 mmol) was added. After 15 min, the orange solution was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (10→40% EtOAc/hexanes) to afford 24 (1.22 g, 92%). [α]$^{24}$$_D$: +58.9° (c 3.30, CH$_2$Cl$_2$); IR (thin film) 3029, 2105, 1745, 1454, 1237 cm$^{-1}$; $^1$H NMR (500 MHz, CDCl$_3$) δ 7.40-7.10 (m, 54H), 5.62 (d, J=3.4 Hz, 1H), 5.49-5.48 (m, 1H), 5.26 (s, 1H), 4.94-4.88 (m, 4H), 4.85-4.75 (m, 7H), 4.69 (d, J=10.9 Hz, 1H), 4.62 (d, J=12.2 Hz, 1H), 4.58-4.55 (m, 2H), 4.54-4.46 (m, 4H), 4.44-4.36 (m, 4H), 4.33-4.30 (m, 1H), 4.28-4.23 (m, 3H), 4.20-4.09 (m, 3H), 3.98-3.79 (m, 10H), 3.74-3.66 (m, 5H), 3.61 (dd, J=3.7, 10.7 Hz, 1H), 3.56 (s, 2H), 3.52-3.42 (m, 4H), 3.35 (dd, J=3.7, 9.2 Hz, 1H), 2.12 (s, 3H), 1.54 (s, 3H), 1.35 (s, 3H); $^{13}$C-NMR (125 MHz, CDCl$_3$) δ 170.1, 138.7, 138.6, 138.5, 138.4, 138.3, 138.2, 138.1, 138.0, 137.8, 137.7, 128.5, 128.4, 128.4, 128.3, 128.3, 128.2, 128.2, 128.2, 128.1, 128.1, 128.0, 128.0, 127.9, 127.8, 127.7, 127.7, 127.7, 127.6, 127.6, 127.5, 127.5, 127.4, 127.3, 127.3, 127.2, 127.1, 127.0, 110.2, 100.3, 98.3, 95.2, 80.9, 80.6, 79.8, 79.1, 77.7, 77.2, 76.6, 75.9, 75.3, 75.1, 75.0, 74.7, 74.6, 74.2, 74.0, 73.8, 73.3, 72.9, 72.2, 72.1, 71.9, 71.3, 71.2, 69.8, 68.7, 68.6, 68.2, 66.4, 62.9, 29.7, 27.5, 25.7, 21.1; FAB MS m/z (M+Na)$^+$ calcd 1786.7764, found 1786.7710.

Example 9

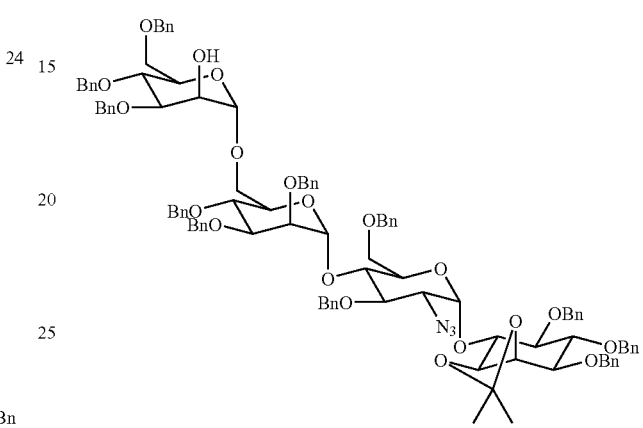

25

O-(3,4,6-Tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 25. Tetrasaccharide 24 (1.22 g, 0.70 mmol) was dissolved in CH$_2$Cl$_2$ (7 mL) and a 0.5 M solution of sodium methoxide in methanol (1.4 mL, 0.70 mmol) was added. After 2 h, the clear solution was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (20→40% EtOAc/hexanes) to afford 25 (820 mg, 69%). [α]$^{24}$$_D$: +54.7° (c 2.32, CH$_2$Cl$_2$); IR (thin film) 2923, 2105, 1454, 1046, 735 cm$^{-1}$; $^1$H NMR (500 MHz, CDCl$_3$) δ 7.40-7.09 (m, 51H), 5.64 (d, J=3.7 Hz, 1H), 5.24 (d, J=1.5 Hz, 1H), 5.00 (s, 1H), 4.93-4.89 (m, 2H), 4.84-4.75 (m, 6H), 4.68 (d, J=10.7 Hz, 1H), 4.64-4.40 (m, 12 H), 4.30-4.25 (m, 2H), 4.20-4.09 (m, 4H), 4.04 (s, 1H), 3.96 (t, J=9.5 Hz, 1H), 3.92-3.89 (m, 1H), 3.86-3.77 (m, 6H), 3.74-3.60 (m, 6H), 3.58-3.54 (m, 4H), 3.46-3.42 (m, 1H), 3.36 (dd, J=4.0, 9.2 Hz, 1H), 2.20 (bs, 1H), 1.55 (s, 3H), 1.36 (s, 3H); $^{13}$C-NMR (125 MHz, CDCl$_3$) δ 139.5, 139.2, 139.1, 139.0, 139.0, 138.9, 138.8, 138.7, 138.5, 138.4, 129.3, 129.2, 129.1, 129.1, 129.0, 129.0, 128.9, 128.8, 128.6, 128.5, 128.5, 128.4, 128.4, 128.3, 128.3, 128.2, 128.2, 128.1, 128.0, 127.9, 127.6, 111.0, 101.2, 100.6, 96.0, 81.6, 81.3, 80.6, 80.3, 80.2, 79.8, 78.1, 77.3, 76.9, 76.1, 75.8, 75.7, 75.6, 75.4, 75.0, 74.8, 74.6, 74.1, 74.0, 73.6, 73.4, 73.0, 72.8, 71.9, 71.8, 70.5, 69.5, 69.4, 68.4, 66.9, 63.7, 30.4, 28.3, 26.5; MALDI-TOF [M+Na]+ 1746.

Example 10

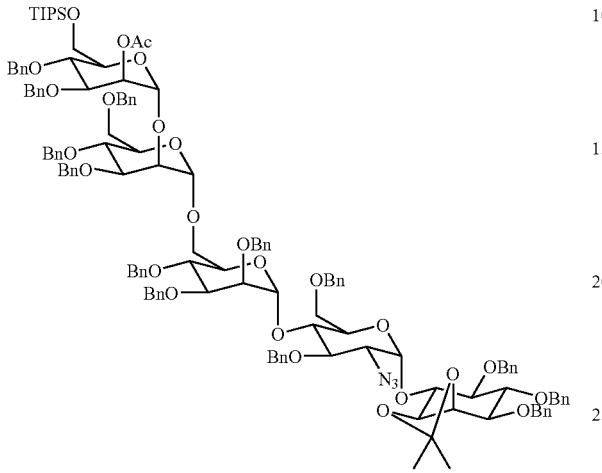

26

O-(2-O-Acetyl-3,4-di-O-benzyl-6-O-triisopropyllsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 26. A mixture of tetrasaccharide acceptor 25 (615 mg, 0.36 mmol) and donor 8 (502 mg, 0.71 mmol) were azeotroped with toluene (3×10 mL) and dried under vacuum for 16 h. The mixture was dissolved in $CH_2Cl_2$ (4 mL) and a 0.5 M solution of TBSOTf in $CH_2Cl_2$ (36 μL, 0.018 mmol) was added. After 10 min, the orange solution was diluted with $CH_2Cl_2$ (50 mL), washed with sat. aqueous $NaHCO_3$ (2×50 mL) and brine (1×50 mL). Following drying ($Na_2SO_4$), filtration and concentration the crude product was purified by flash silica column chromatography (20→40% EtOAc/hexanes) to afford 26 (789 mg, 98%). $[\alpha]^{24}_D$: +38.7° (c 2.57, $CH_2Cl_2$); IR (thin film) 2924, 2105, 1743, 1454, 735 cm$^{-1}$; $^1$H NMR (500 MHz, CDCl$_3$) δ 7.40-7.09 (m, 55H), 5.61 (d, J=3.7 Hz, 1H), 5.48-5.47 (m, 1H), 5.28 (d, J=1.5 Hz, 1H), 5.08 (d, J=1.5 Hz, 1H), 4.95-4.74 (m, 10H), 4.69-4.66 (m, 3H), 4.62 (d, J=11.3 Hz, 1H), 4.58-4.34 (m, 12H), 4.28-4.25 (m, 2H), 4.20-4.04 (m, 7H), 4.00 (dd, J=3.0, 9.8 Hz, 1H), 3.95-3.66 (m, 15H), 3.60-3.38 (m, 6H), 3.35 (dd, J=3.7, 10.1 Hz, 1H), 2.07 (s, 3H), 1.53 (s, 3H), 1.34 (s, 3H), 1.09-1.07 (m, 20H); $^{13}$C-NMR (125 MHz, CDCl$_3$) δ 170.0, 138.9, 138.8, 138.6, 138.4, 138.4, 138.3, 138.3, 138.2, 138.2, 138.1, 138.1, 138.0, 137.7, 128.5, 128.4, 128.3, 128.3, 128.2, 128.2, 128.1, 128.1, 128.1, 128.1, 128.0, 127.9, 127.9, 127.8, 127.8, 127.7, 127.6, 127.6, 127.5, 127.5, 127.4, 127.4, 127.4, 127.3, 127.3, 127.2, 127.1, 127.1, 127.0, 110.2, 100.3, 98.9, 98.8, 95.1, 80.8, 80.6, 80.0, 79.8, 79.1, 78.0, 77.0, 76.6, 76.0, 75.4, 75.1, 75.1, 75.0, 74.6, 74.5, 74.3, 73.8, 73.7, 73.3, 73.1, 72.8, 72.2, 72.0, 71.8, 71.8, 71.7, 71.4, 69.6, 68.9, 68.8, 66.3, 63.0, 62.4, 27.5, 25.7, 21.0, 18.0, 17.9, 12.0; MALDI-TOF [M+Na]+ 2285.

Example 11

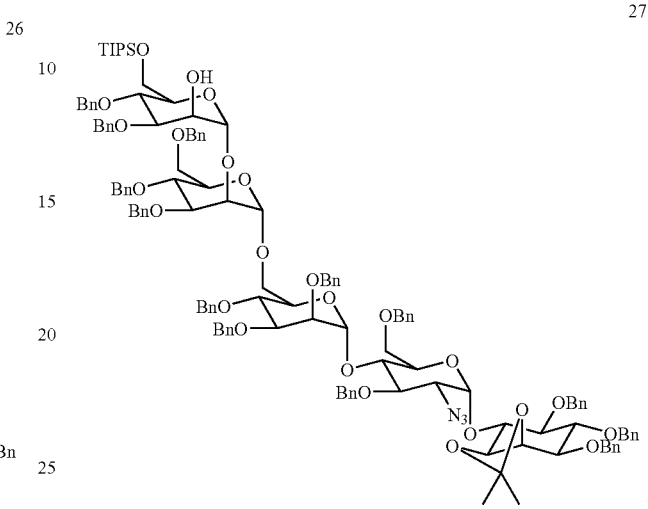

27

O-(3,4-Di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 27. Pentasaccharide 26 (746 mg, 0.33 mmol) was dissolved in $CH_2Cl_2$ (4 mL) and a 0.5 M solution of sodium methoxide in methanol (660 μL, 0.33 mmol) was added. After 2.5 h, the light yellow solution was diluted with $CH_2Cl_2$ (50 mL), washed with sat. aqueous $NaHCO_3$ (2×50 mL) and brine (1×50 mL). Following drying ($Na_2SO_4$), filtration and concentration the crude product was purified by flash silica column chromatography (10→30% EtOAc/hexanes) to afford 27 (604 mg, 83%). $[\alpha]^D_{24}$: +30.6° (c 1.21, $CH_2Cl_2$); IR (thin film) 2358, 2104, 1454, 1045, 696 cm$^{-1}$; $^1$H NMR (500 MHz, CDCl$_3$) δ 7.33-7.03 (m, 59H), 5.56 (d, J=3.7 Hz, 1H), 5.24 (d, J=1.8 Hz, 1H), 5.09 (s, J=1.2 Hz, 1H), 4.87-4.68 (m, 11H), 4.64-4.61 (m, 3H), 4.55-4.28 (m, 16 H), 4.20-4.18 (m, 2H), 4.12-4.01 (m, 7H), 3.95-3.60 (m, 20H), 3.54-3.47 (m, 3H), 3.41-3.37 (m, 4H), 3.28 (dd, J=3.7, 9.8 Hz, 1H), 2.16 (d, J=3.7 Hz, 1H), 1.47 (s, 3H), 1.29 (s, 3H), 1.05-0.97 (m, 23H); $^{13}$C-NMR (125 MHz, CDCl$_3$) δ 138.7, 138.7, 138.6, 138.5, 138.3, 138.3, 138.3, 138.1, 138.1, 138.0, 138.0, 138.0, 137.6, 128.4, 128.4, 128.3, 128.3, 128.3, 128.2, 128.2, 128.1, 128.1, 128.0, 128.0, 127.8, 127.8, 127.7, 127.7, 127.6, 127.6, 127.5, 127.4, 127.4, 127.3, 127.3, 127.2, 127.2, 127.2, 127.1, 127.1, 126.9, 110.1, 100.5, 100.1, 98.9, 95.0, 80.8, 80.6, 80.0, 79.8, 79.7, 79.7, 79.0, 76.9, 76.8, 76.5, 75.9, 75.3, 75.0, 74.9, 74.9, 74.6, 74.4, 74.3, 73.8, 73.7, 73.3, 73.2, 73.1, 73.0, 72.7, 72.2, 72.0, 71.9, 71.9, 71.8, 71.5, 69.6, 68.9, 68.8, 68.5, 66.3, 62.9, 62.6, 27.4, 25.7, 18.0, 18.0, 11.9; MALDI-TOF [M+N]⁺ 2243.

Example 12

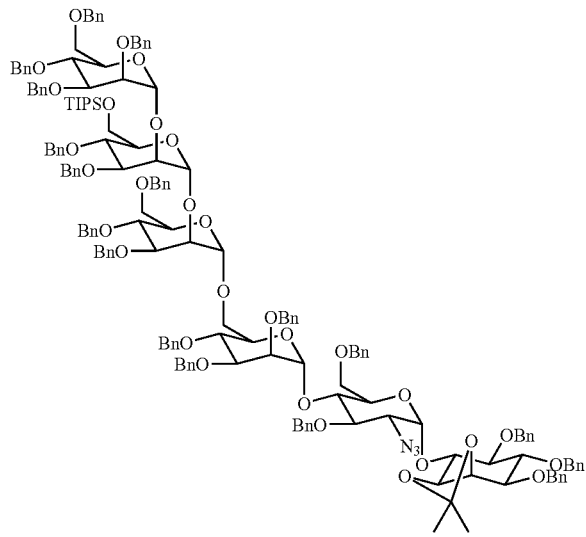

28

O-(2,3,4,6-Tetra-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 28. A mixture of pentasaccharide acceptor 27 (767 mg, 0.35 mmol) and donor 9 (473 mg, 0.69 mmol) were azeotroped with toluene (3×25 mL) and dried under vacuum for 1.5 h. The mixture was dissolved in CH₂Cl₂ (4 mL) and a 0.5 M solution of TMSOTf in CH₂Cl₂ (34 μL, 0.017 mmol) was added. After 30 min, the orange solution was diluted with CH₂Cl₂ (50 mL), washed with sat. aqueous NaHCO₃ (2×50 mL) and brine (1×50 mL). Following drying (Na₂SO₄), filtration and concentration the crude product was purified by flash silica column chromatography (10→40% EtOAc/hexanes) to afford 28 (793 mg, 84%) as a 3.1:1 α:β mixture. IR (thin film) 2863, 2104, 1496, 1454, 735 cm⁻¹; ¹H NMR (500 MHz, CDCl₃) δ 7.39-7.08 (m, 75H), 5.59 (d, J=3.4 Hz, 1H), 5.30-5.21 (m, 2H), 5.06 (d, J=12.2 Hz, 0.6H), 4.94-4.65 (m, 14H), 4.60-4.31 (m, 19H), 4.28-4.18 (m, 4H), 4.16-3.37 (m, 36H), 3.33-3.30 (m, 1H), 3.24-3.20 (m, 0.5H), 1.52 (s, 2H), 1.48 (s, 0.64H), 1.34 (s, 2H), 1.32 (s, 0.88H), 1.05-1.00 (m, 20H); ¹³C-NMR (126 MHz, CDCl₃) δ 140.0, 139.8, 139.8, 139.7, 139.6, 139.6, 139.5, 139.4, 139.3, 139.3, 139.3, 139.2, 139.1, 139.0, 139.0, 138.9, 138.8, 138.8, 138.7, 138.5, 129.5, 129.4, 129.4, 129.3, 129.3, 129.2, 129.2, 129.1, 129.0, 129.0, 129.0, 128.9, 128.9, 128.9, 128.8, 128.8, 128.7, 128.7, 128.6, 128.6, 128.6, 128.5, 128.5, 128.5, 128.4, 128.4, 128.4, 128.3, 128.3, 128.3, 128.2, 128.1, 128.1, 128.0, 127.9, 127.8, 127.8, 127.8, 111.0, 101.1, 100.9, 100.4, 99.8, 95.9, 81.7, 81.5, 81.1, 80.8, 80.7, 79.9, 78.7, 78.1, 78.1, 77.9, 77.7, 77.6, 77.4, 76.8, 76.4, 76.2, 76.2, 75.9, 75.8, 75.8, 75.7, 75.5, 75.5, 75.2, 75.1, 75.0, 75.0, 74.8, 74.6, 74.4, 74.3, 74.2, 74.1, 74.0, 74.0, 73.6, 73.5, 73.3, 73.2, 73.1, 73.0, 72.9, 72.9, 72.8, 72.8, 72.6, 72.3, 71.5, 70.5, 69.7, 69.5, 69.5, 67.0, 63.8, 63.4, 28.3, 28.3, 26.6, 21.7, 19.0, 18.9, 18.9, 18.8, 12.9, 12.8, 12.7; MALDI-TOF [M+Na]⁺ 2767.

Example 13

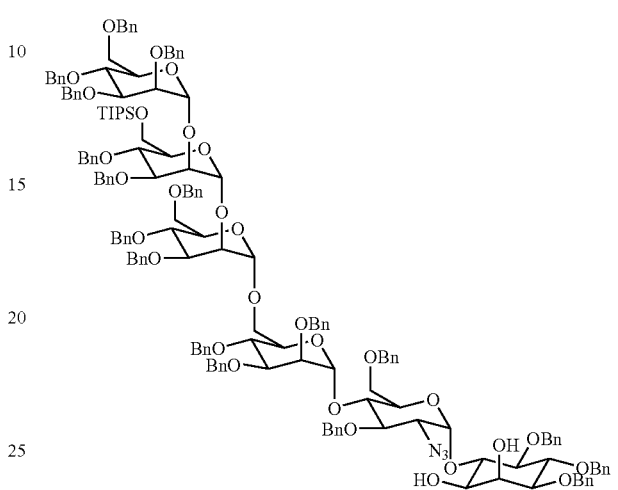

29

O-(2,3,4,6-Tetra-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-α-D-myo-inositol 29. To hexasaccharide 28 (546 mg, 0.20 mmol) in CH₃CN (15 mL)/CH₂Cl₂ (15 mL) was added ethylene glycol (1.55 mL, 0.14 mmol), followed by CSA (276 mg, 1.19 mmol). After 6 h, the clear solution was diluted with CH₂Cl₂ (50 mL), washed with sat. aqueous NaHCO₃ (2×50 mL). The aqueous phase was back extracted with CH₂Cl₂ (2×50 mL), and the combined organic phases were washed with brine (1×50 mL). Following drying (Na₂SO₄), filtration and concentration the crude product was purified by flash silica column chromatography (20→50% EtOAc/hexanes) to afford 28 (131 mg) and 29 (330 mg, 81% based on recovered 28) as a 3.3:1 a mixture. IR (thin film) 3029, 2864, 2106, 1458, 1362 cm⁻¹; ¹H NMR (500 MHz, CDCl₃) δ 7.36-7.07 (m, 75H), 5.56 (m, 0.3H), 5.46 (m, 0.2H), 5.44 (m, 0.2H), 5.41 (d, J=3.4 Hz, 1H), 5.30-5.28 (m, 2H), 5.21 (s, 1H), 5.08-5.03 (m, 0.6H), 4.93-4.60 (m, 16H), 4.58-4.41 (m, 14H), 4.40-4.14 (m, 11H), 4.10-4.06 (m, 1H), 4.02-3.72 (m, 17H), 3.70-3.55 (m, 8H), 3.49-3.32 (m, 10H), 3.22-3.19 (m, 0.42H), 2.95-2.91 (m, 0.43H), 2.52 (s, 1H), 1.02-1.00 (m, 20H): ¹³C-NMR (125 MHz, CDCl₃) δ 139.8, 139.7, 139.6, 139.6, 139.4, 139.3, 139.3, 139.2, 139.2, 139.1, 139.1, 138.8, 138.7, 138.5, 138.3, 138.3, 129.3, 129.3, 129.2, 129.2, 129.1, 129.1, 129.1, 129.0, 129.0, 129.0, 128.9, 128.9, 128.9, 128.8, 128.8, 128.7, 128.7, 128.7, 128.6, 128.6, 128.6, 128.6, 128.5, 128.5, 128.4, 128.2, 128.2, 128.1, 128.1, 128.1, 128.0, 128.0, 128.0, 127.9, 127.8, 127.7, 127.7, 100.8, 100.3, 99.9, 98.8, 82.3, 81.7, 81.4, 81.1, 80.7, 80.6, 80.5, 76.6, 76.0, 75.8, 75.6, 75.5, 75.2, 75.1, 74.9, 74.2, 74.1, 74.0, 74.0, 73.9, 73.5, 73.3, 73.1, 72.9, 72.8, 72.7, 72.7, 72.3, 71.5, 70.4, 69.7, 69.5, 65.0, 18.9, 18.8, 18.8, 12.8, 12.8, 12.7; MALDI-TOF [M+Na]+ 2726.

Example 14

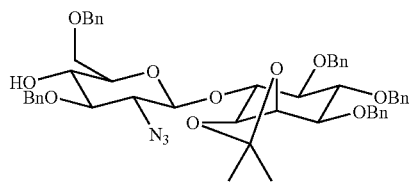

32

O-(2-Azido-3,6-di-O-benzyl-2-deoxy-β-D-glucopyranosyl)-(1→6)-3,4,5-tri-O-benzyl-1,2-O-isopropylidene-D-myo-inositol 32. $[\alpha]^{24}_D$: −38.2° (c 3.88, $CH_2Cl_2$); IR (thin film) 2871, 2361, 2339, 2109, 1071 $cm^{-1}$; $^1$H NMR (500 MHz, $CDCl_3$) δ 7.32-7.16 (m, 22H), 4.87 (d, J=10.7 Hz, 1H), 4.82 (d, J=10.1 Hz, 1H), 4.79 (d, J=11.6 Hz, 1H), 4.75-4.65 (m, 6H), 4.45 (d, J=11.9 Hz, 1H), 4.41 (d, J=11.9 Hz, 1H), 4.16 (at, 3H), 3.98-3.92 (m, 2H), 3.85 (at, 3H), 3.65-3.57 (m, 4H), 3.41 (at, 1H), 3.37 (dd, J=8.3, 10.1 Hz, 1H), 3.28-3.24 (m, 1H), 3.08-3.04 (m, 1H), 2.69 (d, J=1.8 Hz, 1H), 1.41 (s, 3H), 1.25 (s, 3H); $^{13}$C-NMR (100 MHz, $CDCl_3$) δ 139.2, 138.8, 138.7, 138.1, 129.3, 129.2, 129.2, 129.2, 129.2, 128.9, 128.9, 128.7, 128.7, 128.6, 128.6, 128.5, 128.4, 110.6, 101.9, 83.1, 83.1, 81.9, 79.7, 78.1, 77.7, 76.1, 75.9, 75.7, 74.9, 74.5, 74.1, 74.0, 73.4, 71.4, 66.3, 28.5, 26.4; ESI MS m/z (M+Na)+ calcd 880.3780, found 880.3786.

Example 15

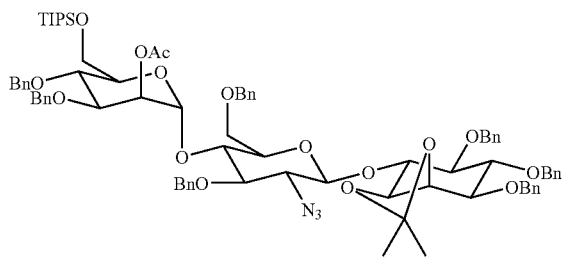

34

O-(2-O-Acetyl-3,4-di-O-benzyl-6-O-triisopropylsilyl-α-D-Mannopyranosyl)-(1→4)-O-(2-azido-3,6-di-O-benzyl-2-deoxy-β-D-glucopyranosyl)-(1→6)-3,4,5-tri-O-benzyl-1,2-O-isopropylidene-D-myo-inositol 34 A mixture of pseudo-disaccharide acceptor 32 (554 mg, 0.65 mmol) and donor 33 (681 mg, 0.97 mmol) were azeotroped with toluene (3×10 mL) and dried under vacuum for 16 h. The mixture was dissolved in $CH_2Cl_2$ (9 mL) and a 0.5 M solution of TMSOTf in $CH_2Cl_2$ (64 μL, 0.032 mmol) was added. After 30 min, the orange solution was diluted with $CH_2Cl_2$ (50 mL), washed with sat. aqueous $NaHCO_3$ (2×50 mL) and brine (1×50 mL). Following drying ($Na_2SO_4$), filtration and concentration the crude product was purified by flash silica column chromatography (3→5% EtOAc/toluene) to afford 34 (604 mg, 67%) as a colorless foam. $[\alpha]^{34}_D$: −8.10° (c 0.68, $CH_2Cl_2$); IR (thin film) 2865, 2361, 2339, 2110, 1741 $cm^{-1}$; $^1$H NMR (500 MHz, $CDCl_3$) δ 7.39-7.19 (m, 32H), 5.37 (dd, J=1.8, 3.0 Hz, 1H), 5.27 (d, J=1.2 Hz, 1H), 4.93 (d, J=11.0 Hz, 1H), 4.90 (d, J=10.4 Hz, 1H), 4.88-4.83 (m, 2H), 4.80-4.69 (m, 6H), 4.65-4.62 (m, 2H), 4.48-4.42 (m, 3H), 4.25 (at, 1H), 4.12-4.04 (m, 2H), 4.01 (at, 1H), 3.94 (at, 1H), 3.87-3.82 (m, 3H), 3.74-3.71 (m, 1H), 3.68-3.61 (m, 3H), 3.55-3.46 (m, 3H), 3.29-3.22 (m, 2H), 1.95 (s, 3H), 1.49 (s, 3H), 1.31 (s, 3H), 1.04 (s, 21H); $^{13}$C-NMR (125 MHz, $CDCl_3$) δ 170.0, 138.8, 138.4, 138.1, 138.0, 138.0, 137.7, 128.5, 128.4, 128.4, 128.4, 128.3, 128.3, 128.3, 128.2, 128.1, 128.0, 128.0, 128.0, 128.0, 128.0, 127.9, 127.9, 127.8, 127.8, 127.6, 127.6, 127.5, 127.4, 127.4, 127.4, 109.8, 101.1, 98.5, 83.4, 82.4, 81.2, 78.8, 77.9, 76.8, 75.2, 75.2, 75.1, 74.4, 74.4, 74.1, 73.7, 73.5, 73.4, 73.4, 73.2, 71.7, 69.2, 68.8, 66.2, 61.9, 27.6, 25.6, 20.7, 18.0, 17.9, 12.0; ESI MS m/z (M+Na)+ calcd 1420.6687, found 1420.6693.

Example 16

36

O-(2,3,4-Tri-O-benzyl-6-O-triisopropylsilyl-α-D-mannopyranosyl)-(1→4)-O-(2-azido-3,6-di-O-benzyl-2-deoxy-β-D-glucopyranosyl)-(1→6)-3,4,5-tri-O-benzyl-1,2-O-isopropylidene-D-myo-inositol 36. Trisaccharide 34 (600 mg, 0.43 mmol) was dissolved in $CH_2Cl_2$ (5 mL) and a 0.75 M solution of sodium methoxide in methanol (571 μL, 0.43 mmol) was added. After 1.5 h, the clear solution was diluted with $CH_2Cl_2$ (50 mL), washed with sat. aqueous aq. $NaHCO_3$ (2×50 mL) and brine (1×50 mL). Following drying ($Na_2SO_4$), filtering, and concentration the crude product was dissolved in DMF (5 mL) and benzyl bromide (78 μL, 0.65 mmol) was added. The clear solution was cooled to 0° C., and NaH (60% dispersion in mineral oil, 26 mg, 0.65 mmol) was added in one portion. After 14 h, MeOH (5 mL) was added, and the mixture was poured into $H_2O$ (50 mL) and washed with $Et_2O$ (3×50 mL). The combined organic phases were washed with brine (1×50 mL), dried ($Na_2SO_4$), filtered and concentrated. Purification by flash silica column chromatography (0→8% EtOAc/toluene) afforded 36 (386 mg, 62%). $[\alpha]^{24}_D$: −11.0° (c 1.07, $CHCl_3$); IR (thin film) 2865, 2361, 2338, 2110, 1067 $cm^{-1}$; $^1$H NMR ($CDCl_3$) δ 7.40-7.15 (m, 45H), 5.22 (d, J=1.0 Hz, 1H), 4.93 (d, J=10.7 Hz, 1H), 4.91-4.87 (m, 2H), 4.84 (d, J=9.5 Hz, 1H), 4.80 (d, J=3.4 Hz, 1H), 4.78-4.73 (m, 4H), 4.65 (d, J=10.7 Hz, 1H), 4.58 (d, J=11.9 Hz, 1H), 4.55-4.49 (m, 3H), 4.41 (d, J=11.6 Hz, 1H), 4.39 (d, J=12.2 Hz, 1H), 4.28-4.25 (m, 2H), 4.12-4.05 (m, 3H), 3.95 (at, 1H), 3.86 (dd, J=3.7, 11.0 Hz, 1H), 3.82-3.79 (m, 1H), 3.76-3.67 (m, 6H), 3.57 (dd, J=2.1, 9.5 Hz, 1H), 3.52-3.46 (m, 2H), 3.30-3.27 (m, 1H), 3.14 (at, 1H), 1.51 (s, 3H), 1.33 (s, 3H), 1.10-0.99 (m, 26H); $^{13}$C-NMR (100 MHz, $CDCl_3$) δ 138.9, 138.8, 138.6, 138.6, 138.3, 138.2, 138.1, 128.5, 128.5, 128.5, 128.4, 128.4, 128.4, 128.2, 128.1, 128.1, 128.0, 127.9, 127.7, 127.6, 127.3, 127.1, 110.0, 101.2, 99.9, 83.2, 82.5, 81.3, 79.7, 78.9, 77.0, 76.9, 76.0, 75.3, 75.2, 75.1, 74.9, 74.3, 74.3, 74.3, 74.2, 73.4, 73.3, 72.2, 72.1, 69.5, 66.1, 62.6, 27.7, 25.8, 18.1, 18.1, 12.1; ESI MS m/z (M+Na)+ calcd 1468.7051, found 1468.7059.

Example 17

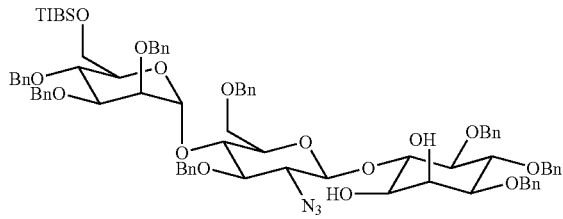

37

O-(2,3,4-Tri-O-benzyl-6-O-tert-butyldimethylsilyl-α-D-mannopyranosyl)-(1→4)-O-(2-azido-3,6-di-O-benzyl-2-deoxy-β-D-glucopyranosyl)-(1→6)-3,4,5-tri-O-benzyl-D-myo-inositol 37. Trisaccharide 36 (375 mg, 0.26 mmol) was dissolved in $CH_2Cl_2$ (4 mL) and a 0.5 M solution of HCl in MeOH (9.2 mL, 4.61 mmol) was added. After 8 h, the yellow solution was concentrated several times with $CH_2Cl_2$, then diluted with $CH_2Cl_2$ (50 mL) and washed with $H_2O$ (2×50 mL), sat. aqueous $NaHCO_3$ (2×50 mL), and brine (1×50 mL). Following drying ($Na_2SO_4$), filtering, and concentration the crude product was dissolved in $CH_2Cl_2$ (3 mL). Imidazole (35 mg, 0.52 mmol) and tert-butyldimethylchlorosilane (59 mg, 0.39 mmol) were added, and the cloudy suspension was stirred at room temperature for 1.5 h. MeOH (5 mL) was added, and the solution was diluted with $CH_2Cl_2$ (50 mL), and washed with sat. aqueous aq. $NaHCO_3$ (2×50 mL), and brine (1×50 mL). Following drying ($Na_2SO_4$), filtering, and concentration the crude product was purified by flash silica column chromatography (5→15% EtOAc/toluene) to afford 37 (258 mg, 73%) as a colorless oil. $[\alpha]^{24}_D$: −2.47° (c 1.74, $CH_2Cl_2$); IR (thin film) 2926, 2111, 1454, 1361, 1111 cm$^{-1}$; $^1$H NMR (500 MHz, $CDCl_3$) δ 7.33-7.11 (m, 33H), 5.19 (d, J=2.1 Hz, 1H), 4.95 (d, J=11.0 Hz, 1H), 4.92 (d, J=10.4 Hz, 1H), 4.83-4.80 (m, 3H), 4.75 (d, J=10.7 Hz, 1H), 4.72 (d, J=12.2 Hz, 1H), 4.67 (d, J=11.9 Hz, 1H), 4.59-4.46 (m, 7H), 4.41 (d, J=11.6 Hz, 1H), 4.37 (d, J=12.2 Hz, 1H), 4.22 (d, J=12.2 Hz, 1H), 4.18 (at, 1H), 4.02 (d, J=9.5 Hz, 1H), 4.00-3.91 (m, 3H), 3.78-3.63 (m, 8H), 3.53-3.49 (m, 2H), 3.45-3.38 (m, 4H), 3.23 (app t, 1H), 2.45 (s, 1H), 0.82 (s, 9H), −0.01 (s, 3H), −0.02 (s, 3H); $^{13}$C-NMR (100, MHz, $CDCl_3$) δ 138.7, 138.6, 138.5, 138.0, 137.9, 137.7, 129.1, 128.5, 128.5, 128.5, 128.4, 128.4, 128.4, 128.1, 128.1, 128.0, 127.9, 127.8, 127.7, 127.6, 127.2, 127.1, 101.9, 100.0, 82.9, 82.6, 82.1, 81.5, 79.5, 79.4, 76.1, 75.9, 75.8, 75.5, 75.0, 74.6, 74.4, 74.2, 73.5, 72.4, 72.3, 72.2, 70.6, 69.0, 68.9, 66.3, 62.4, 26.0, 18.4, −5.0, −5.2; ESI MS m/z (M+Na)+ calcd 1386.6268, found 1386.6255.

Example 18

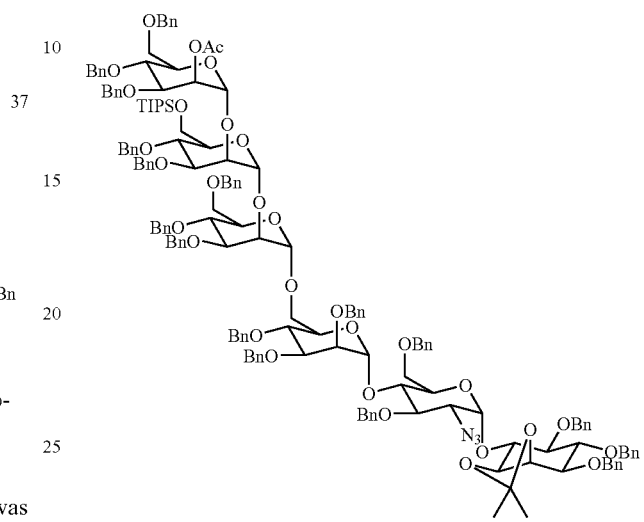

38

O-(2-O-Acetyl-3,4,6-tri-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 38. A mixture of pentasaccharide acceptor 27 (454 mg, 0.20 mmol) and donor 7 (260 mg, 0.41 mmol) were azeotroped with toluene (3×7 mL) and dried under vacuum for 16 h. The mixture was dissolved in $CH_2Cl_2$ (3 mL) and a 0.5 M solution of TMSOTf in $CH_2Cl_2$ (20 μL, 0.010 mmol) was added. After 30 min, the orange solution was diluted with $CH_2Cl_2$ (50 mL), washed with sat. aqueous $NaHCO_3$ (2×50 mL) and brine (1×50 mL). Following drying ($Na_2SO_4$), filtering and concentration the crude product was purified by flash silica column chromatography (10→40% EtOAc/hexanes) to afford 38 (560 mg, quant.) as a colorless oil. $[\alpha]^{24}_D$: +52.1° (c 0.42, $CH_2Cl_2$); IR (thin film) 2863, 2361, 2105, 1734, 1050 cm$^{-1}$; $^1$H NMR (500 MHz, $CDCl_3$) δ 7.37-6.96 (m, 83H), 5.58 (d, J=3.7 Hz, 1H), 5.54 (app s, 1H), 5.27 (app s, 1H), 5.26 (app s, 1H), 5.02 (app s, 1H), 4.88-4.72 (m, 13H), 4.67 (app t, 2H), 4.56-4.31 (m, 18H), 4.26-4.09 (m, 10H), 4.06-4.00 (m, 4H), 3.97-3.64 (m, 20H), 3.60-3.34 (m, 11H), 3.32-3.29 (m, 1H), 2.10 (s, 3H), 1.50 (s, 3H), 1.25 (s, 3H), 1.07-1.00 (m, 22H): HSQC data $^{13}$C (125 MHz)/$^1$H (500 MHz): 100.0/5.03 (1a), 68.9/5.56 (2a), 78.9/3.98 (3a), 68.9/3.59, 3.43 (6a), 100.1/5.28 (1b), 75.6/4.05 (2b), 99.2/4.81 (1c), 72.8/4.14 (2c), 100.5/5.27 (1d), 80.2/3.76 (3d), 66.3/3.89, 3.37 (6d), 95.3/5.60 (1e), 63.2/3.32 (2e), 77.2/4.12 (4e); HMBC cross peaks $^{13}$C (125

MHz): 75.6 (a→b), 72.8 (b→c), 66.3 (c→d), 77.2 (d→e); ESI MS m/z (M+Na)+ calcd 2717.2497, found 2717.2450.

Example 19

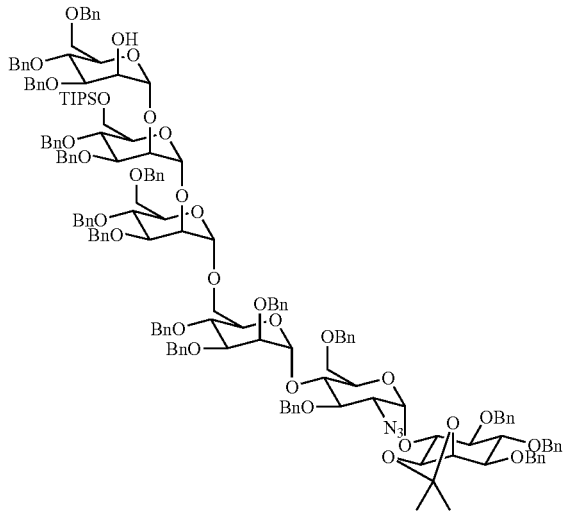

39

O-(3,4,6-Tri-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,6-tri-O-benzyl-1,2-O-isopropylidene-D-myo-inositol 39. Hexasaccharide 38 (560 mg, 0.21 mmol) was dissolved in $CH_2Cl_2$ (3 mL) and a 0.75 M solution of sodium methoxide in methanol (278 μL, 0.21 mmol) was added. After 3 h, the light yellow solution was diluted with $CH_2Cl_2$ (50 mL), washed with sat. aqueous $NaHCO_3$ (2×50 mL) and brine (1×50 mL). Following drying ($Na_2SO_4$), filtering and concentration the crude product was purified by flash silica column chromatography (2.5→12.5% EtOAc/toluene) to afford 39 (396 mg, 72%). $[α]^{24}_D$: +62.3° (c 0.30, $CH_2Cl_2$); IR (thin film) 2361, 2338, 2104, 1261, 1050 cm$^{-1}$; $^1$H NMR (500 MHz, CDCl$_3$) δ 7.37-6.97 (m, 85H), 5.57 (d, J=3.7 Hz, 1H), 5.29 (app s, 1H), 5.24 (d, J=1.5 Hz, 1H), 5.13 (app s, 1H), 4.89-4.63 (m, 18H), 4.54-4.32 (m, 19H), 4.30-4.20 (m, 5H), 4.16-4.01 (m, 11H), 3.94-3.33 (m, 36H), 3.30 (dd, J=3.7, 10.1 Hz, 1H), 2.37 (d, J=2.1 Hz, 1H), 1.50 (s, 3H), 1.32 (s, 3H), 1.08-1.00 (m, 24H); $^{13}$C-NMR (125 MHz, CDCl$_3$) δ 138.9, 138.8, 138.7, 138.6, 138.4, 138.4, 138.2, 138.2, 138.2, 138.1, 138.1, 138.1, 138.0, 137.9, 137.8, 137.6, 128.6, 128.5, 128.5, 128.4, 128.4, 128.3, 128.3, 128.3, 128.3, 128.2, 128.2, 128.2, 128.1, 128.1, 128.1, 128.1, 128.0, 128.0, 128.0, 127.9, 127.9, 127.8, 127.8, 127.8, 127.8, 127.8, 127.7, 127.7, 127.7, 127.7, 127.6, 127.6, 127.6, 127.6, 127.5, 127.5, 127.5, 127.4, 127.4, 127.4, 127.4, 127.2, 127.2, 127.2, 127.1, 127.1, 127.0, 126.9, 126.8, 110.1, 101.2, 100.3, 100.0, 98.9, 95.0, 80.8, 80.6, 80.3, 79.9, 79.6, 79.0, 77.2, 76.9, 76.9, 76.6, 76.5, 75.9, 75.3, 75.0, 74.9, 74.8, 74.7, 74.6, 74.3, 74.0, 73.7, 73.5, 73.4, 73.3, 73.3, 73.2, 73.1, 73.0, 72.7, 72.7, 72.3, 72.2, 72.1, 72.0, 71.9, 71.8, 71.8, 71.4, 71.3, 69.6, 68.9, 68.6, 68.4, 68.3, 66.1, 62.9, 62.4, 27.4, 25.7, 18.1, 18.1, 11.8; ESI MS m/z (M+Na)+ calcd 2675.2391, found 2675.2380.

Example 20

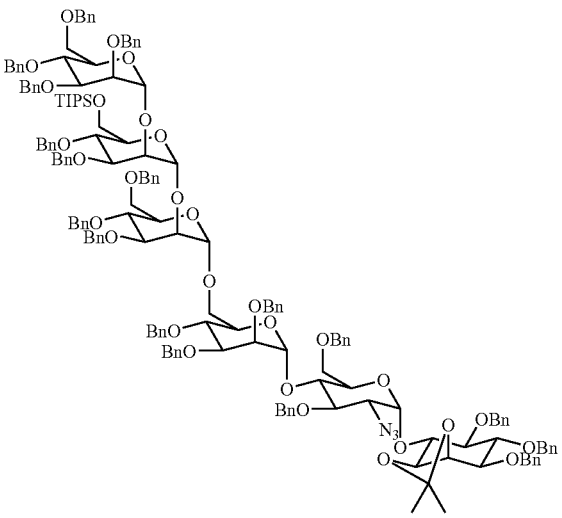

40

O-(2,3,4,6-Tetra-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,6-tri-O-benzyl-1,2-O-isopropylidene-D-myo-inositol 40. Pseudo-hexasacharide 39 (70 mg, 0.026 mmol) was dissolved in DMF (2 mL) and benzyl bromide (5 μL, 0.040 mmol) was added. The clear solution was cooled to 0° C., and NaH (60% dispersion in mineral oil, 2 mg, 0.040 mmol) was added in one portion. After 1 h, MeOH (5 mL) was added, and the mixture was poured into $H_2O$ (50 mL) and washed with $Et_2O$ (3×50 mL). The combined organic phases were washed with brine (1×50 mL), dried ($Na_2SO_4$), filtered and concentrated. Purification by flash silica column chromatography (1.5→7.5% EtOAc/toluene) afforded 40 (68 mg, 96%). $[α]^{24}_D$: +46.0° (c 0.10, $CH_2Cl_2$); IR (thin film) 2863, 2104, 1496, 1454, 735 cm$^{-1}$; $^1$H NMR (500 MHz, CDCl$_3$) δ 7.37-6.95 (m, 90H), 5.57 (d, J=2.7 Hz, 1H), 5.28 (app s, 1H), 5.24 (app s, 1H), 5.20 (app s, 1H), 4.89-4.64 (m, 15H), 4.58-4.30 (m, 20H), 4.25-4.20 (m, 5H), 4.16-4.04 (m, 8H), 4.00-3.34 (m, 35H), 3.31-3.29 (m, 1H), 1.50 (s, 3H), 1.32 (s, 3H), 1.03-1.00 (m, 20H); $^{13}$C-NMR (125 MHz, CDCl$_3$) δ 140.0, 139.8, 139.8, 139.7, 139.6, 139.6, 139.5, 139.4, 139.3, 139.3, 139.3, 139.2, 139.1, 139.0, 139.0, 138.9, 138.8, 138.8, 138.7, 138.5, 129.5, 129.4, 129.4, 129.3, 129.3, 129.2, 129.2, 129.1, 129.0, 129.0, 129.0, 128.9, 128.9, 128.9, 128.8, 128.8, 128.7, 128.7, 128.6, 128.6, 128.6, 128.5, 128.5, 128.5, 128.4, 128.4, 128.4, 128.3, 128.3, 128.3, 128.2, 128.1, 128.1, 128.0, 127.9, 127.8, 127.8, 127.8, 111.0, 101.1, 100.9, 100.4, 99.8, 95.9, 81.7, 81.5, 81.1, 80.8, 80.7, 79.9, 78.7, 78.1, 78.1, 77.9, 77.8, 77.7, 77.6, 77.4, 76.8, 76.4, 76.2, 76.2, 75.9, 75.8, 75.8, 75.7, 75.5, 75.5, 75.2, 75.1, 75.0, 75.0, 74.8, 74.6, 74.4, 74.3, 74.2, 74.1, 74.0, 74.0, 73.6, 73.5, 73.3, 73.2, 73.1, 73.1, 73.0, 72.9, 72.9, 72.8, 72.8, 72.6, 72.3, 71.5, 70.5, 69.7, 69.5, 69.5, 67.0, 63.8, 63.4, 28.3, 28.3, 26.6, 21.7, 19.0, 18.9, 12.7; ESI MS m/z (M+2Na)$^{2+}$ calcd 1394.1377, found 1394.1358.

Example 21

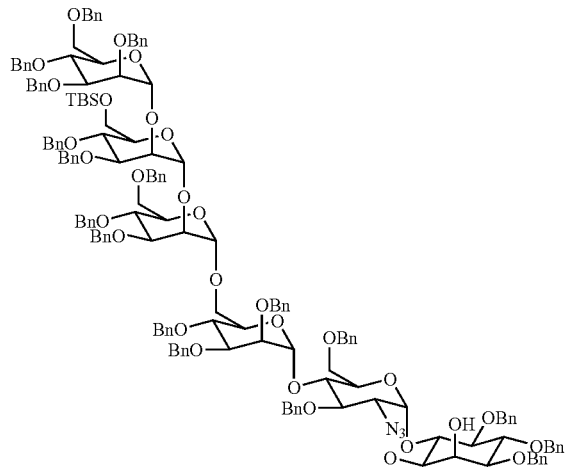

41

O-(2,3,4,6-Tetra-O-benzyl-α-D-mannopyranosyl)-(1→2)-O-(3,4-di-O-benzyl-6-O-tert-butyldimethylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-D-myo-inositol 41. Pseudo-hexasaccharide 40 (240 mg, 0.088 mmol) was dissolved in CH$_2$Cl$_2$ (1.5 mL) and a 0.5 M solution of HCl in MeOH (3.0 mL, 1.49 mmol) was added. After 14 h, the yellow solution was concentrated several times with CH$_2$Cl$_2$, then diluted with CH$_2$Cl$_2$ (50 mL) and washed with H$_2$O (2×50 mL), sat. aqueous aq. NaHCO$_3$ (2×50 mL), and brine (1×50 mL). Following drying (Na$_2$SO$_4$), filtering, and concentration the crude product was dissolved in CH$_2$Cl$_2$ (2 mL). Imidazole (12 mg, 0.18 mmol) and tert-butyldimethylchlorosilane (20 mg, 0.13 mmol) were added, and the cloudy suspension was stirred at room temperature for 40 minutes. MeOH (5 mL) was added, and the solution was diluted with CH$_2$Cl$_2$ (50 mL), and washed with sat. aqueous aq. NaHCO$_3$ (2×50 mL), and brine (1×50 mL). Following drying (Na$_2$SO$_4$), filtering, and concentration the crude product was purified by flash silica column chromatography (10→20% EtOAc/toluene) to afford 41 (156 mg, 67%) as a colorless oil. [α]$^{24}_D$: +44.6° (c 1.0, CH$_2$Cl$_2$); IR (thin film) 2926, 2361, 2338, 2106, 1052 cm$^{-1}$; $^1$H NMR (500 MHz, CDCl$_3$) δ 7.30-6.93 (m, 86H), 5.36 (d, J=3.7 Hz, 1H), 5.22 (d, J=1.8 Hz, 1H), 5.19 (s, 2H), 4.88-4.80 (m, 7H), 4.75-4.67 (m, 7H), 4.63-4.58 (m, 3H), 4.55-4.35 (m, 17H), 4.29-4.15 (m, 11H), 4.11-4.01 (m, 2H), 3.96-3.53 (m, 30H), 3.45-3.27 (m, 12H), 2.47 (s, 1H), 0.79 (m, 9H), −0.03 (s, 3H), −0.04 (s, 3H); $^{13}$C-NMR (125 MHz, CDCl$_3$) δ 138.8, 138.7, 138.6, 138.4, 138.4, 138.3, 138.3, 138.3, 138.2, 138.0, 137.8, 137.6, 137.5, 128.7, 128.5, 128.4, 128.3, 128.3, 128.2, 128.2, 128.2, 128.1, 128.0, 128.0, 128.0, 127.9, 127.9, 127.8, 127.8, 127.8, 127.8, 127.7, 127.7, 127.7, 127.6, 127.5, 127.5, 127.5, 127.4, 127.4, 127.4, 127.3, 127.3, 127.2, 127.2, 127.2, 127.1, 127.0, 127.0, 126.8, 100.1, 100.0, 99.3, 99.0, 97.9, 81.4, 80.9, 80.6, 80.1, 79.8, 79.7, 79.6, 79.5, 77.2, 76.6, 75.8, 75.1, 74.9, 74.8, 74.6, 74.5, 74.3, 74.0, 73.2, 73.2, 73.1, 72.7, 72.6, 72.5, 72.2, 72.1, 72.0, 71.9, 71.3, 70.6, 69.5, 68.9, 68.6, 66.1, 64.1, 62.1, 26.0, 18.2, −4.8, −5.5; ESI MS m/z (M+2Na)$^{2+}$ calcd 1353.0985, found 1353.0998

Example 22

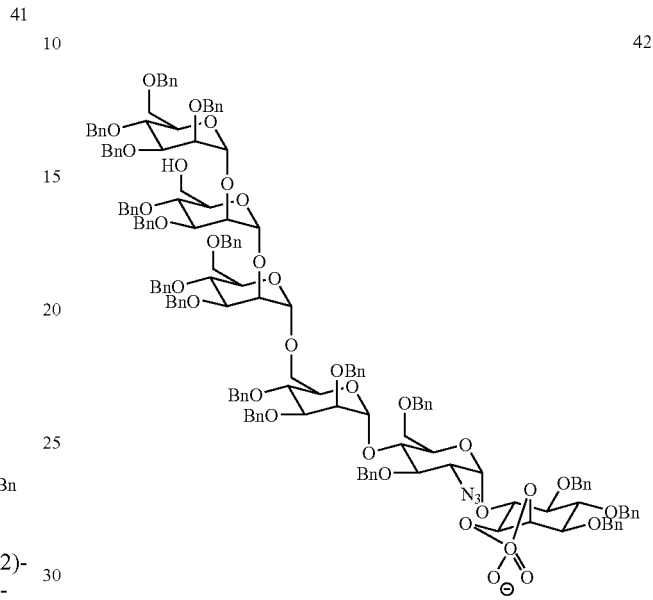

42

O-(2,3,4,6-Tetra-O-benzyl-α-D-mannopyranosyl)-(1→2)-O-(3,4-di-O-benzyl-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-cyclic phosphate-D-myo-inositol 42. To pyridine (2 mL) was added methyl dichlorophosphate (48 μL, 0.48 mmol). After 15 min another aliquot of methyl dichlorophosphate (48 μL, 0.48 mmol) was added, and the resulting white cloudy solution was stirred for 30 min. Hexasaccharide diol 41 (127 mg, 0.048 mmol) In pyridine (2 mL) was added via cannula, and the resulting cloudy yellow solution was stirred for 50 min, then quenched with sat. aqueous NaHCO$_3$ (1.0 mL). The solution was concentrated in vacuo, taken up in H$_2$O (80 mL), acidified with 2.0 M HCl until the solution reached pH 1, then extracted with EtOAc (4×50 mL). The combined organic phases were dried (Na$_2$SO$_4$), filtered and concentrated to yield a white foam. The crude cyclic phosphate was taken up in THF (3 mL) and a 1.0 M solution of TBAF in THF (130 μL, 0.13 mmol) was added. The light yellow solution was stirred at room temperature for 14 h, then concentrated in vacuo. Purification by flash silica column chromatography (100:7:1 CH$_2$Cl$_2$:MeOH:30% NH$_3$) afforded 42 (80 mg, 70%) as a colorless oil. [α]$^{24}_D$: +54.5° (c 0.44, CH$_2$Cl$_2$); IR (thin film) 3028, 2924, 2106, 1453, 1361 cm$^{-1}$; $^1$H NMR (500 MHz, DMSO-d$^6$) δ 7.42-6.87 (m, 75H), 5.52 (s, 1H), 5.21-5.10 (m, 3H), 4.94-4.91 (m, 1H), 4.85-4.04

(m, 39H), 3.92-3.14 (m, 39H) $^{31}$P NMR (120 MHz, CDCl$_3$) δ 14.3; ESI MS m/z (M+2Na)$^{2+}$ calcd 1338.0241, found 1338.0235.

Example 23

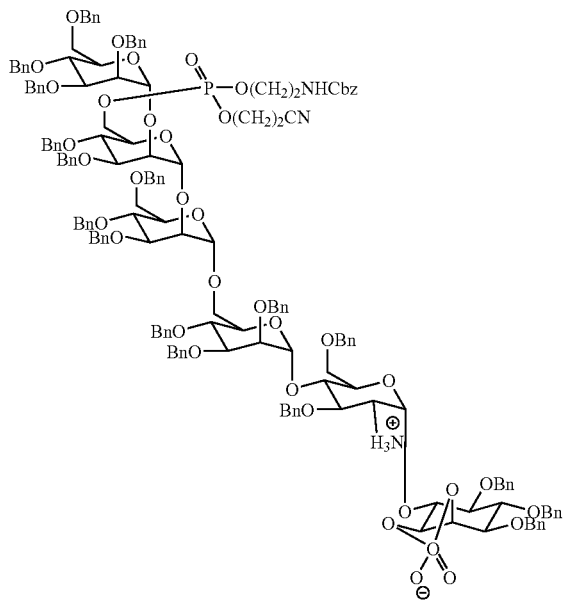

43

O-(2,3,4,6-Tetra-O-benzyl-α-D-mannopyranosyl)-(1→2)-O-(3,4-di-O-benzyl-O-(6-(2-[N-(benzyloxycarbonyl)amino]ethyl 2'-cyanoethyl phosphate-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-cyclic phosphate-D-myo-inositol 43. A mixture of hexasaccharide cyclic phosphate acceptor 42 (165 mg, 0.063 mmol) and phosphoramidite (174 mg, 0.44 mmol) were azeotroped with toluene (3×6 mL) and dried under vacuum for 3 h. A 1:1 mixture of CH$_3$CN:CH$_2$Cl$_2$ (8 ml) was added, followed by sublimed 1H-tetrazole (31 mg, 0.44 mmol). The slightly opaque solution was stirred at room temperature for 3 h, at which time TLC analysis showed complete consumption of the acceptor. A 70% wt. solution of tert-butyl hydroperoxide (86 μL, 0.63 mmol) was added, and the resulting clear solution was stirred at room temperature for 2 h. The mixture was diluted with CH$_2$Cl$_2$ (50 mL), washed with sat. aqueous NaHCO$_3$ (2×50 mL) and brine (1×50 mL). Following drying (Na$_2$SO$_4$), filtration and concentration the crude product was purified by flash silica column chromatography (93:6:1 CH$_2$Cl$_2$:MeOH:30% NH$_3$) to afford 43 (156 mg, 84%) as a mixture of diastereomers; IR (thin film) 2922, 2362, 1718, 1454, 1362 cm$^{-1}$; $^1$H NMR (500 MHz, DMSO-d$^6$) δ 7.34-7.04 (m, 80H), 5.40-5.12 (m, 3H), 5.02-4.90 (m, 5H), 4.80-3.16 (m, 87H), 2.50-2.49 (m, 2H); $^{31}$P NMR (120 MHz, CDCl$_3$) δ 13.6, −0.95, −1.18; MALDI-TOF [M+Na+K]$^+$ 2981.

Example 24

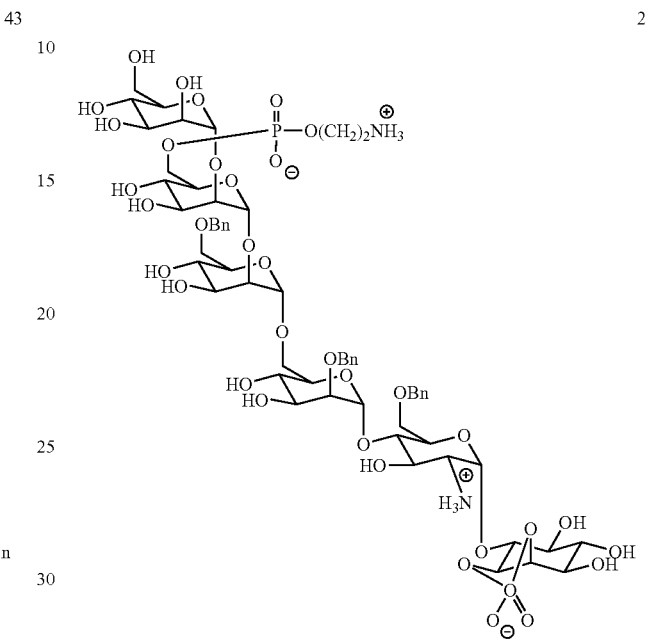

2

O-(α-D-Mannopyranosyl)-(1→2)-O-(6-(2-aminoethyl hydrogen phosphate-α-D-mannopyranosyl)-(1→2)-O-(α-D-mannopyranosyl)-(1→6)-O-(α-D-mannopyranosyl)-(1→4)-O-(2-amino-2-deoxy-α-D-glucopyranosyl)-(1→6)-1,2-cyclic phosphate-D-myo-inositol 2. Bis-phosphate 43 (144 mg, 0.049 mmol) was dissolved in CH$_2$Cl$_2$ (2 mL) and DBU (22 μL, 0.147 mmol) was added dropwise. The yellowish solution was stirred at room temperature for 2 h, then diluted with CH$_2$Cl$_2$ (50 mL), washed with sat. aqueous NaHCO$_3$ (2×50 mL) and brine (1×50 mL). Following drying (Na$_2$SO$_4$) the crude product was flushed through a pad of silica. The silica was washed with 93:6:1 CH$_2$Cl$_2$:MeOH:30% NH$_3$ (100 mL), and the combined washed concentrated to give the crude product as an oil. Ammonia (2 mL) was condensed in a flame-dried 3-neck flask. Following cooling to −78° C., sodium metal (ca. 20 mg) was added and the resultant dark blue solution was stirred for 5 min. THF (1 mL) was added, followed by crude diphosphate in THF (2 mL) via cannula. The blue solution was stirred at −78° C. for 15 min (blue color must not disappear!), then NH$_4$Cl was added dropwise. Following disappearance of the blue color, MeOH (20 mL) was added. The flask was warmed to room temperature, concentrated to ca. 30 mL, and added to a silica column of 3:3:2 CH$_2$Cl$_2$:MeOH:30% NH$_3$. The column was washed with 200 mL of 3:3:2 CH$_2$Cl$_2$:MeOH:30% NH$_3$, then concentrated to a white solid. The crude product was further purified by flash silica column chromatography (2:2:2:1 BuOH:EtOH:H$_2$O:30% NH$_3$) to yield 2 (18.0 mg, 75%) as a white powder following concentration and lyophilization (H$_2$O). IR (thin film) 3144, 3051, 1407, 1118 cm$^{-1}$; $^1$H NMR (500 MHz, D$_2$O) δ 7.38 (s, 1H), 5.54 (d, J=6.1 Hz, 1H), 5.28 (s, 1H), 5.15 (s, 1H), 5.07-5.03 (m, 3H), 4.67 (t, J=4.6 Hz, 1H), 4.41 (s, 1H), 4.34-4.27 (m, 1H), 4.20-4.17 (m, 1H), 4.10-3.58 (m, 34

H), 3.57-3.53 (m, 1H), 3.38 (at, 1H), 3.27-3.25 (m, 2H), 2.07 (s, 1H), 1.20 (bs, 1H); $^{31}$P NMR (120 MHz, D$_2$) 516.0, 0.38; MALDI-TOF [M+2H+Na+K]$^+$ 1238.

Example 25

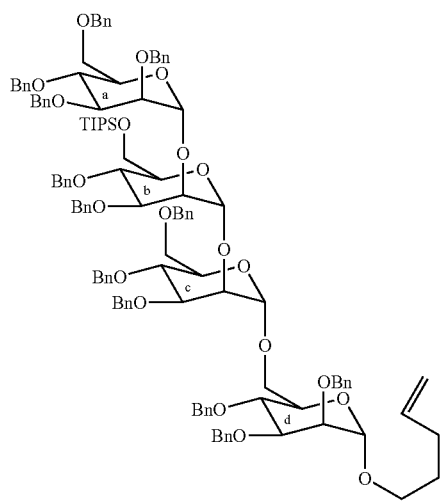

n-Pentenyl 2,3,4,6-tetra-O-benzyl-α-D-mannopyranosyl-(1→2)-3,4-di-O-benzyl-6-O-trisopropylsilyl-α-D-mannopyranosyl-(1→2)-3,4,6-tri-O-benzyl-α-D-mannopyranosyl-(1→6)-2,3,4-tri-O-benzyl-α-D-mannopyranoside 46. Octenediol functionalized resin 48 (50 μmol, 50 mg, 1.00 mmol/g loading) was loaded into a reaction vessel and inserted into a modified ABI-433A peptide synthesizer. The resin was glycosylated using donor 6 (5 equiv., 0.25 mmol, 160 mg loaded into cartridges) delivered in CH$_2$Cl$_2$ (3 mL) and TMSOTf (0.5 equiv., 2.0 mL, 0.0125 M TMSOTf in CH$_2$Cl$_2$) at room temp. Mixing of the suspension was performed (10 s vortex, 50 s rest) for 15 min. The resin was then washed with CH$_2$Cl$_2$ (6×4 mL each), and the glycosylation was repeated (double glycosylation). Deprotection of the acetyl ester was carried out by treating the glycosylated resin with sodium methoxide (8 equiv., 0.5 mL, 0.75 M NaOMe in MeOH) in CH$_2$Cl$_2$ (5 mL) for 30 min at room temp. The resin was then washed with CH$_2$Cl$_2$ (1×4 mL) and subjected to the deprotection conditions a second time for 30 min. The deprotected polymer-bound C6-OH monosaccharide was then glycosylated using donor 7 (5 equiv., 0.25 mmol, 160 mg loaded into cartridges) delivered in CH$_2$Cl$_2$ (3 mL) and TMSOTf (0.5 equiv., 2.0 mL, 0.0125 M TMSOTf in CH$_2$Cl$_2$) at room temp. The resin was then washed with CH$_2$Cl$_2$ (6×4 mL each), and the glycosylation was repeated (double glycosylation). Deprotection of the acetyl ester was carried out by treating the glycosylated resin with sodium methoxide (8 equiv., 0.5 mL, 0.75 M NaOMe in MeOH) in CH$_2$Cl$_2$ (5 mL) for 30 min at room temp. The resin was then washed with CH$_2$Cl$_2$ (1×4 mL) and subjected to the deprotection conditions a second time for 30 min. The deprotected polymer-bound disaccharide was then glycosylated using donor 8 (5 equiv., 0.25 mmol, 175 mg loaded into cartridges) delivered in CH$_2$Cl$_2$ (3 mL) and TMSOTf (0.5 equiv., 2.0 mL, 0.0125 M TMSOTf in CH$_2$Cl$_2$) at room temp. Mixing of the suspension was performed (10 s vortex, 50 s rest) for 15 min. The resin was then washed with CH$_2$Cl$_2$ (6×4 mL each), and the glycosylation was repeated (double glycosylation). Deprotection of the acetyl ester was carried out by treating the glycosylated resin with sodium methoxide (8 equiv., 0.5 mL, 0.75 M NaOMe in MeOH) in CH$_2$Cl$_2$ (5 mL) for 30 min at room temp. The resin was then washed with CH$_2$Cl$_2$ (1×4 mL) and subjected to the deprotection conditions a second time for 30 min. The polymer-bound trisaccharide was then glycosylated using donor 9 (5 equiv., 0.25 mmol, 171 mg loaded into cartridges) delivered in CH$_2$Cl$_2$ (3 mL) and TMSOTf (0.5 equiv., 2.0 mL, 0.0125 M TMSOTf in CH$_2$Cl$_2$) at room temp. Mixing of the suspension was performed (10 s vortex, 50 s rest) for 15 min. The resin was then washed with CH$_2$Cl$_2$ (6×4 mL each) and vessel was removed from the synthesizer.

The glycosylated resin (50 μmol) was dried in vacuo over phosphorous pentoxide for 12 h and transferred to a round bottom flask. The flask was purged with ethylene and Grubbs' catalyst (bis(tricyclohexylphosphine)benzylidine ruthenium (IV) dichloride, 12 mg, 30 mol %) was added. The reaction mixture was diluted with CH$_2$Cl$_2$ (3 mL) and stirred under 1 atm ethylene for 36 h. Triethylamine (100 μL, 160 equiv) and tris hydroxymethylphosphine (50 mg, 80 equiv) were added and the resulting solution was stirred at room temperature for 1 h. The pale yellow reaction mixture was diluted with CH$_2$Cl$_2$ (5 mL) and washed with water (3×5 mL). The aqueous phase was extracted with CH$_2$Cl$_2$ (3×5 mL) and the combined organics were dried over Na$_2$SO$_4$, filtered and concentrated. The crude product was analyzed by HPLC using a Waters model 600 pump and controller coupled to a Waters model 2487 dual λ absorbance detector.

Analytical HPLC was performed on a Waters Nova-Pak© silica column (3.9×150 mm) using a gradient of 5→20% EtOAc/hexanes (20 min) and a flow rate of 1.0 mL/min, monitoring at 260 nm. Semi-preparative HPLC was performed on a Waters prep Nova-Pak© silica column (7.8×300 mm) using a gradient of 5→20% EtOAc/hexanes (20 min) and a flow rate of 2.5 mL/min, monitoring at 260 nm.

Fractions collected during semi-preparative HPLC were checked by analytical HPLC for purity. Clean fractions were concentrated to give 46α (2.0 mg, 2% yield) as a clear oil. [α]$^{24}_D$: +21.7° (c 0.63, CH$_2$Cl$_2$); IR (thin film) 2361, 2338, 1095, 668 cm$^{-1}$; $^1$H NMR (500 MHz, CDCl$_3$) δ 7.35-7.03 (m, 60H), 5.77-5.71 (m, 1H), 5.31 (s, 1H), 5.21 (s, 1H), 4.98-4.86 (m, 7H), 4.82 (d, J=10.7 Hz, 1H), 4.77 (s, 1H), 4.72-4.61 (m, 5H), 4.60-4.53 (m, 8H), 4.50-4.46 (m, 6H), 4.44 (d, J=12.2 Hz, 1H), 4.36 (d, J=11.6 Hz, 1H), 4.28 (d, J=12.2 Hz, 1H), 4.05 (t, J=9.5 Hz, 1H), 4.01-3.98 (m, 1H), 3.96-3.84 (m, 11H), 3.82-3.65 (m, 7H), 3.64-3.49 (m, 8H), 3.32-3.27 (m, 1H), 2.08-2.00 (m, 4H), 1.57-1.55 (m, 2H), 1.10-1.02 (m, 24H); HSQC data $^{13}$C (125 MHz)/$^1$H (500 MHz): 100.5/5.31 (1a), 73.1/4.15 (2a), 80.1/3.94 (3a), 99.3/4.90 (1b), 75.1/4.16 (2b), 80.7/3.89 (3b), 98.0/4.77 (1c), 74.8/3.75 (2c), 80.7/3.88 (3c), 99.8/5.21 (1d), 74.9/3.86 (2d), 71.2/3.69 (3d), 66.8/3.59

(6d); HMBC cross peaks $^{13}$C (125 MHz): 75.1 (a→b), 74.8 (b→c), 66.8 (c→d); ESI MS m/z (M+Na)$^+$ calcd 1993.9705, found 1993.9747.

Example 26

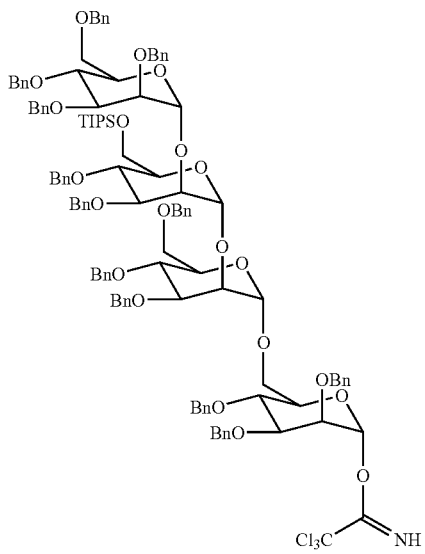

47

2,3,4,6-Tetra-O-benzyl-α-D-mannopyranosyl-(1→2)-3,4-di-O-benzyl-6-O-trisopropylsilyl-α-D-mannopyranosyl-(1→2)-3,4,6-tri-O-benzyl-α-D-mannopyranosyl-(1→6)-2,3,4-tri-O-benzyl-α-D-mannopyranosyl trichloracetimidate 47. n-Pentenyl glycoside 46 (200 mg, 0.10 mmol) was suspended In 8:1 acetonitrile/water (8 mL) and N-bromosuccinimide (63 mg, 0.35 mmol) was added. The orange mixture was stirred in the dark for 1 h, then quenched by the addition of sat. aqueous Na$_2$S$_2$O$_3$ (5 mL). Water (25 mL) was added, and the mixture was washed with CH$_2$Cl$_2$ (4×50 mL). The combined organic phases were dried (Na$_2$SO$_4$), filtered and concentrated. Silica gel column chromatography (10→20% EtOAc/hexanes) afforded the anomeric lactols (128 mg, 67%) as a colorless oil. The lactols (64 mg, 34 μmol) were dissolved In CH$_2$Cl$_2$ (1 mL) and DBU (1 μL, 7 μmol) and Cl$_3$CCN (34 μL, 340 μmol) were added. After 1 h at room temperature the crude mixture was filtered through a pad of silica gel, washing with 30% EtOAc/hexanes. The crude material was concentrated, then purified by silica gel column chromatography (10% EtOAc/hexanes) to afford 47 (52 mg, 75%) as a colorless oil. [α]$^{24}_D$: +10.9° (c 0.90, CH$_2$Cl$_2$); IR (thin film) 2864, 2360, 1454, 1096, 697 cm$^{-1}$; $^1$H NMR (500 MHz, CDCl$_3$) δ 8.47 (s, 1H), 7.37-6.97 (m, 60H), 6.21 (d, J=2.1 Hz, 1H), 5.22 (s, 1H), 5.12 (s, 1H), 4.84-4.18 (m, 22H), 4.08-4.07 (m, 1H), 4.02-3.42 (m, 21H), 0.97-0.95 (m, 18H); $^{13}$C NMR (125 MHz, CDCl$_3$) δ 160.1, 139.2, 139.1, 139.0, 139.0, 138.8, 138.7, 138.7, 138.6, 138.4, 138.2, 138.0, 128.7, 128.6, 128.6, 128.6, 128.5, 128.4, 128.4, 128.4, 128.4, 128.3, 128.3, 128.2, 128.2, 128.1, 128.1, 128.0, 128.0, 127.9, 127.9, 127.9, 127.8, 127.8, 127.7, 127.7, 127.6, 127.6, 127.5, 127.5, 127.5, 127.4, 100.4, 99.8, 99.0, 95.9, 80.4, 80.1, 80.0, 79.5, 77.5, 77.2, 77.0, 75.2, 76.1, 75.0, 75.0, 74.7, 74.6, 74.2, 74.1, 73.8, 73.7, 73.5, 73.3, 73.1, 72.8, 72.7, 72.5, 72.4, 72.3, 72.2, 71.9, 71.7, 69.3, 69.1, 66.3, 62.9, 18.4, 18.3, 18.3, 18.3, 12.2, 12.2; ESI MS m/z (M+Na)$^+$ calcd 1993.9705, found 1993.9747.

Example 27

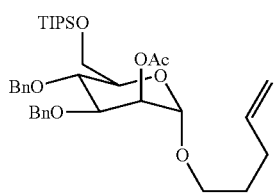

49 n-Pentenyl 2-O-acetyl-3,4-di-O-benzyl-6-O-triisopropylsilyl-α-D-mannopyranoside 49. [α]$^{24}_D$: +27.2° (c 2.5, CHCl$_3$); IR (thin film) 2941, 2865, 1746, 1369, 1236 cm$^{-1}$; $^1$H NMR (400 MHz, CDCl$_3$) δ 7.38-7.27 (m, 10H), 5.80 (ddd, J=6.6, 10.2, 17.1 Hz, 1H), 5.33 (dd, J=1.8, 3.2 Hz, 1H), 4.98 (d, J=10.2 Hz, 1H), 4.92 (d, J=10.7 Hz, 1H), 4.76 (d, J=1.6 Hz, 1H), 4.73 (d, J=11.2 Hz, 1H), 4.66 (d, J=10.7 Hz, 1H), 4.58 (d, J=11.2 Hz, 1H), 4.03-3.98 (m, 4H), 3.71-3.63 (m, 2H), 3.39 (dd, J=6.5, 9.6 Hz, 1H), 2.13 (s, 1H), 2.11-2.07 (m, 2H), 1.69-1.62 (m, 2H), 1.17-1.05 (m, 21H); $^{13}$C-NMR (100 MHz, CDCl$_3$) δ 170.8, 138.8, 138.3, 138.2, 128.6, 128.3, 128.2, 127.9, 127.9, 115.1, 97.6, 78.4, 75.5, 74.4, 73.1, 72.0, 69.3, 67.1, 62.9, 30.5, 28.8, 21.3, 18.2, 18.2, 12.2; ESI MS m/z (M+Na)$^+$ calcd 649.353, found 649.351.

Example 28

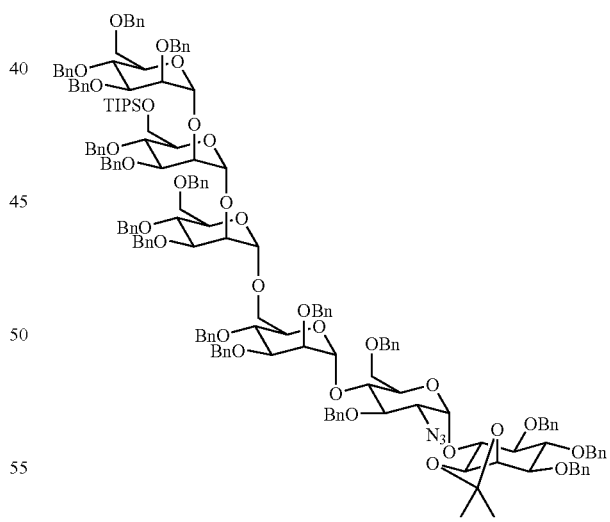

48

O-(2,3,4,6-Tetra-O-benzyl-α-D-mannopyranosyl)-(1→2)-O-(3,4-di-O-benzyl-6-O-triisopropylsilyl-α-D-mannopyranosyl)-(1→2)-O-(3,4,6-tri-O-benzyl-α-D-mannopyranosyl)-(1→6)-O-(2,3,4-tri-O-benzyl-α-D-mannopyranosyl)-(1→4)-O-(2-azido-3,6-di-O-benzyl-2-deoxy-α-D-glucopyranosyl)-(1→6)-3,4,5-tri-O-benzyl-1,2-O-isopropylidene-D-myo-inositol 40. A mixture of acceptor 21 (18.1 mg, 21.2 μmol) and donor 47 (18.4 mg, 9 μmol) was azeotroped with toluene (3×4 mL), then dried in vacuo for 1.5 h. CH$_2$Cl$_2$ (1 mL) and 4 Å activated molecular sieves (20 mg) were added, followed by a 0.09 M solution of TMSOTf in CH$_2$Cl$_2$ (10 µL, 0.90 µmol). After 1 h at room temperature, NEt$_3$ (10 µL) was added and the mixture was concentrated. Silica gel column chromatography (1→3% EtOAc/toluene) afforded 40 (8.0 mg, 32%) as a clear oil. Analytical data was Identical to that reported previously in this section.

INCORPORATION BY REFERENCE

All of the patent and publications cited herein are hereby incorporated by reference.

REFERENCES CITED

[1] Ikezawa, H. *Biol. Pharm. Bull.* 2002, 25, 409.
[2] Guha-Niyogi, A.; Sullivan, D. R.; Turco, S. *J. Glycobiol.* 2001, 11, 45.
[3] Jones, D. R.; Varela-Nieto, I. *Int. J. Biochem. Cell Biol.* 1998, 30, 313.
[4] Tomita, M. *Biochem. Biophys. Acta* 1999, 1445, 269.
[5] Screaton, R. A.; DeMarte, L.; Dráber, P.; Stanners, C. P. *J. Cell Biol.* 2000, 150, 613.
[6] Ferguson, M. A. J. *J. Cell Sci.* 1999, 112, 2799.
[7] a) Mayer, T. G.; Kratzer, B.; Schmidt, R. R. *Angew. Chem. Int. Ed.* 1994, 33, 2177, b) Mayer, T. G.; Schmidt, R. R. *Eur. J. Org. Chem.* 1999, 1153. c) Baeschlin, D. K.; Green, L. G.; Hahn, M. G.; Hinzen, B.; Ince, S. J.; Ley, S. V. *Tetrahedron Asymm.* 2000, 11, 173.
[8] a) Murakata, C.; Ogawa, T. *Carbohydr. Res.* 1992, 234, 75. b) Murakata, C.; Ogawa, T. *Carbohydr. Res.* 1992, 235, 95. c) Baeschlin, D. K.; Chaperon, A. R.; Green, L, G.; Hahn, M. G.; Ince, S. J.; Ley, S. V. *Chem. Eur. J.* 2000, 6, 172.
[9] a) Campbell, A. S.; Fraser-Reid, B. J. *J. Am. Chem. Soc.* 1995, 117, 10387. b) Tailler, D.; Ferrieres, V.; Pekari, K.; Schmidt, R. R. *Tetrahedron Lett.* 1999, 40, 679.
[10] a) Frick, W.; Bauer, A.; Bauer, J.; Wied, S.; Muller, G. *Biochemistry* 1998, 37, 13421. b) Garegg, P. J.; Konradsson, P.; Oscarson, S.; Ruda, K. *Tetrahedron* 1997, 53, 17727. c) Martin-Lomas, M.; Khiar, N.; Garcia, S.; Koessler, J.-L.; Nieto, P. M.; Rademacher, T. W. *Chem. Eur. J.* 2000, 6, 3608.
[11] Pekari, K.; Tailler, D.; Weingart, R.; Schmidt, R. R. *J. Org. Chem.* 2001, 66, 7432.
[12] Udodong, U. E.; Madsen, R.; Roberts, C.; Fraser-Reid, B. *J. Am. Chem. Soc.* 1993, 115, 7886.
[13] Taubes, G. *Science,* 2000, 290, 434.
[14] Berhe, S.; Schofield, L.; Schwarz, R. T.; Gerold, P. *Mol. Biochem. Parasitol.* 1999, 103, 273.
[15] a) WHO; *World Health Stat Q* 1992, 45, 257. b) Schofield, L.; Hackett, F. *J. Exp. Med.* 1993, 177, 145. c) Tachado, S. D.; Schofield, L. *Biochem. Biophys. Res. Commun.* 1994, 205, 984. d) Schofield, L.; Novakovic, S.; Gerold, P.; Schwarz, R. T.; McConville, M. J.; Tachado, S. D. *J. Immunol.* 1996, 156, 1886. e) Tachado, S. D.; Gerold, P.; McConville, M. J.; Baldwin, T.; Quilici, D.; Schwarz, R. T.; Schofield, L. *Proc. Natl. Acad. Sci. USA* 1997, 94, 4022.
[16] Naik, R. S.; Branch, O. H.; Woods, A. S.; Vijaykumar, M.; Perkins, D. J.; Nahlen, B. L.; Lal, A. A.; Cotter, R. J.; Costello, C. E.; Ockenhouse, C. F.; Davidson, E. A.; Gowda, D. C. *J. Exp. Med.* 2000, 192, 1563.
[17] Kwiatkowski, D.; Marsh, K. *Lancet* 1997, 350, 1696.
[18] For a review see: Campbell, S. A. *Glycoscience: Chemistry and Biology*; Fraser-Reid, B. O.; Tatsuta, K.; Thiem, J., Eds.; Springer-Verlag: Berlin, 2001; 1.
[19] Plante, O. J.; Palmacci, E. R.; Seeberger, P. H. *Science* 2001, 291, 1523.
[20] a) Bruzik, K. S.; Tsai, M.-D. *J. Am. Chem. Soc.* 1992, 114, 6361. b) Prestwich, G. D. *Acc. Chem. Res.* 1996, 29, 503. c) Jaramillo, C.; Chiara, J. L.; Martin-Lomas, M. *J. Org. Chem.* 1994, 59, 3135. d) Chen, J.; Dorman, G.; Prestwich, G. D. *J. Org. Chem.* 1996, 61, 393. e) Bender, S. L.; Budhu, R. J. *J. Am. Chem. Soc.* 1991, 113, 9883. f) Takahashi, H.; Kittaka, H.; Ikegami, S. *J. Org. Chem.* 2001, 66, 2705.
[21] Chaudhary, S. K.; Hernandez, O. *Tetrahedron Left.* 1979, 20, 95.
[22] Swern, D.; Mancuso, A. J.; Huang, S.-L. *J. Org. Chem.* 1978, 43, 2480.
[23] a) Ferrier, R. J. *J. Chem. Soc. Chem. Comm.* 1979, 1455. b) Blattner, R.; Ferrier, R. J.; Prasit, P. *J. Chem. Soc. Chem. Comm.* 1980, 944. c) Ferrier, R. J.; Haines, S. R. *Carbohydr. Res.* 1984, 130, 135. d) Blattner, R.; Ferrier, R. J.; Haines, S. R. *J. Chem. Soc. Perkin Trans.* 1 1985, 2413. e) Yamauchi, N.; Terachi, T.; Eguchi, T.; Kakinuma, K. *Tetrahedron* 1994, 50, 4125.
[24] Jia, Z. J.; Olsson, L.; Fraser-Reid, B. *J. Chem. Soc. Perkin Trans.* 1, 1998, 631.
[25] Peters, T.; Weimar, T. *Liebigs Ann. Chem.* 1991, 237.
[26] Albert, R.; Dan, K.; Pleschko, R.; Siutz, A. F. *Carbohydr. Res.* 1985, 137, 282.
[27] DeNinno, M. P.; Etienne, J. B.; Duplantier, K. C. *Tetrahedron Left.* 1995, 36, 669.
[28] a) Alper, P. B.; Hung, S.-C.; Wong, C.-H. *Tetrahedron Left.* 1996, 37, 6029. b) Zaloom, J.; Roberts, D. C. *J. Org. Chem.* 1981, 46, 5173.
[29] Dhawan, S. N.; Chick, T. L.; Goux, W. *J. Carbohydr. Res.* 1988, 172, 297.
[30] Zhang, G.-T.; Guo, Z.-W.; Hui, Y.-Z. *Synthetic Comm.* 1997, 27, 1907.
[31] For a review see: Schmidt, R. R.; Kinzy, W. *Adv. Carbohydr. Chem. Biochem.* 1994, 50, 21.
[32] Johnston, B. D.; Pinto, B. M. *J. Org. Chem.* 2000, 65, 4607.
[33] See experimental section.
[34] Smrt, J.; Catlin, J. *Tetrahedron Lett.* 1970, 11, 5081.
[35] White, N. J.; Ho, M. *Adv. Parasitol.* 1992, 31, 83.
[36] Chang, W. L. *Infect. Immun.* 2001, 69, 7341.
[37] Crich, D.; Sun, S. *Tetrahedron* 1998, 54, 8321.
[38] Pekari, K.; Tailler, D.; Weingart, R.; Schmidt, R. R. *J. Org. Chem.* 2001, 66, 7432.
[39] Fraser-Reid, B.; Udodong, U. E.; Wu, Z.; Ottoson, H.; Merritt, J. R.; Rao, C. S.; Roberts, C.; Madsen, R. *Synlett* 1992, 927.
[40] a) Schwab, P.; Grubbs, R. H.; Ziller, J. W. *J. Am. Chem. Soc.* 1996, 118, 100. b) Grubbs, R. H.; Miller, S. J.; Fu, G. C. *Acc. Chem. Res.* 1995, 28, 446. c) Schmalz, H. G. *Angew. Chem. Int Ed.* 1995, 34, 1833.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound represented by formula I:

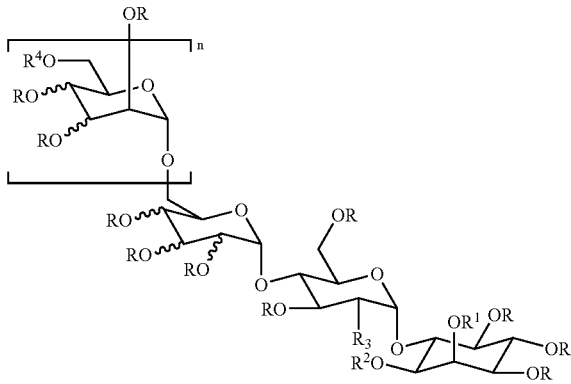

wherein,
n is 3, or 4;
R represents independently for each occurrence H, alkyl, aryl, —CH$_2$-aryl, —C(O)-alkyl, —C(O)-aryl, or —Si(alkyl)$_3$;
R$^1$ and R$^2$ are independently H, —CH$_2$-aryl, —C(O)-alkyl, —C(O)-aryl, —Si(alkyl)$_3$; or R$^1$ and R$^2$ taken together are C(CH$_3$)$_2$, P(O)OH, or P(O)OR$^5$;
R$^3$ is amino, —N$_3$, or —NH$_3$X;
R$^4$ represents independently for each occurrence alkyl, aryl, —CH$_2$-aryl, —C(O)-alkyl, —C(O)-aryl, —Si(alkyl)$_3$, or —P(O)(OR$^5$)$_2$;
R$^5$ represents independently for each occurrence H, Li$^+$, Na$^+$, Rb$^+$, Cs$^+$, aryl, or an optionally substituted alkyl group; and
X is a halogen, alkyl carboxylate, or aryl carboxylate.
2. The compound of claim 1, wherein n is 3.
3. The compound of claim 1, wherein R is H.
4. The compound of claim 1, wherein R$^1$ and R$^2$ taken together are P(O)OR$^5$.
5. The compound of claim 1, wherein R$^3$ is N$_3$.
6. The compound of claim 1, wherein R$^3$ is —NH$_3$X.
7. The compound of claim 1, wherein R$^4$ represents independently for each occurrence —CH$_2$Ph, or —Si(alkyl)$_3$.
8. The compound of claim 1, wherein R$^4$ represents independently for each occurrence —CH$_2$Ph, or —P(O)OR$^5$; and R$^5$ is an optionally substituted alkyl group.
9. A compound represented by formula II:

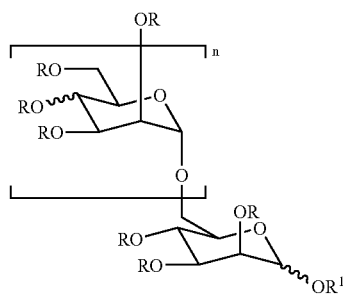

wherein,
n is 3, or 4;
R represents independently for each occurrence H, alkyl, aryl, —CH$_2$-aryl, —C(O)-alkyl, —C(O)-aryl, or —Si(alkyl)$_3$;
R$^1$ is —(CH$_2$)$_m$CH=CH$_2$ or trichloroacetimidate; and
m is 1-6.
10. The compound of claim 9, wherein n is 3.
11. The compound of claim 9, wherein m is 3.
12. The compound of claim 10, wherein R represents independently for each occurrence —CH$_2$-aryl or —Si(alkyl)$_3$.
13. The compound of claim 10, wherein R represents independently for each occurrence benzyl or —Si(iPr)$_3$.
14. The compound of claim 10, wherein R$^1$ is trichloroacetimidate and R represents independently for each occurrence benzyl or —Si(iPr)$_3$.
15. The compound of claim 10, wherein said compound of formula II is selected from the group consisting of:

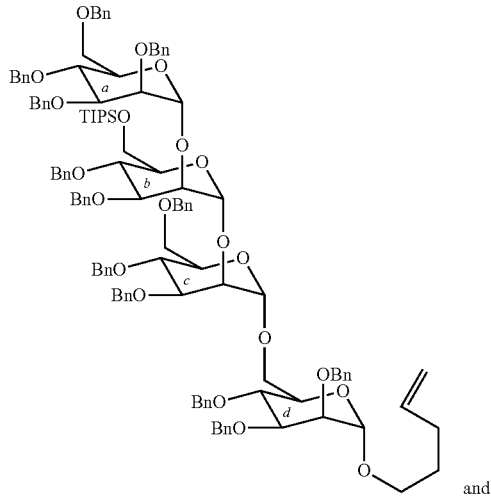

and

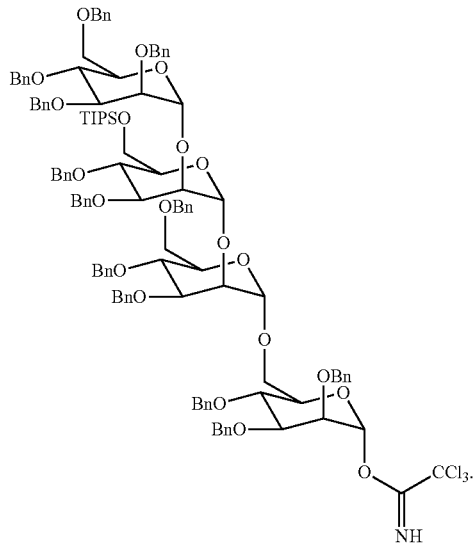

16. A compound represented by formula I:

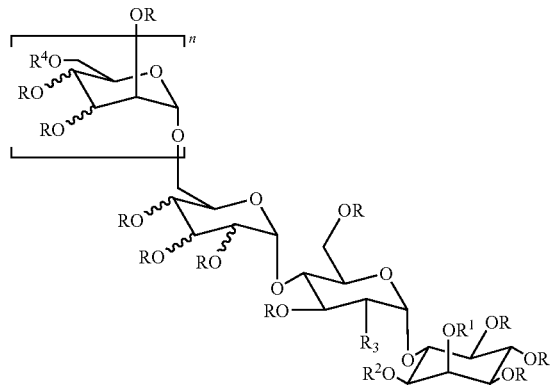

wherein, n is 1;

R represents independently for each occurrence H, alkyl, aryl, —$CH_2$-aryl, —C(O)-alkyl, —C(O)-aryl, or —Si(alkyl)$_3$;

$R^1$ and $R^2$ are independently H, —$CH_2$-aryl, —C(O)-alkyl, —C(O)-aryl, —Si(alkyl)$_3$; or $R^1$ and $R^2$ taken together are C(CH$_3$)$_2$, P(O)OH, or P(O)OR$^5$;

$R^3$ —NH$_3$X;

$R^4$ represents independently for each occurrence H, alkyl, aryl, —$CH_2$-aryl, —C(O)-alkyl, —C(O)-aryl, —Si(alkyl)$_3$, or —P(O)(OR$^5$)$_2$;

$R^5$ represents independently for each occurrence H, Li$^+$, Na$^+$, K$^+$, Rb$^+$, Cs$^+$, aryl, or an optionally substituted alkyl group;

$R^6$ represents independently for each occurrence alkyl, aryl, —$CH_2$-aryl, -C(O)-alkyl, —C(O)-aryl, —Si(alkyl)$_3$, or -P(O)(OR$^5$)$_2$; and X is a halogen, alkyl carboxylate, or aryl carboxylate.

17. The compound of claim 16, wherein R is H; $R^1$ and $R^2$ taken together are P(O)OR$^5$; $R^4$ is H; and $R^6$ is -P(O)(OR$^5$)$_2$.

18. A compound represented by formula I:

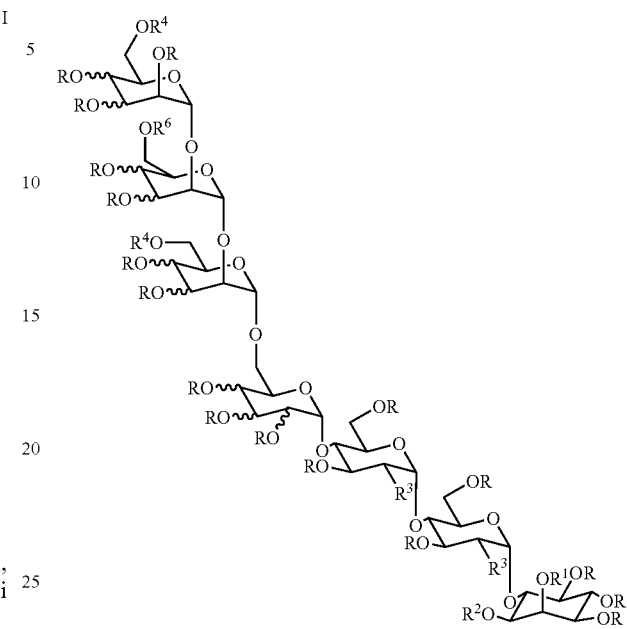

wherein, n is 1;

R represents independently for each occurrence H, alkyl, aryl, —CH$^2$-aryl, —C(O)-alkyl, —C(O)-aryl, or —Si(alkyl)$_3$;

$R^1$ is —$CH_2$-aryl, —C(O)-alkyl, —C(O)-aryl, —Si(alkyl)$_3$;

$R^2$ is —$CH_2$-aryl, —C(O)-alkyl, —C(O)-aryl, —Si(alkyl)$_3$; or $R^1$ and $R^2$ taken together are C(CH$_3$)$_2$, P(O)OH, or P(O)OR$^5$;

$R^3$ is amino, —N$_3$, or —NH$_3$X;

$R^4$ represents independently for each occurrence alkyl, aryl, —$CH_2$-aryl, —C(O)-alkyl, —C(O)-aryl, —Si(alkyl)$_3$, or —P(O)(OR$^5$)$_2$;

$R^5$ represents independently for each occurrence H, Li$^+$, Na$^+$, K$^+$, Rb$^+$, Cs$^+$, aryl, or an optionally substituted alkyl group; and X is a halogen, alkyl carboxylate, or aryl carboxylate.

\* \* \* \* \*

UNITED STATES PATENT AND TRADEMARK OFFICE
CERTIFICATE OF CORRECTION

PATENT NO.      : 7,943,594 B2
APPLICATION NO. : 10/520963
DATED           : May 17, 2011
INVENTOR(S)     : Seeberger et al.

It is certified that error appears in the above-identified patent and that said Letters Patent is hereby corrected as shown below:

In claim 12, column 56 at line 10, "claim 10" should read --claim 9--.

In claim 13, column 56 at line 12, "claim 10" should read --claim 9--.

In claim 14, column 56 at line 14, "claim 10" should read --claim 9--.

In claim 15, column 56 at line 17, "claim 10" should read --claim 9--.

In claim 16, column 57 at lines 2-23, the text

"16. A compound represented by formula I:

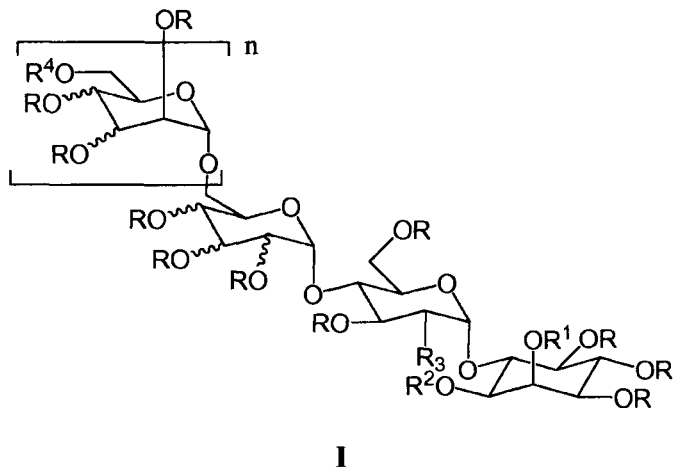

wherein,
n is 1;"

should read

Signed and Sealed this
Twelfth Day of July, 2011

David J. Kappos
*Director of the United States Patent and Trademark Office*

--16. A compound represented by formula I:
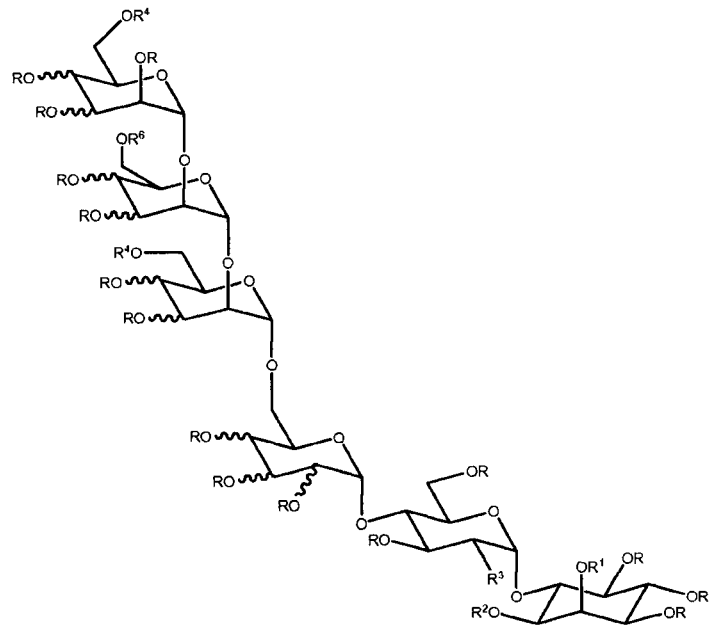
I
wherein,--.
In claim 18, column 58 at lines 1-27, the text
"18. A compound represented by formula I:
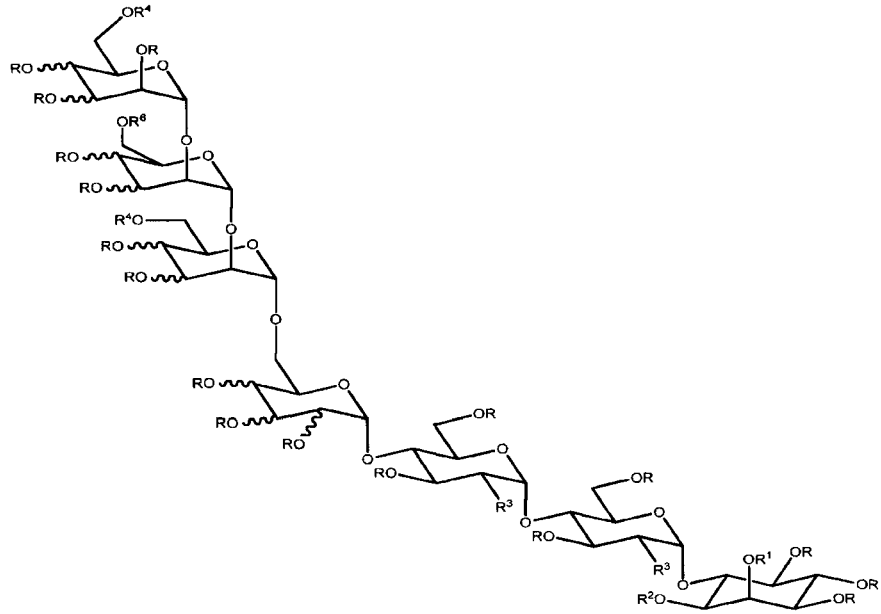
wherein,"

CERTIFICATE OF CORRECTION (continued)

should read

--18. A compound represented by formula I:

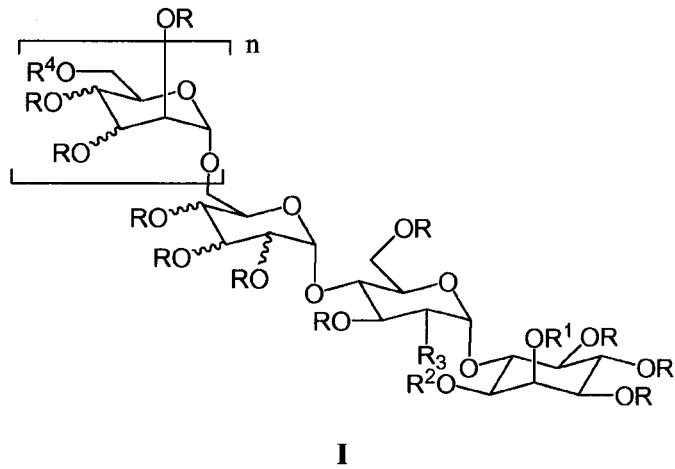

I wherein,--.